(12) United States Patent
Shunnarah et al.

(10) Patent No.: US 12,196,613 B2
(45) Date of Patent: *Jan. 14, 2025

(54) HANDHELD BIOMARKER MEASURING DEVICE USING NANOPOROUS ANODIC ALUMINUM OXIDE SUBSTRATE AND APPLICATION OF SAME

(71) Applicant: MetGen, Incorporated, Atlanta, GA (US)

(72) Inventors: Richard D. Shunnarah, Atlanta, GA (US); Hugh F. Garvey, Seminole, FL (US); Lenzi J. Williams, Clearwater, FL (US); Devon Fish, Largo, FL (US)

(73) Assignee: METGEN, INCORPORATED, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/441,250

(22) Filed: Feb. 14, 2024

(65) Prior Publication Data

US 2024/0183711 A1    Jun. 6, 2024

Related U.S. Application Data

(63) Continuation-in-part of application No. 18/218,651, filed on Jul. 6, 2023, now Pat. No. 11,933,671, which
(Continued)

(51) Int. Cl.
*G01J 3/02* (2006.01)
*G01J 3/44* (2006.01)
(Continued)

(52) U.S. Cl.
CPC .......... *G01J 3/0272* (2013.01); *G01J 3/0256* (2013.01); *G01J 3/4412* (2013.01);
(Continued)

(58) Field of Classification Search
CPC ...... G01J 3/0272; G01J 3/0256; G01J 3/4412; G01N 21/658; G01N 33/523; G01N 33/6812
(Continued)

(56) References Cited

U.S. PATENT DOCUMENTS

| 7,688,440 | B2 * | 3/2010 | Clarke | .................. | G01N 21/65 356/301 |
| 2011/0027901 | A1 * | 2/2011 | Gaster | .................. | G01N 33/574 422/430 |
| 2015/0211998 | A1 * | 7/2015 | Kuo | ....................... | G01N 21/65 356/301 |

OTHER PUBLICATIONS

Santos, Materials 2014, 7, 4297-4320; doi:10.3390/ma7064297. (Year: 2014).*
(Continued)

*Primary Examiner* — Christine T Mui
(74) *Attorney, Agent, or Firm* — Locke Lord LLP; Tim Tingkang Xia, Esq.

(57) ABSTRACT

A handheld Surface-Enhanced Raman Spectroscopy (SERS) device for detecting a biomarker in a sample collected from a subject. The device comprises a laser generator configured to produce a laser beam; a nanoporous anodic aluminum oxide (NAAO) substrate configured to receive the sample collected from the subject; wherein the laser beam reaches the sample on the NAAO substrate and is reflected or deflected to produce a light signal; and a light sensor configured to receive the light signal reflected or deflected from the sample; wherein the device is handheld and detects the biomarker in the sample; wherein the NAAO substrate comprises a multilayered nanoporous aluminum layer; wherein the multilayered nanoporous aluminum layer comprises a base aluminum layer, and a nanoporous aluminum
(Continued)

layer on top of the base aluminum layer; and wherein the nanoporous aluminum layer comprises a plurality of nanocavities.

24 Claims, 38 Drawing Sheets

Related U.S. Application Data is a continuation of application No. 17/888,621, filed on Aug. 16, 2022, now Pat. No. 11,747,199, application No. 18/441,250 is a continuation-in-part of application No. 18/218,669, filed on Jul. 6, 2023, now Pat. No. 11,933,672, which is a continuation of application No. 17/888,621, filed on Aug. 16, 2022, now Pat. No. 11,747,199.

(60) Provisional application No. 63/234,771, filed on Aug. 19, 2021.

(51) Int. Cl.
*G01N 21/65* (2006.01)
*G01N 33/52* (2006.01)
*G01N 33/68* (2006.01)

(52) U.S. Cl.
CPC ......... *G01N 21/658* (2013.01); *G01N 33/523* (2013.01); *G01N 33/6812* (2013.01)

(58) Field of Classification Search
USPC ...................................... 422/82.9, 50, 82.09
See application file for complete search history.

(56) References Cited

OTHER PUBLICATIONS

Kassu, Sensors 2015, 15, 29924-29937; doi:10.3390/s151229778. (Year: 2015).*
Liu, Theranostics, 2022; 12(4): 1870-1903. doi: 10.7150/thno. 66859. (Year: 2022).*

* cited by examiner

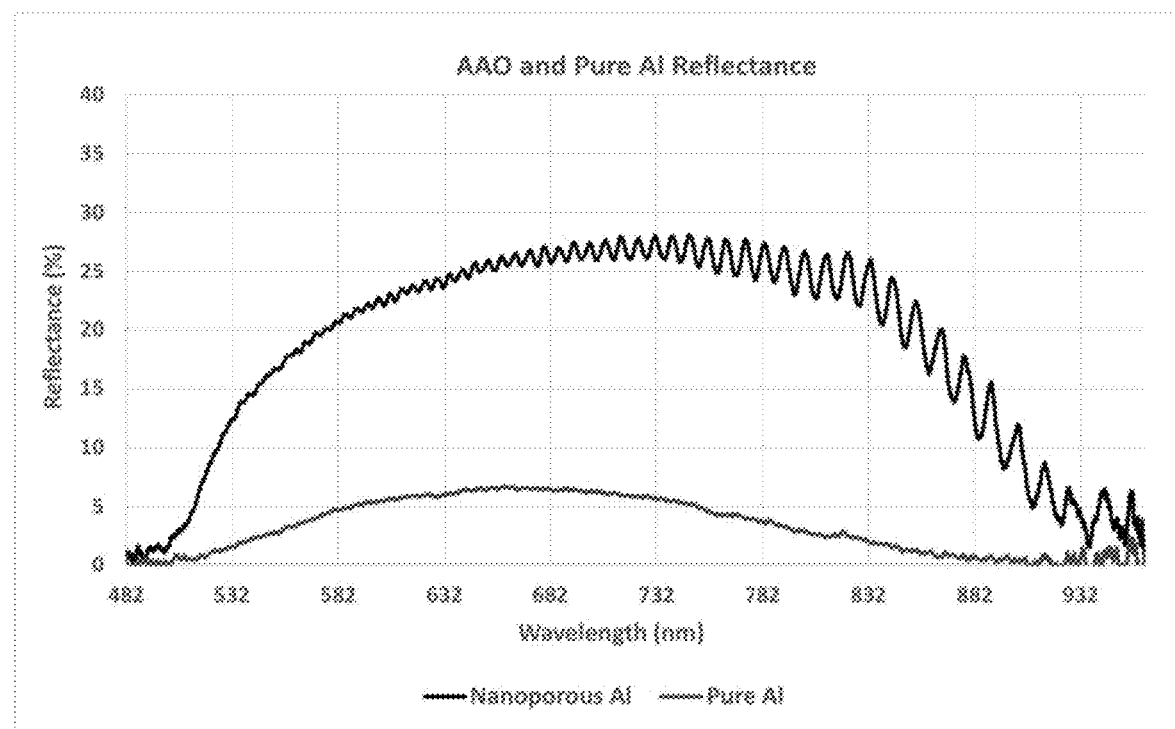
Fig. 1A
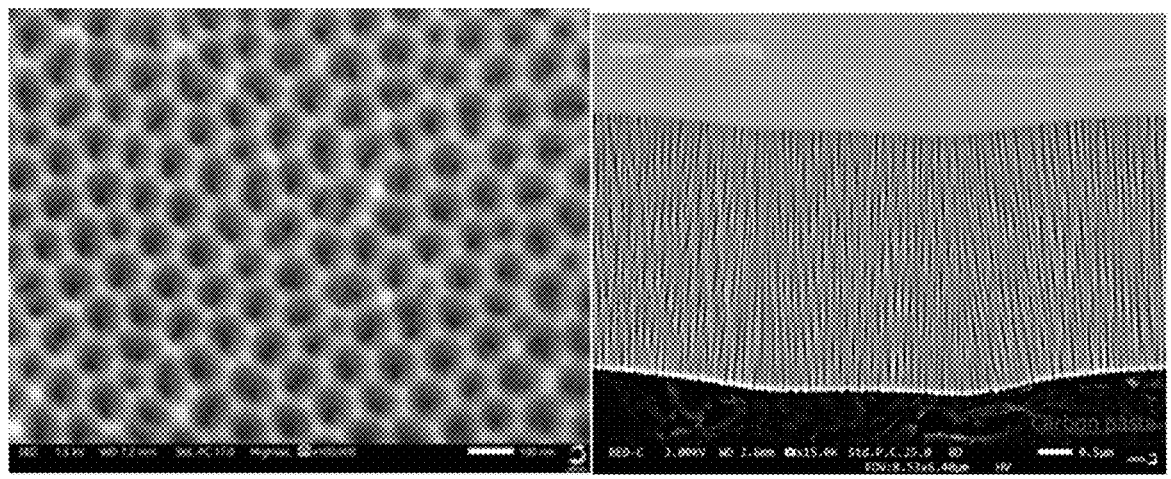
Fig. 1B
Fig. 1C

HANDHELD BIOMARKER MEASURING DEVICE USING NANOPOROUS ANODIC ALUMINUM OXIDE SUBSTRATE AND APPLICATION OF SAME

CROSS-REFERENCE TO RELATED PATENT APPLICATIONS

This application is a continuation-in-part application of U.S. application Ser. No. 18/218,651, filed Jul. 6, 2023, which is a continuation application of U.S. application Ser. No. 17/888,621, filed Aug. 16, 2022, now U.S. Pat. No. 11,747,199, which itself claims priority to and the benefit of U.S. Provisional Application No. 63/234,771, filed Aug. 19, 2021, which are incorporated herein in their entireties by reference.

This application is also a continuation-in-part application of U.S. application Ser. No. 18/218,669, filed Jul. 6, 2023, which is a continuation application of U.S. application Ser. No. 17/888,621, filed Aug. 16, 2022, now U.S. Pat. No. 11,747,199, which itself claims priority to and the benefit of U.S. Provisional Application No. 63/234,771, filed Aug. 19, 2021, which are incorporated herein in their entireties by reference.

FIELD OF THE INVENTION

The present disclosure relates generally to the field of biomedical engineering, and more particularly to a handheld biomarker measuring device using anodic aluminum oxide substrate for measuring selected biomarkers.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Numerous medical conditions/diseases require patients to monitor biomarkers of those medical conditions/diseases from time to time. Traditionally, the patients go to a clinic to have tests performed by a medical professional for measuring the biomarkers. Testing places an extra burden and cost for those patients who have mobility issues or cannot visit clinics due to various reasons.

On the other hand, at-home testing is a growing part of healthcare that, like telemedicine, has captured more interest since and after the COVID-19 pandemic. Direct-to-consumer at-home tests now include a diverse range of test types offered by numerous companies that are readily available, providing customers and patients with more options than ever before.

However, for testing different biomarkers, different test kits are required, and each kit has different requirements and procedures to follow. Moreover, an additional test kit is required for each round of testing, further adding to the cost for at-home biomarker test.

Therefore, there remains an imperative need for a system/device to allow patients to perform biomarker testing at home that is capable of testing more than one biomarker in a more convenient way, that is cost effective, and with ease of operation.

SUMMARY OF THE INVENTION

In light of the foregoing, this invention discloses a handheld Surface-Enhanced Raman Spectroscopy (SERS) device for detecting a biomarker in a sample collected from a subject. The device comprises a laser generator configured to produce a laser beam; a nanoporous anodic aluminum oxide (NAAO) substrate configured to receive the sample collected from the subject; wherein the laser beam reaches the sample on the NAAO substrate and is reflected or deflected to produce a light signal; and a light sensor configured to receive the light signal reflected or deflected from the sample; wherein the device is handheld and detects the biomarker in the sample; wherein the NAAO substrate comprises a multilayered nanoporous aluminum layer; wherein the multilayered nanoporous aluminum layer comprises a base aluminum layer, and a nanoporous aluminum layer on top of the base aluminum layer; and wherein the nanoporous aluminum layer comprises a plurality of nanocavities.

In one embodiment, the device further comprises a beam splitter locates between the laser generator and the NAAO substrate.

In one embodiment, the device further comprises a bandpass filter located between the beam splitter and the light sensor; wherein the bandpass filter selectively permits the light signal having certain wavelengths to pass through; and wherein the certain wavelengths are adjustable.

In one embodiment, the beam splitter permits the passing of the laser beam produced by the laser generator on one of its two sides, and is configured to reflect at least a portion of the light signal reflected or deflected by the sample on the NAAO substrate on the other of its two sides.

In one embodiment, certain wavelengths are selected for determining the biomarker in the sample.

In one embodiment, the light sensor is configured to receive the light signal passes through the bandpass filter.

In one embodiment, the device further comprises a test strip holder; wherein the test strip holder is configured to receive a test strip comprising the NAAO substrate.

In one embodiment, the device further comprises a focusing lens; wherein the focusing lens is disposed between the test strip holder and the beam splitter.

In one embodiment, the NAAO substrate is a gold layered NAAO substrate; wherein a gold layer is disposed on top of the NAAO substrate via a method of air-water-oil interfacial self-assembly.

In one embodiment, the NAAO substrate gold layer comprises gold nanoparticles.

In one embodiment, the gold nanoparticles are nanorods.

In one embodiment, the multilayered nanoporous aluminum layer comprises an ordered nanoporous alumina layer grown on top of an aluminum substrate.

In one embodiment, the NAAO substrate has a high surface area to volume ratio.

In one embodiment, the device comprises a communication unit, wherein the communication unit is configured to communicate with an interactive display for receiving an input and displaying an output.

In one embodiment, the input comprises the biomarker.

In one embodiment, the certain wavelengths are configured to be adjusted according to the biomarker.

In one embodiment, the biomarker comprises a biomarker of a dementia disease.

In one embodiment, the biomarker comprises a biomarker of a cancer.

In one embodiment, the biomarker comprises a biomarker of a heart disease.

In one embodiment, the biomarker comprises a biomarker of a neuromuscular disorder.

In one embodiment, the biomarker comprises a hormone or a steroid.

In one embodiment, the biomarker comprises a nutrient.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 1A shows NAAOs were characterized by collecting the visible reflectance spectrum for the substrate before and after anodization. FIG. 1B shows SEM images of NAAOs collected using the JEOL IT700HR. FIG. 1C shows a cross-sectional view SEM image of NAAO substrate.

DETAILED DESCRIPTION OF THE INVENTION

Figure 2:
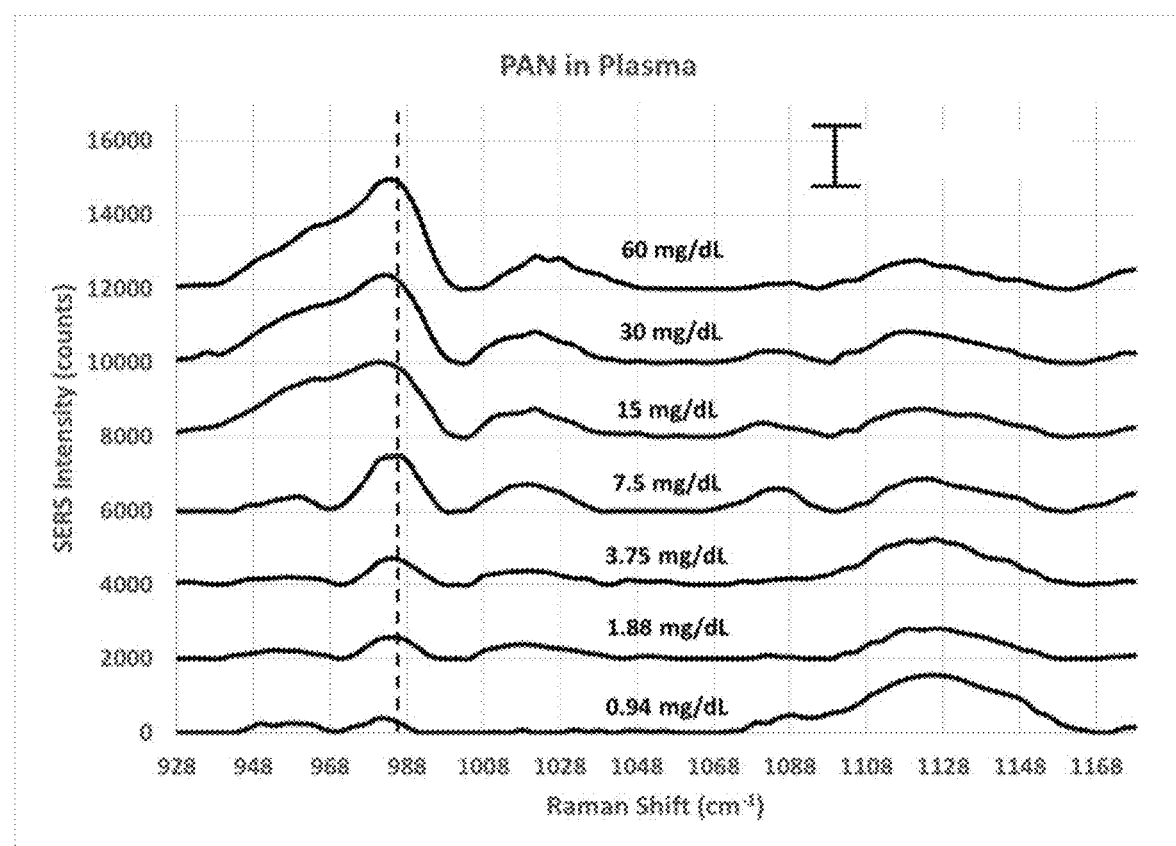
FIG. 2 shows that SERS was performed for phenylalanine in plasma at varying concentrations.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether it is highlighted. It will be appreciated that the same thing can be said in more than one way. Consequently, alternative language and synonyms may be used for any one or more of the terms discussed herein, nor is any special significance to be placed upon whether a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of "a", "an", and "the" includes plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising", or "includes" and/or "including", or "has" and/or "having", or "carry" and/or "carrying", or "contain" and/or "containing", or "involve" and/or "involving", "characterized by", and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in the disclosure, the phrase "at least one of A, B, and C" should be construed to mean a logical (A or B or C), using a non-exclusive logical OR. As used herein, the term "and/or" includes any and all combinations of one or more of the associated listed items.

As used in the disclosure, the term "biological sample" refers to a sample obtained from a biological subject, including sample of biological tissue or fluid origin obtained in vivo or in vitro. Such samples may be, but are not limited to, tissues, fractions, and cells isolated from plants, microbials, and animals including, humans.

As used in the disclosure, the term "non-biological sample" refers to a sample obtained from a subject which is not a living creature. Such samples may be, but are not limited to, earth, water, air, and human-made products, e.g. foods, drinks, construction materials, paints, and etc.

Present system described herein features a portable or handheld phenylalanine (Phe) measuring device coupled with highly sensitive blood testing substrates, offering a point-of-care solution for PKU patients to measure Phe concentration levels in their blood. In terms of detection of biomolecules, Raman scattering spectroscopy is cost effective and requires minimal sample preparation steps for analysis. Raman bioanalysis of whole blood requires using additional enhancement effects to improve the scattering cross-section and to reduce instrumental costs. The many advantages of Raman spectroscopy make it a promising biosensing tool, but molecular detection also depends on the sensitivity of the sample substrate and the detection optics of the spectrometer. To this end, the present invention develops and optimizes a handheld Phe measuring device based on single-point Raman detection, surface enhanced Raman scattering (SERS) spectroscopy, and disposable nanoporous anodic alumina substrates for at-home blood Phe testing.

The portable or handheld device of the present invention includes a nanoporous anodic aluminum oxide (NAAO) substrate. In one embodiment, the NAAO substrate has a multilayer structure. In one embodiment, the NAAO substrate has a nanoporous alumina layer laid on top of an aluminum layer base. Within the nanoporous alumina layer, there are arrays of nanopores providing reflective alumina nanocavity. In one embodiment, the NAAO substrate is layered with gold nanoparticles. In one embodiment, using the device incorporating the NAAO substrate based on the SERS technology enables the user to measure Phe in a biological sample, e.g., blood. In another embodiment, the device incorporating the NAAO substrate based on the SERS technology enables the user to measure other biomarkers in biological samples.

In one embodiment, the biological samples are in a solution form. For example, the biological samples may include blood, saliva, urine, tissue fluid, cerebrospinal fluids, and etc. In another embodiment, the biological samples which are not in the solution form can be processed into solution form before the biomarkers in the biological samples are measured by the device of the present invention.

In one embodiment, incorporating the NAAO substrate based on the SERS technology of the present invention measures biomarkers of diseases including dementia, cancers, heart diseases, neuromuscular disorders, and etc.

In one embodiment, the dementia includes Alzheimer's disease, vascular dementia, Lewy body dementia, Frontotemporal dementia, and etc.

In one embodiment, the biomarkers of dementia which can be measured by the present invention include β-amyloid peptides, Tau peptides, p-Tau peptides, RAB7A peptides, NPC2(Niemann-Pick disease, type C2) peptides, TGFB1 (transforming growth factor beta 1) peptides, GAP43 (growth associated protein 43)peptides, ARSB (arylsulfatase B) peptides, PER1 (period circadian clock 1) peptides, GUSB (β-glucuronidase) peptides, MAPT (microtubule associated protein tau) peptides, FCGR1A (Fc fragment of IgG, high affinity Ia, receptor (CD64)) peptides, UBE2L3 (ubiquitin conjugating enzyme E2L 3) peptides, NKTR (natural killer cell triggering receptor) peptides, PTGS2 (prostaglandin-endoperoxide synthase 2) peptides, RGS10 (regulator of G-protein signaling 10) peptides, ITPKB (inositol-trisphosphate 3-kinase B) peptides, KIDINS220 (kinase D-interacting substrate 220 kDa) peptides, GSK3B (glycogen synthase kinase 3 beta) peptides, SERTAD3 (SERTA domain containing 3) peptides, APOE (apolipoprotein E) peptides, UBE21 (ubiquitin conjugating enzyme E2I) peptides, FOXO3 (forkhead box O3) peptides, THRA (thyroid hormone receptor, alpha) peptides, IGF1 (insulin-like growth factor 1) peptides, NPTX2 (neuronal pentraxin II) peptides, GSTM3(glutathione S-transferase mu 3) peptides, BACEI (Beta-Secretase 1) peptides, PSEN 1(presenilin 1) peptides, GFAP(glial fibrillary acidic protein) peptides, TREM2(triggering receptor expressed on myeloid cells 2) peptides, NOCT(nocturnin) peptides, CEP350 (centrosomal protein) peptides, PPP2R2B(protein phosphatase 2, regulatory subunit B, beta) peptides, NRP2(neuropilin 2) peptides, CTSS(cathepsin S) peptides, VEGFA(vascular endothelial growth factor A) peptides, and etc.

In one embodiment, the cancers include bladder cancer, colorectal cancer, breast cancer, brain tumors, leukemia, prostate cancer, bone tumor, cervical cancer, gallbladder cancer, lung cancer, liver cancer, pancreatic cancer, lymphoma, anal cancer, kidney cancer, sarcoma, skin cancer, acute myeloid leukemia, endometrial cancer, acute lymphoblastic leukemia, appendix cancer, chronic myeloid leukemia, esophageal cancer, hypopharyngeal cancer.

In one embodiment, the biomarkers of cancers which can be measured by the present invention are presented in Table 1.

In one embodiment, the biomarkers of the heart diseases which can be measured by the present invention include CRP, ST2, TNFα, GDF-15, FAS(APO-1), LP-A2, YKL-40, IL-1, osteoprotegerin, pentraxin, procalcitonin, cytokines, serine protease PR3, soluble endoglin, adiponectin, Troponin T&I, Myosin lightchain kinase I, Heart-type FA binding protein, CK MB, sFAS, HSP 60, sTRAIL, BNP, NT-proBNP, MR-proANP, SST2, GDF-15, oxidized LDL, MPO, urinary biopyrrins, urinary and plasma isoprostanes, urinary 8-hydroxyl-2'-deoxygunosine, plasma malondialdehyde, MMP-2, 3, 9, TIMP1, IL-6, collagen propeptides, N-terminal colleagen type III peptide, myostatin, syndecan-4, galectin-3, norepinephrine, renin, angiotensin II, aldosterone, arginine, vasopressin, copeptin, endothelin-1, urocortin, chromogranin A/B, MR-pro-ADM, and etc.

In one embodiment, the neuromuscular disorders includes Amyotrophic lateral sclerosis (ALS), Botulism, Congenital myasthenic syndromes, Congenital myopathies, Cramp-fasciculation syndrome, Elevated creatine kinase, Inclusion-body myositis, Lambert-Eaton syndrome, Mitochondrial myopathy, Motor neuron disease, Muscular dystrophy, Myasthenia gravis, Myotonic dystrophy, Neuromyotonia, Peripheral neuropathy, Polymyositis.

In one embodiment, the biomarkers of neuromuscular disorders which can be measured by the present invention are presented in Table 2.

In one embodiment, using the device incorporating the NAAO substrate based on the SERS technology enables the user to measure immunoglobulins in the biological samples. In one embodiment, the immunoglobulins include IgA, IgD, IgE, IgG, and IgM. In one embodiment, the IgG includes immunoglobulins induced by microbial infections.

In one embodiment, using the device incorporating the NAAO substrate based on the SERS technology enables the user to measure hormones and/or steroids in the biological samples. In one embodiment, the hormones can be measured by the device of the present application are listed in Table 5. In one embodiment, the steroids can be measured by the device of the present application are listed in Table 6.

In one embodiment, using the device incorporating the NAAO substrate based on the SERS technology enables the user to measure nutrients in the biological samples. In one embodiment, the nutrients include vitamins, minerals, protein, fats, and carbohydrates. In one embodiment, the nutrients can be measured by the device of the present invention include Vitamin A, Vitamin C, Vitamin D, Vitamin K, α-tocopherol (Vit E), Thiamin (Vit B1), Riboflavin (Vit B2), Niacin (Vit B3), Pantothenic acid (Vit B5), Vitamin B6, Biotin (Vit B7), Folate (Vit B9), Cobalamin (Vit B12), Choline, Calcium, Chloride, Chromium, Copper, Fluoride, Iodine, Iron, Magnesium, Manganese, Molybdenum, Phosphorus, Potassium, Selenium, Sodium, Zinc, and etc.

In another embodiment, using the device incorporating the NAAO substrate based on the SERS technology enables the user to measure chemicals in non-biological samples collected from foods, e.g., animal products and plant products, drinks, e.g., water, wine, milk.

In one embodiment, the chemicals which can be measured by the present invention include bisphenols, phthalates, perfluoroalkyl chemicals (PFCs), perchlorate, artificial food colors, nitrates and nitrites, polycyclic aromatic hydrocarbons (PAHs), coumarin, mercury, monosodium glutamate, butylated hydroxyanisole (BHA), benzoate (sodium benzoate and potassium benzoate), and etc.

In another embodiment, using the device incorporating the NAAO substrate based on the SERS technology enables the user to measure chemicals in non-biological samples collected from surrounding environments, e.g. soil, lakes, ocean, construction materials and etc.

In one embodiment, the chemicals which can be measured by the present invention are presented in Table 3.

In one embodiment, using the device incorporating the NAAO substrate based on the SERS technology enables the user to measure one or more amino acids in a biological sample. In one embodiment, the one or more amino acids being measured are biomarkers of medical or mental health conditions. Table 4 provides a list of amino acids and their corresponding Raman bands for being measured by the device.

Example 1

An example of the present invention is presented below, in which Phe in blood samples of PKU patients is used as a biomarker for PKU, and being measured by the device of the present invention. It should be noted that other biomarkers for other diseases can be tested using the device of the present invention with corresponding parameter settings, e.g. wavelengths of the light selectively passes through a bandpass filter of the device, without deviating from essence of the present invention.

In one embodiment, the present invention collects the SERS spectrum and measures the Phe peak intensity as a function of concentration to build a calibration curve using conventional tabletop laboratory Raman equipment. The present invention detects the Phe in plasma and in blood down to a concentration of 0.937 mg/dL and 7.5 mg/dL, respectively.

The present invention provides solutions to the following technical challenges.

I. Tailored Surface Chemistry

Success with single-point Raman highly depends on the SERS enhancement provided by the excitation properties of the nanoparticles, the interactions between Phe and the surface ligands, and the optical and mechanical properties of the nanoporous substrate. Therefore, the present invention improves the existing technologies in the following aspect:

(1). Gain tunability in the structural parameters of the nanoparticles
(2). Develop and implement ligand-exchange protocols, and
(3). Fabricate alumina substrates with an optimized surface structure and pore size.

Fabricating nanoporous alumina sample substrates and determining the best sample preparation steps for SERS detection in blood is one of the major aspects of the present invention. The general scientific approach will be based on characterization of the samples using Raman spectroscopy to determine the success of the sample substrate and preparation steps.

II. Optimized Bandpass Filter System

For the proposed single-point Raman detection method, the present invention identifies the necessary bandpass filter (s) to exclusively transmit the Phe signal to the light sensor/detector. Using wavelength filtering technology, the center wavelength of each bandpass filter is controlled by tuning the angle of incidence. For collimated input light, independently rotating the bandpass filters serves to smoothly tune the combined transmission spectrum to the energy of the Phe signal. Two filters are used by the present invention to define the short- and long-wavelength edges of the overall transmission curve. Using this filter system, the device is tailored for detection of only phenylalanine and appropriate fixed filters chosen.

III. Device Miniaturization

The present invention also miniaturizes the single-point Raman spectrometer while keeping the device cost effective and easy to use. The dimensions of the laser, optoelectronics, and light sensor/detector are reduced to a compact size of the device, but remain reliable, accurate, and sensitive. The design of the present invention meets the demands of higher data acquisition and efficient power distribution.

IV. Validation Parameters

A. Selectivity: Due to spectral interference, the present invention determines the ability of the device to quantify Phe in the presence of other substances. This requires the collection of the SERS spectrum of the samples' known contributions: Phe, nanoparticles, plasma, and whole blood.

B. Limit of Detection (LOD): The LOD is determined as the lowest Phe concentration that can be distinguished from the background noise in the SERS spectrum. The LOD depends on Phe signal in plasma and whole blood.

C. Precision: A series of repeatability measurements are conducted, under the same experimental conditions, to determine a relative standard deviation for the method, the present invention determines the precision at different concentrations within the working range.

D. Working Range: The present invention determines the linear response range for Phe in plasma and whole blood. The acceptance criteria involves a Goodness of Fit test. A high correlation coefficient (r) is defined as 0.99.

E. Accuracy: The accuracy of the method should be measured against an accepted reference value or "true value". For Phe, the accuracy is defined by the comparison between this device and the clinical lab methods mentioned above.

Stability: The stability of Phe in blood-related samples is affected by the laser power density. The Phe peak intensity in the SERS spectrum can be measured as a function of time to characterize the extent of Phe stability.

In one embodiment, the handheld blood Phe measuring device of the present invention is based on surface enhanced Raman scattering spectroscopy, nanoporous anodic alumina (NAAO) test substrates, and single-point Raman detection. A single-point Raman blood measuring device would benefit the PKU community by being convenient to use, provide rapid test results, less expensive, and only requiring microliter amounts of blood for sample analysis. Innovation lies in the utilization of a dramatic enhancement effect achieved using resonant plasmonic excitation and, more importantly, metallic nanocavities for entrapping Phe and amplifying the scattered light. In fact, it is these enhancement mechanisms which make development of the single-point Raman device a viable solution for PKU patients.

The present invention discloses, among other things, the following:
(1). Design and implement nanoparticle synthesis and NAAO fabrication protocols which are tailored to the amplification of the Phe signal.
(2). Perform a proof-of-concept using a desktop Raman system and identify the limit-of-detection.
(3). Identify the specific wavelength needed to detect Phe in blood.
(4). Develop a prototype instrument that demonstrates that the technique is feasible.

Technical and commercial feasibility depends on identifying the sensitivity limits, the detectable range of concentrations, and creating an instrument at a price point that is acceptable to the marketplace.

Example 1—Detection of Phenylalanine in Blood Plasma in Handheld SERS Device

SERS-sensing using spherical gold nanoparticles (SNPs) and metalized nanoporous substrates was carried out for the trace detection of phenylalanine (Phe) dispersed in blood plasma and whole blood. The present invention incorporates fabricated nanoporous anodic aluminum oxide substrates (NAAOs). Nanoporous alumina substrates has a high surface area to volume ratio, thermal and chemical stability, and biocompatibility to make it a promising SERS platform. Chemistry at the self-organized and unique pore structures further enhances the SERS signal and size selection capabilities. In one embodiment of the present invention, a limit-of-detection study was performed for Phe in plasma and whole blood on NAAO substrates having an approximate 80 nm pore diameter. By incorporating this substrate, Phe can now be detected in plasma and blood to a concentration of 0.937 mg/dL and 7.5 mg/dL, respectively, without raster scanning capabilities. Improvements to the specifications of the substrate, the nanoparticle structure, and the detection parameters are also discussed.

Nanoporous Anodic Aluminum Oxide (NAAO) SERS Substrates

Anodic aluminum oxide substrates were prepared for the chemical sensing of Phe in plasma and whole blood. The NAAOs were fabricated using an electrochemical method where self-ordered nanopores growth occurs upon the anodic oxidation of pure aluminum. NAAO substrates have a high surface area to volume ratio which enhances the optical signal of Phe as it interacts with the walls of the pore channels. Additional properties of NAAOs that are important to the detection of Phe include their chemical resistance, thermal stability for increased laser power and their durability that makes for a robust substrate. NAAOs were characterized by collecting the visible reflectance spectrum for the substrate before and after anodization, as shown in FIG. 1A. The NAAOs were also characterized using scanning electron microscopy (SEM) imaging to determine the uniformity and the average pore dimensions, as shown in FIG. 1B. In addition, FIG. 1C shows a cross-sectional view SEM image of NAAO substrate.

The reflectivity of pure aluminum substrates and NAAO substrates were measured to gain insight into the success of pore formation at the surface. For the reflectance measurements, a halogen light source was guided to the aluminum surface using a visible-NIR reflectance/backscatter probe. The reflected light was collected with the same probe and delivered to a Flame spectrometer operating with a 300 µs integration time and a boxcar width of 5. To determine the ratio of reflected light to the incident light spectrum, an aluminum reflectance standard was used.

In addition to higher reflectance percentage, the spectrum for the NAAO has very clear oscillations that begin in the visible and into the NIR. The specular reflectance spectrum observed for the NAAO is attributed to the pore size and internal pore structure.

As shown in FIG. 1A, the reflectance spectrum for the porous NAAO reflects almost 20% more of the incident light than the nonporous aluminum surface. In addition to higher reflectance percentage, the spectrum for the NAAO has very clear oscillations that begin in the visible and into the NIR. The specular reflectance spectrum observed for the NAAO is attributed to the pore size and internal pore structure.

The present invention discloses that the NAAOs are a very promising SERS substrate for Phe detection in plasma. The robustness of the substrate allows higher laser powers, and the porous structure enhances the SERS signal. Using spectral reflectance analysis, one can readily identify a nanoporous surface after fabrication.

Detection of Phenylalanine in Blood Plasma on NAAOs

For the SERS measurements, the sample preparation was optimized to allow for the detection of Phe in plasma at varying concentrations (60, 30, 15, 7.5, 3.75, 1.875, and 0.937 mg/dL). To obtain a significant signal, the addition of ingredients in the SERS solution were specifically ordered. First, 20 µL of solid gold nanoparticle concentrate (SNP) was pipetted into a glass vial, followed by the careful addition of 0.6 µL 20 mM NaCl. The SNP-NaCl solution remained unmixed until right before the addition of 20 µL Phe-spiked plasma solution to the vial. Before adding the Phe-plasma solution, aggregation was confirmed by gently mixing SNP-NaCl solution until it turned greyish purple in color. The solution was gently mixed again following the addition of Phe-plasma before 5 µL was pipetted onto the substrate. Once the sample was loaded onto the NAAO, the measurement was taken immediately while the solution was still wet.

By following this sample preparation, the nanoparticles were aggregated immediately before the addition of the Phe solution which ensured molecular adsorption to the surface and hot spots of the nanoparticles. When NaCl is added and mixed after the addition of the Phe-plasma to SNP concentrate, the solution color remains dark purple, and the Phe cannot be detected.

Following specific steps for sample preparation is important to the detection of Phe in blood plasma or blood. Ensuring that the SNPs are aggregated before adding plasma increases the probability of detection. When compared to dry sampling, measuring a wet plasma/blood sample reduced the overall experimental time while maintaining the same (or greater) signal-to-noise.

As reflected in FIG. 2, SERS was performed for phenylalanine in plasma at varying concentrations. The Phe peak is located at 987 $cm^{-1}$ which is close to the ~1000 $cm^{-1}$ assignment. The intensity at 987 $cm^{-1}$ was used to detect changing levels of Phe in plasma.

As expected, the intensity of the peak increases as the concentration of phenylalanine increases. In the lower concentration range, the signal has a different spectral shape than the intensity collected at higher concentrations. The Phe peak has multiple contributions, and it is likely that a specific mode becomes less of a contribution to the overall signal at ~1000 $cm^{-1}$ as the concentration is lowered.

The position of the observed vibrational peaks is going to be influenced by the local molecular environment such as the surrounding medium and interactions amongst functional groups. The positions of spectral peaks are also sensitive to the calibration of the spectrometer and with the spectrometer Phe appears at 987 $cm^{-1}$.

Figure 3:
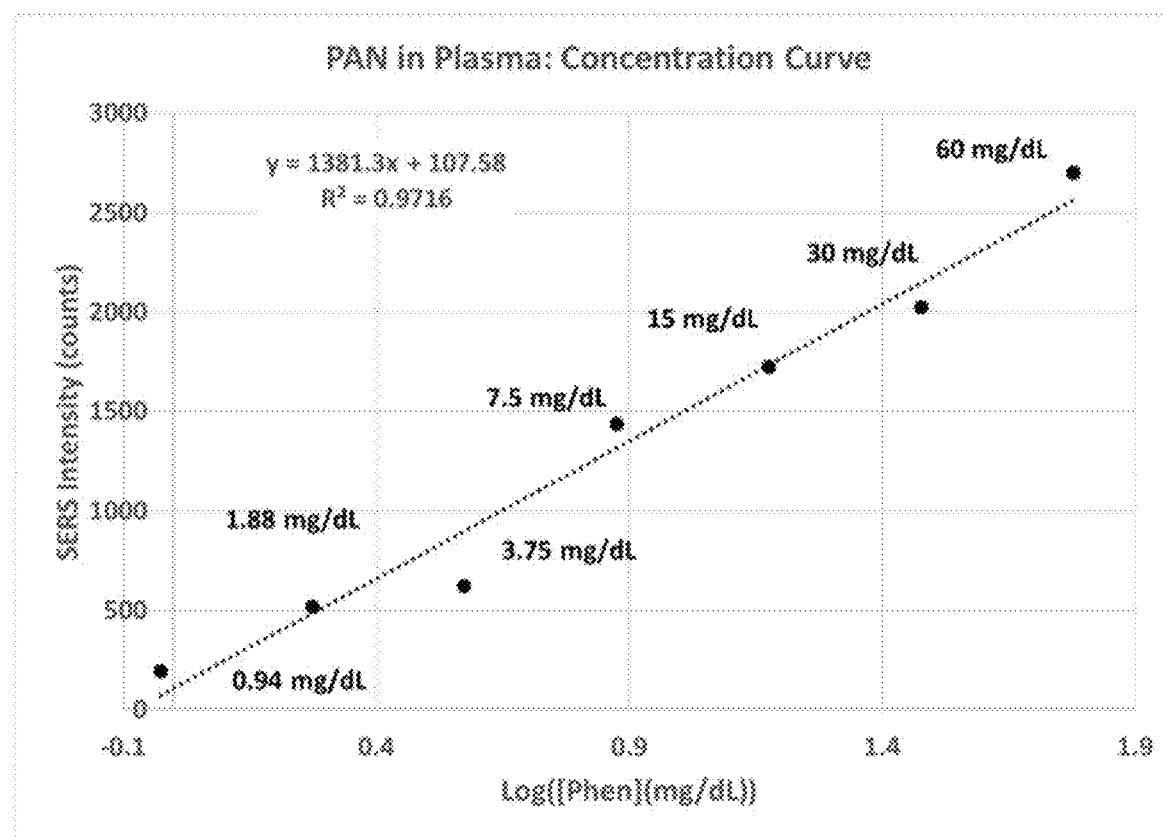
FIG. 3 shows a calibration curve was plotted to further examine detection ability of Phe-NAAOs over the concentrations 0.94 mg/dL-60 mg/dL.

In FIG. 3, a calibration curve was plotted to further examine detection ability of Phe-NAAOs over the concentrations 0.94 mg/dL-60 mg/dL. The plasma concentration range is best fit with a linear function resulting in a coefficient of determination, R2=0.9716. A limit-of-detection (LOD) was determined to be 0.94 mg/dL. For concentrations lower than 0.94 mg/dL the Phe peak did not follow the linear relationship on the calibration plot. Currently, there is no clear relationship between the SERS intensity and the low concentration range. This highlights an effect at low concentrations (<0.94 mg/dL) which may be overcome with changes in the nanoparticle structure (e.g., nanorods, spiked spheres) and the dimensions of the pores, both of which can be tailored for the Phe-NAAO system. A linear calibration curve was determined for the phenylalanine concentration range 0.94 mg/dL-60 mg/dL. Phenylalanine can be detected in plasma down to the concentration of 0.94 mg/dL. At this low concentration, a good signal-to-noise of 3 can be achieved.

Figure 4:
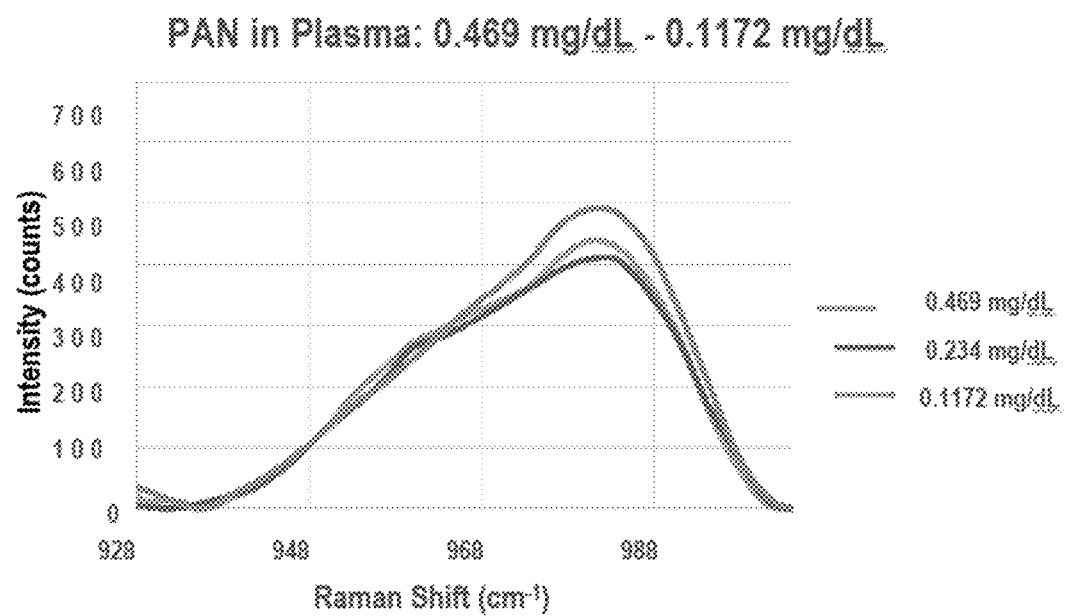
FIG. 4 depicts that SERS was performed for phenylalanine in plasma at concentrations 0.117, 0.234, and 0.469 mg/dL.

As shown in FIG. 4, SERS was performed for phenylalanine in plasma at concentrations 0.117, 0.234, and 0.469 mg/dL. For this concentration range, the Phe peak did not follow the linear relationship on the calibration plot. In this plot the lowest concentration of 0.1172 mg/dL has the highest SERS intensity. Therefore, there is no clear relationship between the SERS intensity and the above low concentration range.

Figure 5:
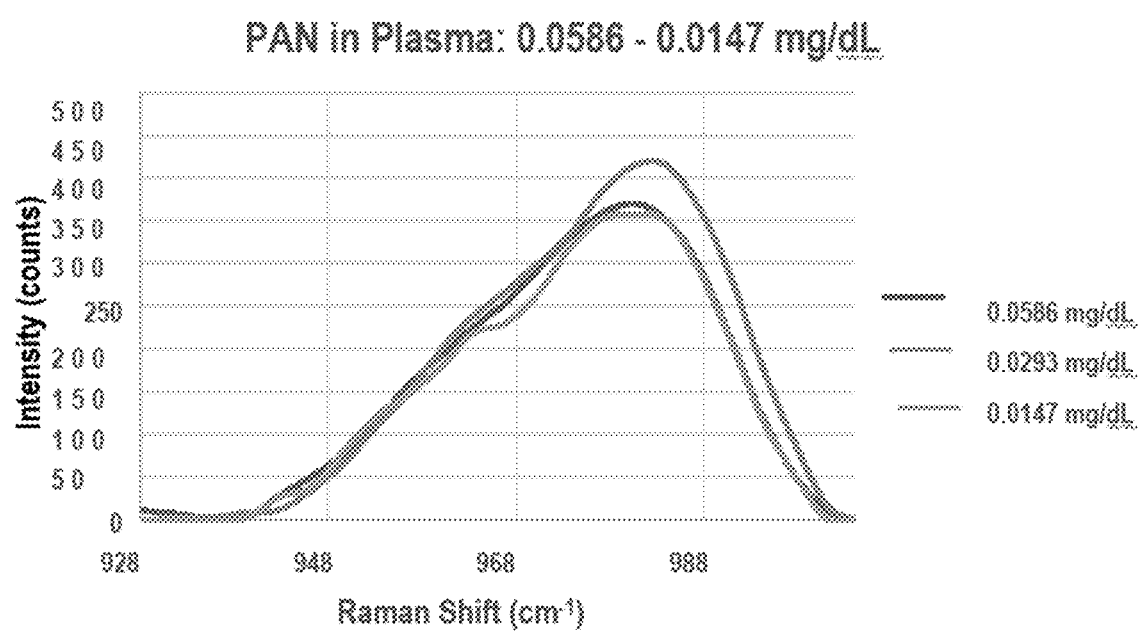
FIG. 5 depicts an effect similar to FIG. 4 occurs for the lower concentration range, 0.0586-0.0147 mg/dL.

FIG. 5 shows that a similar effect occurs for the lower concentration range, 0.0586-0.0147 mg/dL, where the Phe peak did not follow the linear relationship and there is no clear relationship between the SERS intensity and the concentration.

This highlights an effect at low concentrations (<0.94 mg/dL) which may be overcome with changes in the nanoparticle structure (e.g., nanorods, spiked spheres) and the dimensions of the pores, both of which can be tailored for the Phe-NAAO system.

Detection of Phenylalanine in Whole Blood on NAAOs

SERS measurements in whole blood requires the same sample preparation steps that were carried out for the plasma studies. Due to higher viscosities than water, blood and plasma samples require careful mixing to allow full dispersion.

Before adding the PHE-blood solution, aggregation was confirmed by gently mixing SNP-NaCl solution until it turned greyish purple in color. The solution was gently mixed again following the addition of Phe before 5 µL was pipetted onto the substrate. Once the sample was loaded onto the NAAO, the measurement was taken immediately while the solution was still wet.

It is important to properly mix the SERS solution with the patients' blood sample due to the high viscosity of blood.

Figure 6:
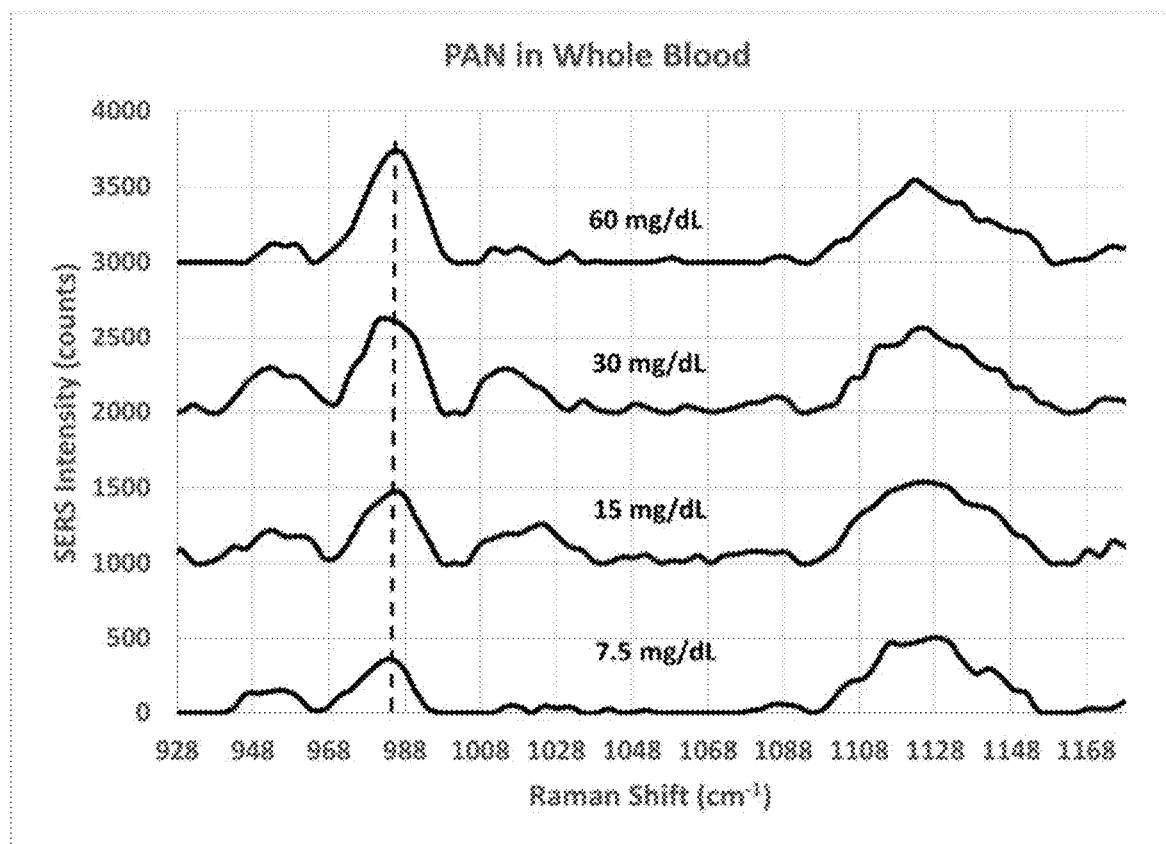
FIG. 6 depicts that SERS was performed for phenylalanine in blood at concentrations 7.5, 15, 30, and 60 mg/dL.

As shown in FIG. 6, SERS was performed for phenylalanine in blood at concentrations 7.5, 15, 30, and 60 mg/dL. Here, Phe can be detected in blood down to 7.5 mg/dL unlike the lower LOD of 0.94 mg/dL achieved in the plasma samples. The present invention attributes the different detection levels in blood to the large difference in absorption cross sections and the high refractive index of red blood cells (RBCs). The absorption and the scattering coefficient of the RBCs are two to three orders of magnitude larger than those of plasma, therefore trace detection becomes inherently more difficult. This can be overcome by further enhancing the phenylalanine Raman signal with improvements to the structures of the SNPs and the NAAOs.

Figure 7:
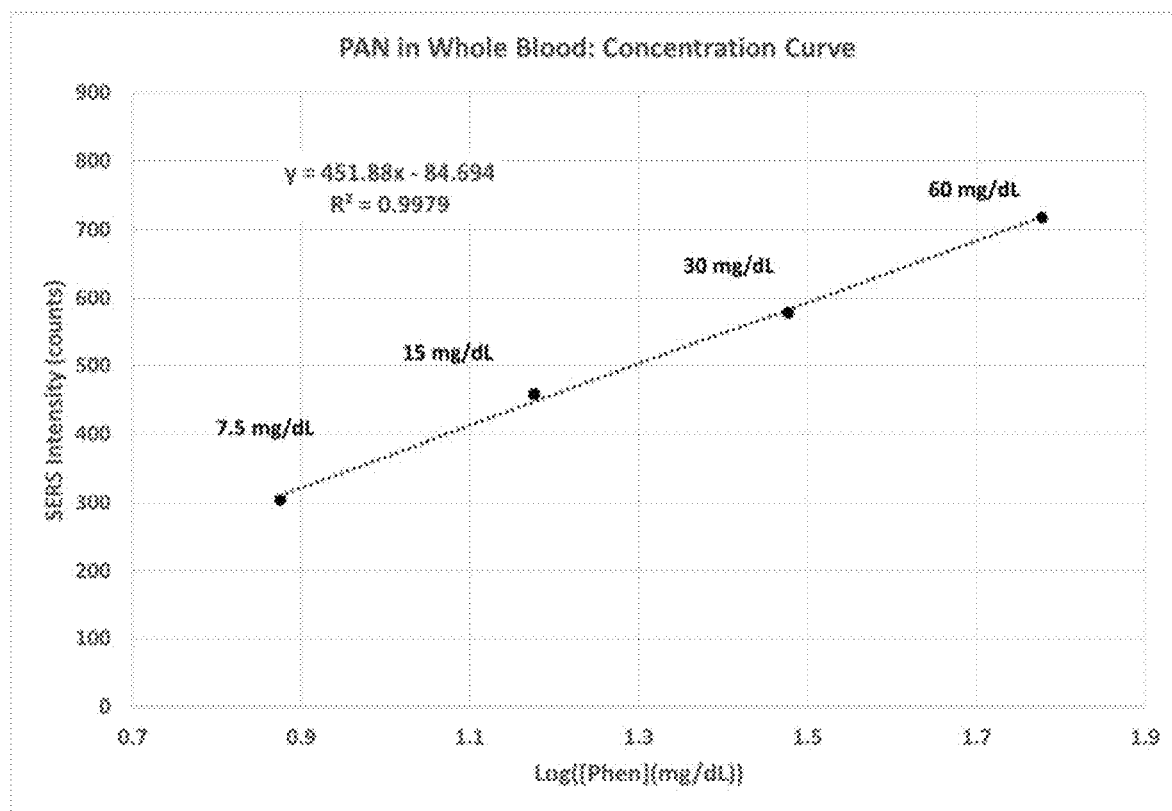
FIG. 7 shows that the calibration curve was obtained by plotting the SERS peak intensity at 987 cm−1 as a function of the logarithmic concentration of Phe.

According to FIG. 7, the blood concentration range is best fit with a linear function resulting in a coefficient of determination, R2=0.9979. A linear calibration curve was determined for phenylalanine in blood over the concentration range 7.5 mg/dL-60 mg/dL. Phe is detected in blood down to a concentration of 7.5 mg/dL, unlike the lower concentration detected in plasma. SERS spectra were also collected for Phe at concentrations 0.469, 0.937, 1.785, and 3.75 mg/dL. The 7.5 mg/dL sample shares a similar SERS response with the 3.75 mg/dL sample despite having a higher concentration. The similar SERS response is also shared by the 1.875 mg/dL sample and the 0.937 mg/dL sample, where the signals are comparable but with the lower concentration having a slightly higher intensity. The sample with the lowest concentration is almost double the counts collected for the 7.5 mg/dl sample.

Figure 8:
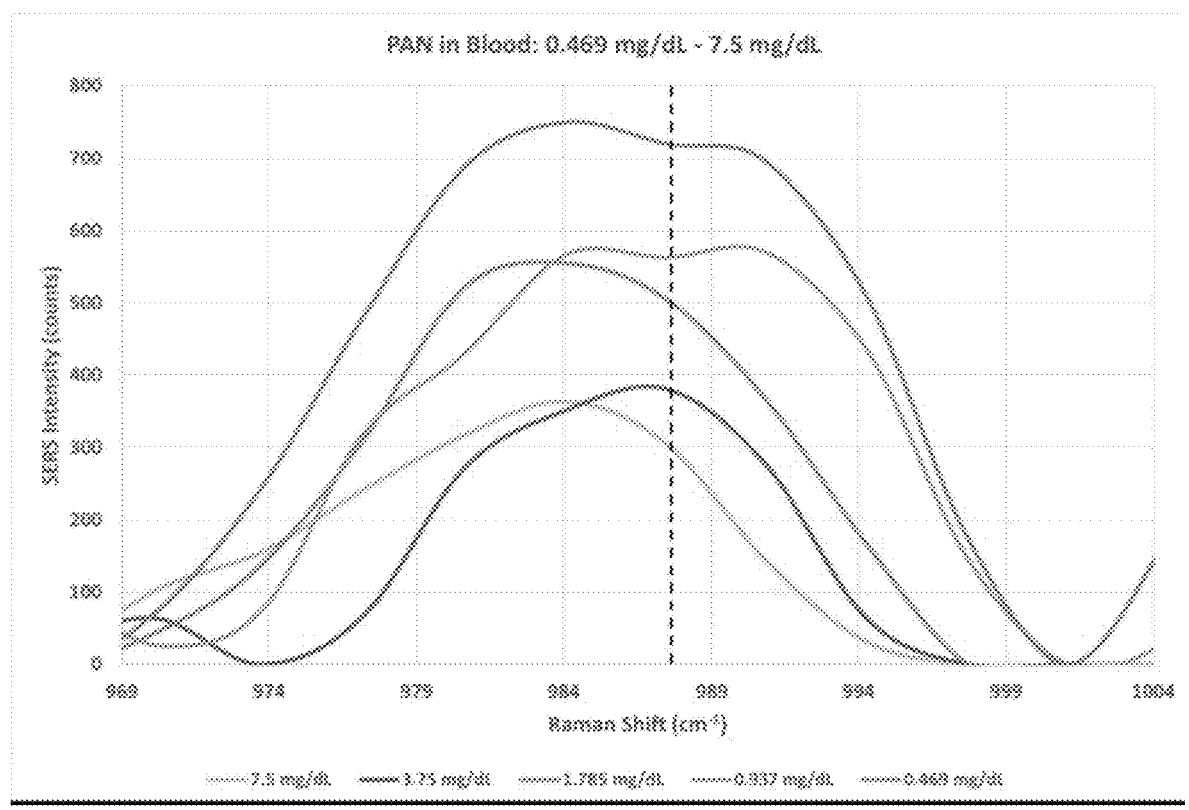
FIG. 8 shows that the SERS spectra were also collected for Phe at concentrations 0.469, 0.937, 1.785, and 3.75 mg/dL.

According to FIG. 8, SERS spectra were also collected for Phe at concentrations 0.469, 0.937, 1.785, and 3.75 mg/dL. The 7.5 mg/dL sample shares a similar SERS response with the 3.75 mg/dL sample despite having a higher concentration. This is also the case for the 1.875 mg/dL sample and the 0.937 mg/dL sample, where the signals are comparable but with the lower concentration having a slightly higher intensity. The sample with the lowest concentration is almost double the counts collected for the 7.5 mg/dL sample. The intensity at 987 $cm^{-1}$ was closely monitored by measuring the peak intensity with respect to the concentration and plotting these values.

Figure 9:
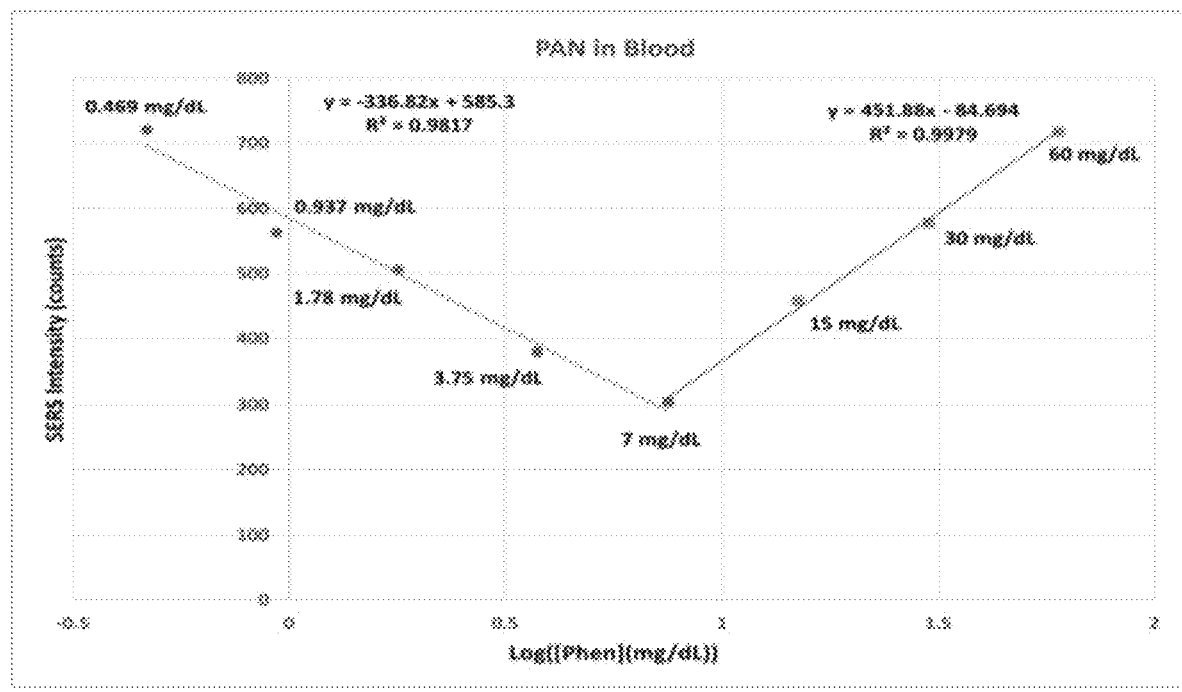
FIG. 9 shows that, in the SERS intensity of Phe in blood, the peak intensities at lower concentrations (blue circles) do not follow the same trend as the higher concentration samples orange squares).

According to FIG. 9, the intensity at 987 $cm^{-1}$ was closely monitored by measuring the peak intensity with respect to the concentration and plotting these values. The peak intensities at lower concentrations (blue circles) do not follow the same trend as the higher concentration samples (orange squares). In fact, the SERS intensity linearly increases with decreasing concentrations. When a linear fit is applied to the lower concentration regime, a systematic effect is occurring. This effect at low concentrations of Phe is likely due to changes in the Phe adsorption coverage on the nanoparticle. The increase is likely due to another mode, such as phenylalanine isomer, tyrosine, that is prone to build up in this concentration range and with the current collection parameters. To uncover and separate these two effects in blood, the Phe signal needs further enhancement. The collection parameters and laser power can also be optimized to detect Phe in blood under 7.5 mg/dL. In addition to instrumental changes, the structure of the nanoparticle can also aid in furthering the enhancement. Along with the spherical nanoparticles, gold nanorods were prepared and substituted in this system to aid with Phe detection.

In the present invention, all of the measurements made to date were done using a conventional desk-top Raman system, which is effective but costly. To make a cost-effective solution, the instrumentation must be simplified considerably.

As already demonstrated in FIGS. 2 and 6, the signal from phenylalanine predominantly affects only a small portion of the Raman spectrum. Therefore, rather than collecting the whole Raman spectrum each time, with the associated complex instrumentation required for such a measurement, in one embodiment, the present invention focuses on the exact part of the spectrum associated with the phenylalanine signal and collects only the signal generated at that wavelength or potentially group of wavelengths and completely disregarding the rest of the spectrum. It then becomes possible to dramatically simplify the instrumentation eliminating the need for a grating and an area detector in favor of some simple filters, lenses and a low-cost single photodiode detector.

Early tests have demonstrated that the best results were obtained by scanning the laser over a larger area of the sample, which again is not possible in a simple handheld instrument due to cost considerations. The present invention, in one embodiment, uses a cylinder lens as the focusing lens to create a line rather than a spot covering a larger area of the sample. This may however reduce the power of the laser at any given point enough to have a counterproductive effect. The present invention establishes a functional model of this approach, as well as optimizing the laser line width and length. The optimization of the sample signal using the improved substrate detailed above is also instrumental to making this approach possible.

Figure 10:
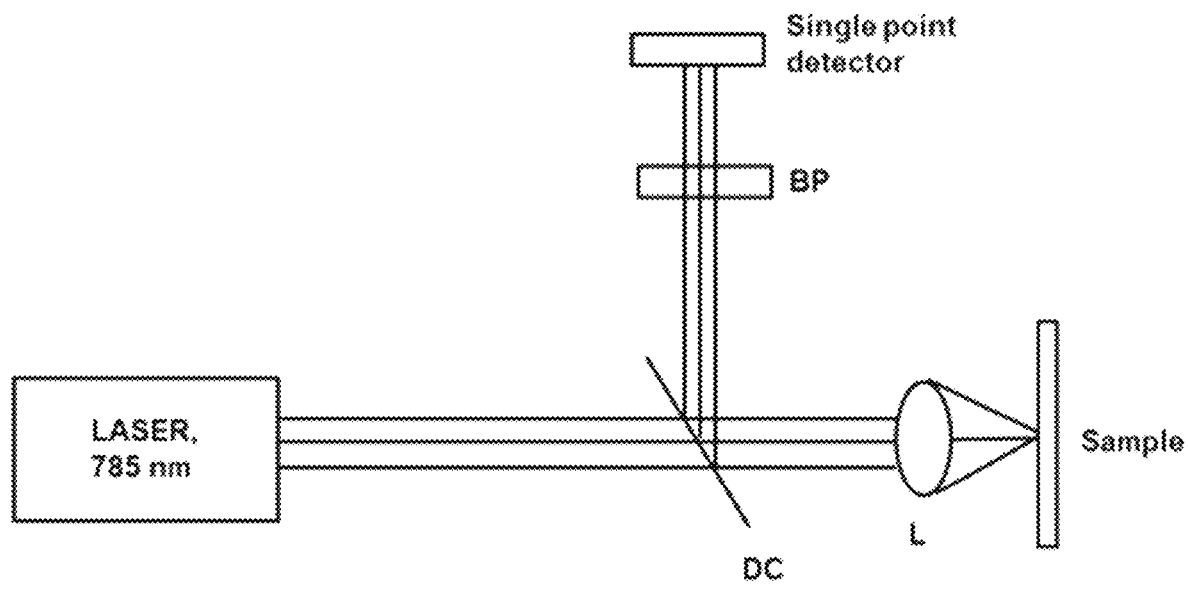
FIG. 10 shows single-point Raman initial test schematics.
Figure 10:
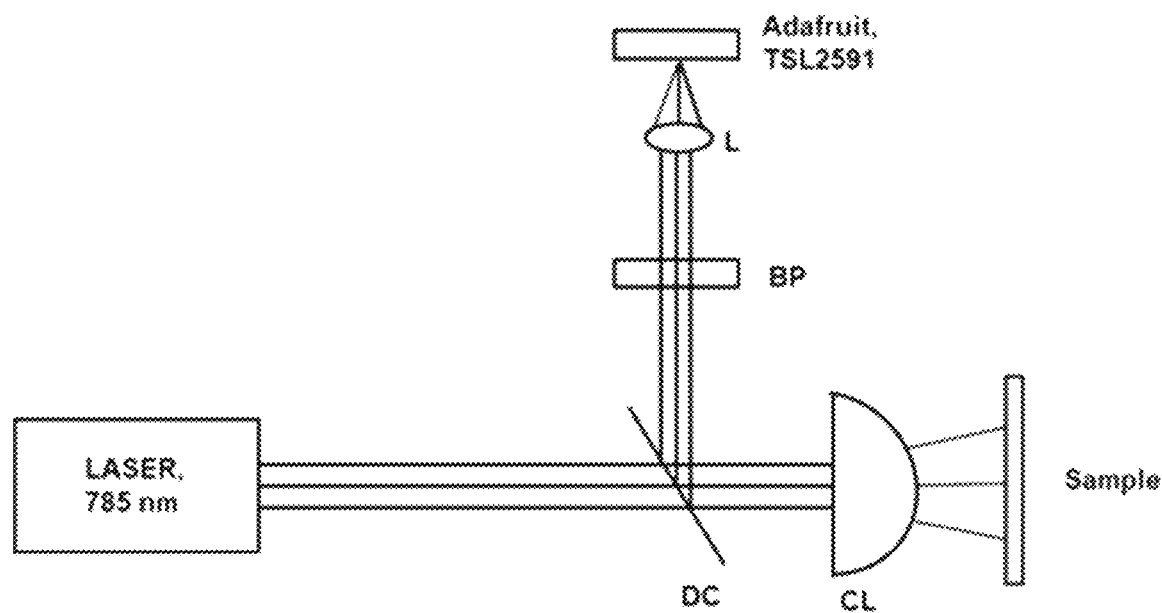

To aid in the development of the final system, a more complicated alternative system has been developed. As shown in FIG. 10, by using two variable bandpass filters to create a narrow, but moveable signal window as tests is done to home in on the exact wavelength(s) required for optimal phenylalanine concentration detection. Once the optimal wavelength(s) is determined, the variable filters can be replaced with fixed narrowband pass filters as mentioned above.

In one illustrative embodiment, CTAB-NRs were prepared using a seeded-growth method. NIR plasmon peak generated at 800 nm ($\lambda exc=785$ nm). Ligand exchange is required for successful Phe surface adsorption, Cit-GNRs. Centrifugation, separation and redispersion steps are being optimized for concentrate formation.

In one illustrative embodiment, Nanoparticle sensing solution is used for nanoparticle concentrate-coated NAAO. For Au NP concentrate, colloidal solution is centrifuged and separated, while for Au NP Sensing solution, there is no NaCl activation agent, less sample preparation steps. Also, there is no mixing, and the samples are directly loaded onto NAAO. Therefore, the time of measurement is reduced.

In one illustrative embodiment, the present invention discloses NIR Excitation Mode with Spherical NPs. Reflectance spectrum for SERS-NAAOs using spherical particles present absorption modes* at ~500 nm and ~900 nm. Similarly, to the nanorods absorption spectrum, spherical nanoparticles loaded onto NAAOs generate a NIR band. Spherical nanoparticles of different sizes are being tested with this method.

In one illustrative embodiment, the present invention discloses NAAO fabrication and characterization. Phenylalanine is at 60 mg/dL in water 120 mW, 5 s is used for integration. Phe signal intensity on SERS-NAAO can be ~2× that of the SERS solution. However, deposition coverage is inconsistent from chip to chip.

Example 2—Fabrication of NAAO Substrate and Test Strip

The present invention is also directed to a centimeter-scaled, gold-layered SERS-NAAO substrate scalable fabrication process based on the air-water-oil interfacial self-assembly of gold nanoparticles (NPs) into 2D arrays at the surface of a nanoporous alumina layer. It is an objective of the present invention to provide a cost-effective SERS substrate fabrication for the Raman enhanced detection of phenylalanine by combining gold nanoparticle colloidal solutions and non-lithographic (wet-chemical) protocols for preparing reflective alumina nanopores. An appropriate combination of surface structure, nanostructure morphology, and physical and chemical properties were determined for phenylalanine sensing.

The air-water-oil assembled gold nanoparticles provided localized electric fields at the interparticle gaps ("hot spots) of the nanoparticles. The concentrated electric fields would provide the enhancement to the Raman signal of phenylalanine. The alkylamine ligand implemented for the self-assembly and the size of the nanoparticles greatly contributed to the localized field, therefore also the nanoparticle-adsorbed phenylalanine Raman enhancement.

An alumina substrate surface was chosen as a promising platform for gold layering. The binding of the gold NPs onto the surface depends largely on the surface species provided by alumina. Therefore, great care has been taken in choosing a simple gold assembly method where an alkylamine-functionalized nanoparticle has favorable interactions with the hydroxyl groups at the surface of alumina. Here, strict fabrication parameters were created to form ordered nanopores, to induce an efficient in-situ ligand exchange, to create a uniform gold layer, and to preserve the integrity of the gold layer after drying, and to promote phenylalanine surface adsorption.

An ordered nanoporous alumina layer is grown atop an aluminum substrate using a scalable wet-chemical two-step anodization process. Before gold layering, the resulting NAAO structure is multilayered, $Al_2O_3/Al$.

An air-water-oil in-situ alkylamine ligand exchange, induced by a reduction in electrostatic repulsive forces, drives the self-assembly of negatively charged citrate-capped spherical NPs (~60 nm diameter). Under the same experimental parameters as the spherical morphology, positively charged CTAB-capped nanorods did not form long-range gold layers across the centimeter scale square substrate.

An efficient self-assembly of the gold NPs and detection of phenylalanine in blood was promoted by (a) concentrated aqueous spherical gold nanoparticles (~60 nm diameter) layer, (b) micromolar concentration of the alkylamine-hexane organic layer, (c) partially controlled air phase within a triple vented, lidded polystyrene container, (d) slow evaporative drying at room temperature.

Figure 35:
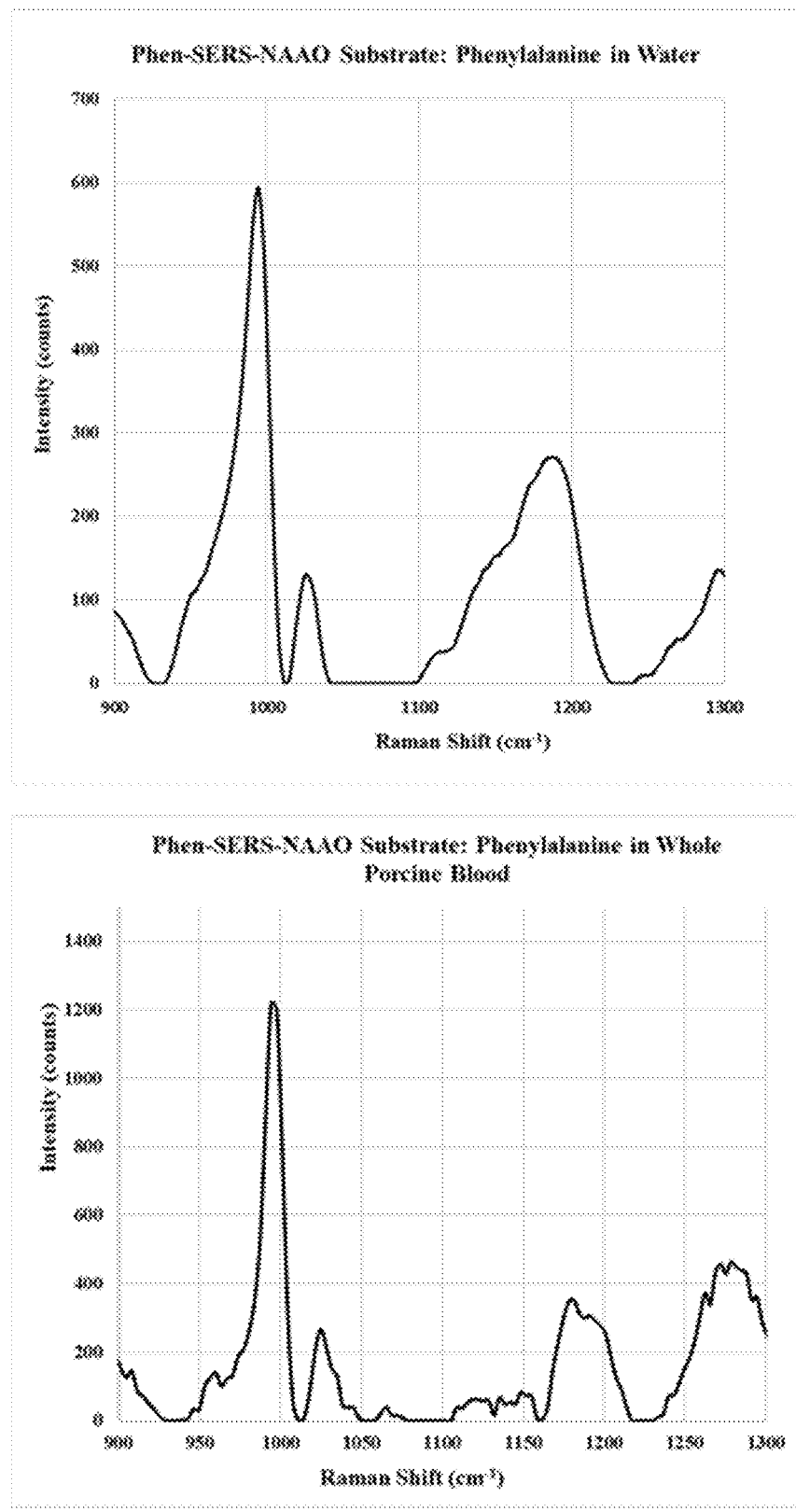
FIG. 35 upper panel shows SERS spectrum of phenylalanine in water adsorbed to the SERS-NAAO substrate, and the lower panel shows SERS spectrum of phenylalanine in whole porcine blood adsorbed onto the SERS-NAAO substrate.

FIG. 35 upper panel shows SERS spectrum of phenylalanine in water adsorbed to the SERS-NAAO substrate, and the lower panel shows SERS spectrum of phenylalanine in whole porcine blood adsorbed onto the SERS-NAAO substrate.

The Phe SERS sensing on nanoporous anodic aluminum oxide (NAAO) substrates used a mixed sample-nanoparticle test solution, which was deposited onto NAAO substrates before taking the measurement. Using this premixing procedure, a limit of detection (LOD) of Phe in plasma and blood was determined to be 0.94 mg/dL and 7.5 mg/dL, respectively. For at-home detection, a significant issue with this method is that the premixing introduces additional steps for the user, which could complicate testing and obscure the results. To confront this matter, the present invention discloses another embodiment, which discloses a low-cost, wet chemical, and scalable water/oil/air three-phase (tp) ligand exchange approach for gold layering the NAAO substrates. This approach is a thermodynamically controlled process in which a cosolvent induces the ligand exchange, phase transfer, and the self-assembly of the gold nanoparticles. The nanoparticles which were formally dispersed in the sample nanoparticle-test solution, now with the three-phase protocol, have a different ligand which promotes film formation. In this way, the premixing steps are eliminated, and the user can deposit their sample directly onto the gold-coated substrate before taking the measurement.

In one embodiment, the present invention uses a water/oil/air three-phase gold layering protocol to prepare SERS-active NAAO substrates. Fabrication steps are disclosed to highlight the synthetic parameters which must be controlled for layer formation. Qualitative data, such as videos and optical images provide first insights into the assembly of the gold nanoparticles before and after drying. Additionally, the surface optical properties of the gold coated NAAO were characterized using reflectance spectroscopy. The reflectance spectra provided insight into the coupling of the gold nanoparticles deposited at the surface and the resulting localized surface plasmon resonance (LSPR) wavelength for SERS excitation. The chemical sensing capability of the resulting three-phase SERS NAAOs were also investigated by collecting the SERS signal of the classic test molecule, Rhodamine 6G, following 785 nm excitation.

Ultimately, the SERS signal for 250 mg/dL phenylalanine in water and whole blood loaded onto a SERS-NAAO substrate were measured. The present invention shows an appreciable SERS signal when Phe was loaded onto the gold layered NAAO substrate. This was confirmation that the self-assembled nanoparticles, despite undergoing a ligand exchange to self-assemble, provided concentrated electromagnetic fields for the SERS sensing of phenylalanine. SERS experiments were conducted at multiple points across a 10×10 mm substrate to determine an overall signal uniformity error of ~20% for the current fabrication protocol.

Fabrication of SERS-NAAO Substrates: Three-Phase Gold Layering

Fabrication of SERS-NAAO substrates is based on a low-cost wet chemical approach to develop gold layers directly onto substrates. A three-phase system comprised of air/water/hexane interfaces promotes the self-assembly and migration of gold nanoparticles into a two-dimensional thin film structure upon the addition of a cosolvent. The formation mechanism involves injecting ethanol at the water/hexane interface, which induces the gold nanoparticles to diffuse to this interface where an in-situ ligand exchange passivation temporarily traps the nanoparticles. Next, the ligand-exchanged nanoparticles migrate to the air/water interface, where they self-assemble to form a gold monolayer on top of the NAAO substrate. The new ligand helps reduce the electrostatic repulsion, by controlling the interparticle separation between the nanoparticles, therefore causing the formation of gold layer.

First, for a laser-cut 10×10 mm (4×4, 5×5, and 7×7 mm SERS-NAAO available) NAAO substrate, the aqueous nanoparticle layer was established by pipetting 80 µL of the concentrate onto a single NAAO substrate which was placed in a disposable petri dish. If more than one substrate was processed in the same dish, they were sufficiently separated to prevent interfering layer formation. After depositing the concentrate, milliliter amounts of a long-chain amine doped hexane (uM) solution were slowly added to the petri dish to submerge a portion of the concentrate droplet, but allow the droplet to protrude forming an air/water/hexane interface. As shown in FIG. 11A-E, using a sterile syringe, microliter amounts of ethanol were injected (1 drop/min) at the water/hexane interface to induce gold layer formation. The wet substrates dried overnight before use in SERS measurements.

Figure 11A:
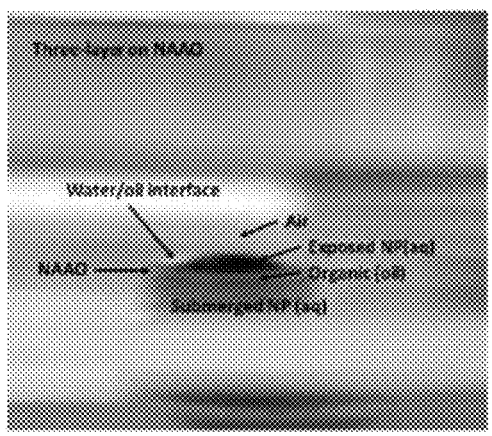
FIG. 11A shows lateral side of a three-phase assembly atop an individual NAAO in a plastic petri dish.
Figure 11B:
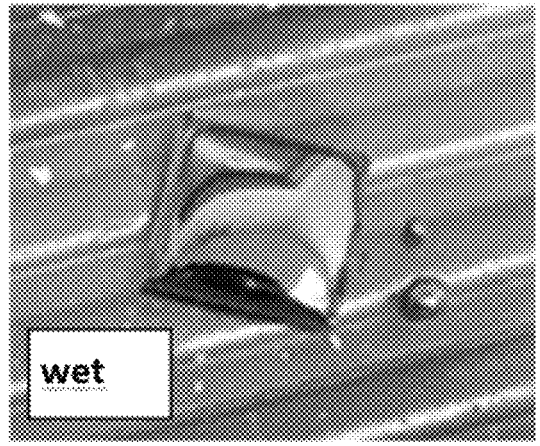
FIG. 11B shows a top view of wet assembled gold NP layer atop NAAO.
Figure 11C:
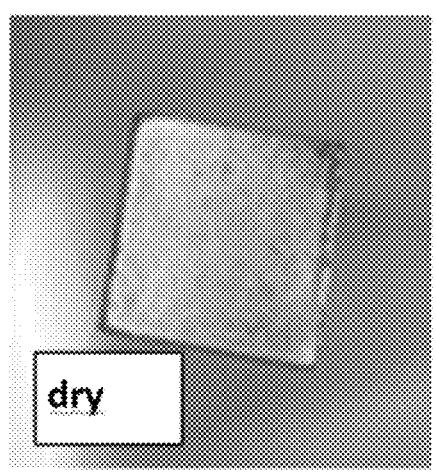
FIG. 11C shows a top view of NAAO after overnight drying.
Figure 11D:
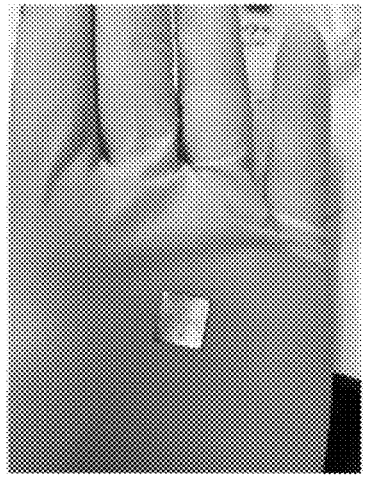
FIG. 11D shows the size of 10×10 mm SERS-NAAO relative to a human hand.
Figure 11E:
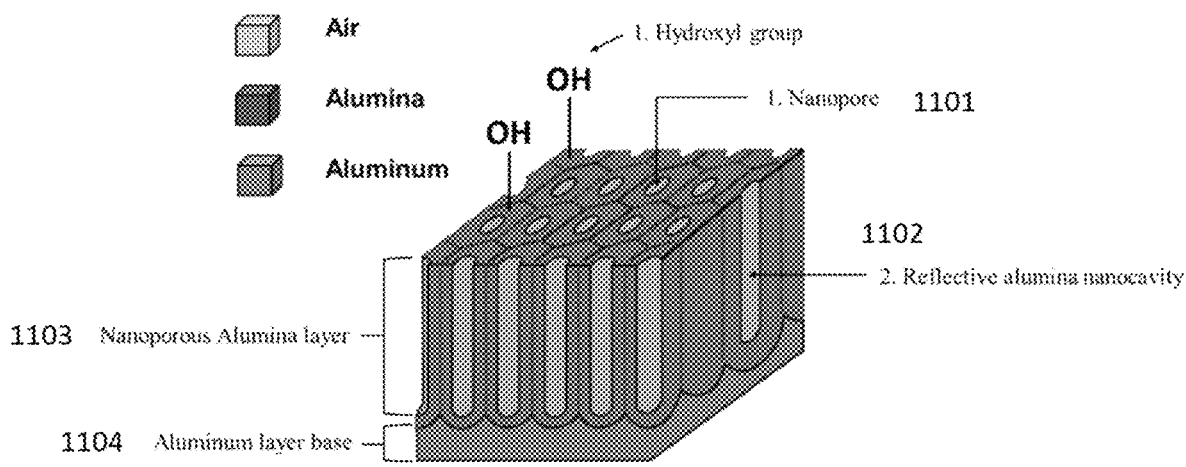
FIG. 11E shows a diagram of nanoporous anodic aluminum oxide substrate layers.

FIG. 11A shows lateral side of a three-phase assembly atop an individual NAAO in a plastic petri dish. FIG. 11B shows a top view of wet assembled gold NP layer atop NAAO, and FIG. 11C shows a top view of NAAO after overnight drying. FIG. 11D shows the size of 10×10 mm SERS-NAAO relative to a human hand. FIG. 11E shows a diagram of nanoporous anodic aluminum oxide substrate layers. In particular, the substrate has a nanoporous alumina layer 1103 laid on top of an aluminum layer base 1104. Within the nanoporous alumina layer 1103, there are arrays of nanopores 1101 providing reflective alumina nanocavity 1102.

The present invention explored different drying methods, including oven, heat gun, freezer, microwave, and cool fan, to efficiently dry the gold-coat after development. The chosen drying method had to leave the assembled film undisturbed and preserve the optical properties (reflectance) of the nanoparticles after drying. Overnight drying at room temperature is the often-used method for evaporating solvents and allowing the film to dry with extended time. This overnight drying method has proven to be the most effective for drying the SERS-NAAO. Additional studies were also carried out to reduce the drying time. For example, setting the substrates near a fume hood where air is being flushed out of the hood decreases the drying time.

Key points for fabrication process includes (1) NAAO substrates can be laser cut to various shapes and sizes; (2) gold layering is due to an in-situ ligand exchange; (3) only using overnight drying; (4) air venting being explored for faster drying.

Aqueous Phase: Gold Nanostructures

Figure 12:
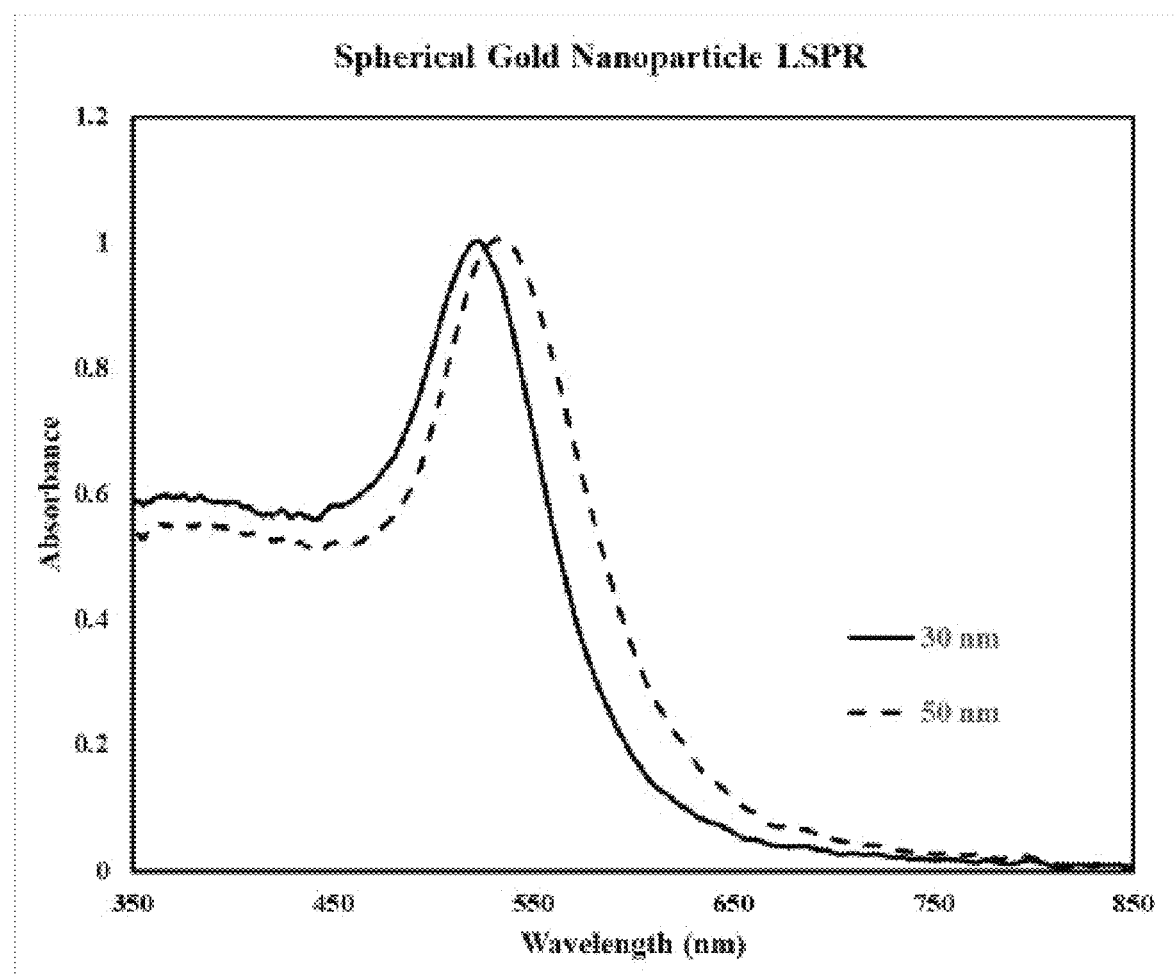
FIG. 12 shows the absorption spectrum of the as-synthesized spherical gold nanoparticle solution.

Colloidal suspensions of spherical gold nanoparticles (SGNs) were synthesized using a sodium citrate reduction method to form the aqueous nanoparticle phase. The resulting nanoparticles will be citrate capped particles stabilized in the aqueous solution. A 250 mL gold chloride solution (aq) was brought to a boil under vigorous stirring followed by a quick injection of microliter volume of sodium citrate solution. The mixture was allowed to continue boiling for 20 minutes and the final solution was placed in the fridge overnight before use. Particle size was controlled by the volume of the reducing agent administered to the gold salt solution during synthesis. As shown in FIG. 12, approximately 60 nm diameter (LSPR ~538 nm) particles were prepared according to aforementioned protocol, a size which allowed for efficient and controlled layer formation. A solution of NPs with smaller diameters were synthesized and tested for layer formation. Smaller particles (~30 nm, LSPR ~528 nm) formed fragile layers which took longer fabrication time to form and, in most cases, experienced surface cracks. The use of larger nanoparticles (>50 nm) was ruled out by the broad NP size distribution (broad LSPR peak), which would cause disorder and counter act the more controlled assembly of "like" particles.

Figure 13:
FIG. 13 shows NP Qualitative Characterization.

FIG. 12 shows the absorption spectrum of the as-synthesized spherical gold nanoparticle solution. One of the tested colloidal solutions presents an LSPR at approximate 528 nm which corresponds to an average particle diameter of approximate 30 nm. A decrease in the volume of sodium citrate solution was incorporated for the second nanoparticle solution producing an average NP diameter size and LSPR of approximate 60 nm and 538 nm, respectively. FIG. 13 shows NP qualitative characterization. A quick qualitative examination of the spherical NP solutions. Following the synthesis, the initial indication of the nanoparticle size regime is by eye. The larger of the NPs has a purple color, whereas the smaller NP regime has a redder color. In another embodiment, the current process steps are scaled up, and synthesis yields approximately 230 mL which can be doubled and result in a nanoparticle solution with the same absorption spectrum.

The chosen spherical nanoparticle solution (~60 nm diameter) was centrifuged down (4000 rpm, 25 min) to form a concentrate (2-3 mL) which was then diluted by half. The use of nanoparticle concentrates, instead of the more dilute as-synthesized solution, ensured there were a greater number of nanoparticles per unit volume to promote efficient self-assembly. Still, a diluted nanoparticle concentrate was necessary to reduce layer stacking and limit the assembly of nanoparticles into a 3D structure instead of a uniform layer, as shown in FIG. 13.

Figure 14:
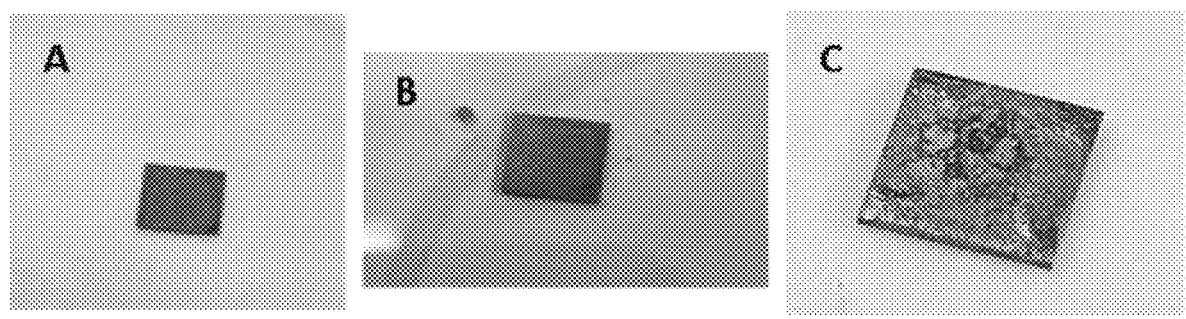
FIG. 14 shows examples of resulting NAAO substrates which had undergone coating with an undiluted concentrate solution.

FIG. 14 shows that the nanoparticle concentrate must be diluted by half. Examples of resulting NAAO substrates which had undergone coating with an undiluted concentrate solution are shown in FIG. 14. Each substrate exhibits signs of uncontrolled, multiple layer formation. The multilayer formation is clear in the alternating dark and light ring features where stacked layers are likely formed. Substrate B shows that like substrate A, the discoloration and dark spots are an indication of multilayer formation although it is less pronounced. The percentage of monolayer areas are expected to increase on B with respect to substrate A. Substrate C is an extreme case of multilayer stacking. In this case, the extent of layer stacking has created an uneven topology that can be seen clearly by eye.

Additionally, gold nanorods solutions were prepared using a seed-mediated method where a nanoparticle seed (~2 nm) serves as a nucleation center for axial growth. To prepare the gold seed solution, a 10 mL CTAB solution was prepared in a warm water bath (28° C.). Once the CTAB was dispersed and the solution turned clear, microliter volume of $HAuCl_4$ was added to the CTAB solution. Under vigorous stirring, microliter volume of ice cooled $NaBH_4$ was rapidly injected. The solution continued to stir at 28° C. for 5 minutes. The seed solution had to age for at least 1 hour before use. To prepare the nanorods, another 10 mL CTAB solution was placed in a 28° C. warm water bath and spun until the solution remained clear. Microliter volume of $HAuCl_4$ was then added to the spinning CTAB solution, followed by the addition of 50-100 µL $AgNO_3$ solution. After 1 minute, microliter volume of HCl was added. Vigorous stirring was applied to the solution before rapidly adding 80 µL of ascorbic acid. Lastly, microliter volume of the seed solution was added. The final nanorods solution was lightly stirred in the warm water bath for 30 minutes.

Unlike the spherical particles, the nanorods are passivated with a positively charged cetyltrimethyl ammonium bromide (CTAB) ligand which hinders the in-situ ligand exchange at the water/oil interface, a requirement for this assembly protocol. Layering using the current nanorods structures is unstable and requires additional ligand exchange process steps following synthesis and prior to concentrate formation, as shown in FIG. 15.

The volume of NP concentrate that was added to an individual substrate was determined for 4×4, 7×7, and 10×10 mm NAAOs. The starting concentrate volume depended on the size of the substrate in that an amount was chosen based on concentrate filling up the entire substrate.

Figure 15:
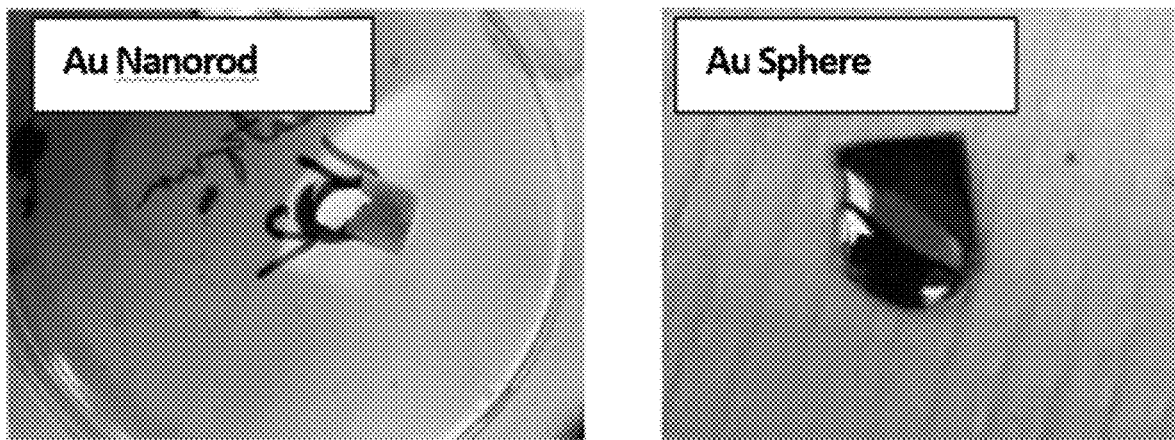
FIG. 15 shows unstable NR Layer.

FIG. 15 shows unstable NR layers. A gold nanorods layering was conducted under the same conditions as the spherical particles, but a stable well-adhered layer on top the NAAO doesn't form, as shown in the left panel. For CTAB-passivated NRs, self-assembly is slow and cracks form during solvent evaporation. This behavior was predicted to some extent when comparing the initial nanorods concentrate which was more dilute after centrifugation than the spherical concentrate, as shown in the right panel.

Key points for Aqueous Phase includes (1) approximately 60 nm spherical NPs required; (2) need to dilute NP concentrate to half for controlled layering; (3) unstable layering with CTAB-capped nanorods; (4) NRs will require ligand exchange prior to three-phase fabrication; (5) nanoparticle synthesis can be readily up scaled.

Organic (Oil) Phase: Alkylamine-Doped Hexane

The organic (oil) phase, doped with a long chain alkylamine, was prepared to create a water/oil interface for an in-situ ligand exchange and phase transfer. At the water/hexane interface, a ligand exchange takes place as the citrate ligands on the NPs are replaced by the alkylamine ligands. Dodecylamine (dd, $C12-NH_2$) was dispersed in the hexane (Hex) solvent to produce a solution which was $0.5 \times 10^{-6}$ M ddHex. This long chain amine has been shown to achieve efficient phase transfer when compared to shorter carbon chain amines. Ordered gold nanoparticle films have been successfully formed within a ddHex concentration range of $0$-$4.17 \times 10^{-4}$ M. Gold films with a greater ddHex concentration were also fabricated. Film formation proceeded faster using the greater concentrated ddHex, but the resulting film after drying was non uniform and resembled the substrates in FIG. 14, therefore unsuccessful.

One other long chain amine (an eighteen-carbon chain instead of twelve) was tested to assess any changes in the formation of the film and the resulting SERS sensing. An octadecylamine (od, $C18-NH_2$), hexane phase was prepared at the same concentration as the previous dd-Hex phase and tested for NP assembly. Assembly was successful and produced a similar layer to the ddHex-fabricated layer. Slight changes in the color (shifted LSPR wavelength) of the film were evident which was expected since the scattering wavelength strongly depends on the NP interparticle separation, which is controlled by the alkylamines. On average the band intensities did not vary from ddHex to odHex. Carbon chain length in the alkylamine is being further investigated in order to further optimize the carbon chain length in the gold layer which strongly depends on the structural properties of the nanoparticle.

Figure 16:
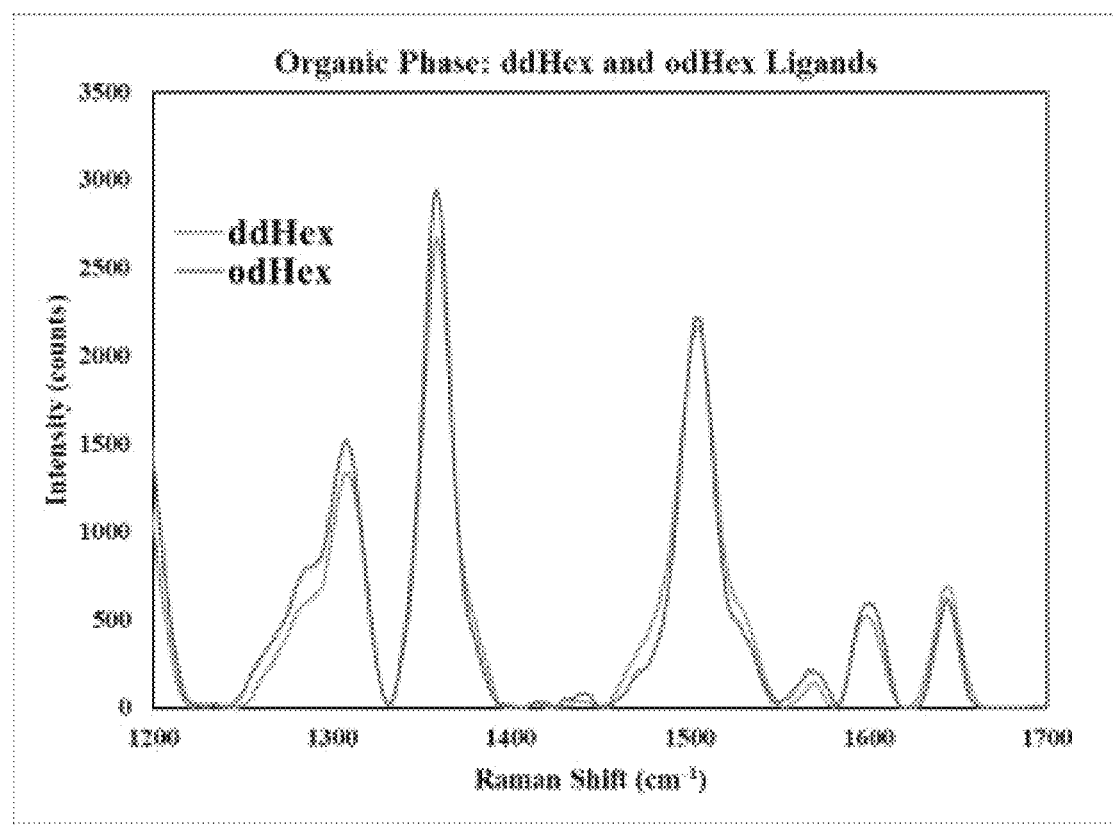
FIG. 16 shows ddHex vs odHex.

FIG. 16 shows ddHex vs odHex. The SERS spectrum for R6G loaded onto a SERS-NAAO fabricated using ddHex ($C^{12}$—$NH_2$) and one fabricated using odHex ($C^{18}$—$NH_2$). The SERS spectrum for R6G loaded onto each NAAO was collected and the two spectra share all the same bands, and the peak intensities were comparable for both systems. Although there was a shift in the optical properties of the resulting films, the R6G SERS signal for dd and od capped nanoparticles were very similar.

The volume of the organic layer necessary for successful gold layering is closely related to the volume of the assembly container. For the laser cut substrate sizes studied here, containers with a range of materials (polystyrene, glass) and volumes (4 mL-115 mL), have been tested for successful layering. These parameters have a great effect on the gold layering process because they determine the volume necessary to form three separate phases. Two different containers prove to be the best conditions for the current fabrication process. One container is a simple capped disposable petri dish with a max volume of 115 mL. The other container is a 4 mL capped glass vial. Both assembly container materials can be scaled to containers with a larger volume.

Lastly, another important impact to fabrication is the draining of the organic solution after the film has formed. The fabrication protocol described here results in two classes of SERS-NAAO. According to FIG. 14, its evident that allowing the organic solution to evaporate in a semi-controlled environment (closed petri dish) resulted in a shiny gold coat with few regions of discoloration (darker spots). When the organic solution is drained/siphoned off before placing the lid on the petri dish the coat consistently results in a darker matte coat which has obvious regions of discoloration. These two fabricated types of SERS-NAAOs are separated into classes due to their differing optical properties.

Figure 17:
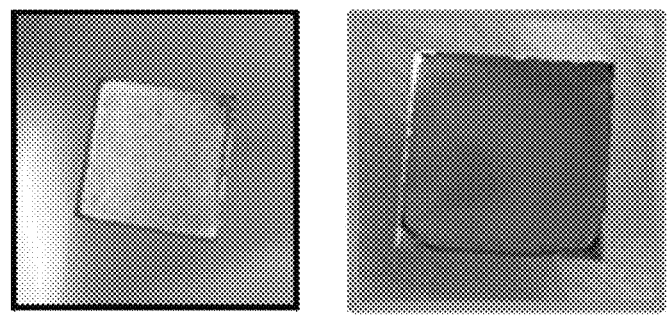
FIG. 17 shows the diagram of draining the organic layer.

FIG. 17 shows the diagram of draining the organic layer. The left panel shows Class 1 SERS-NAAO which sat in the shallow pool of organic with the lid closed while it dried; while the right panel shows Class 2 SERS-NAAO dried in a closed petri dish after the organic solution was removed after gold film was formed.

The key points for organic phase includes (1) 0.5×10–6 M dodecylamine in hexane (ddHex); (2) Continued work using long chain amines; (3) 2-5 mL of ddHex; (4) 10×10 mm substrates are processed in disposable petri dish; (5) 7×7 mm and 4×4 mm are processed in the 4 mL glass vial; (6) Container volume and material has the potential to be scaled up for larger production volumes.

Air Phase

Figure 18:
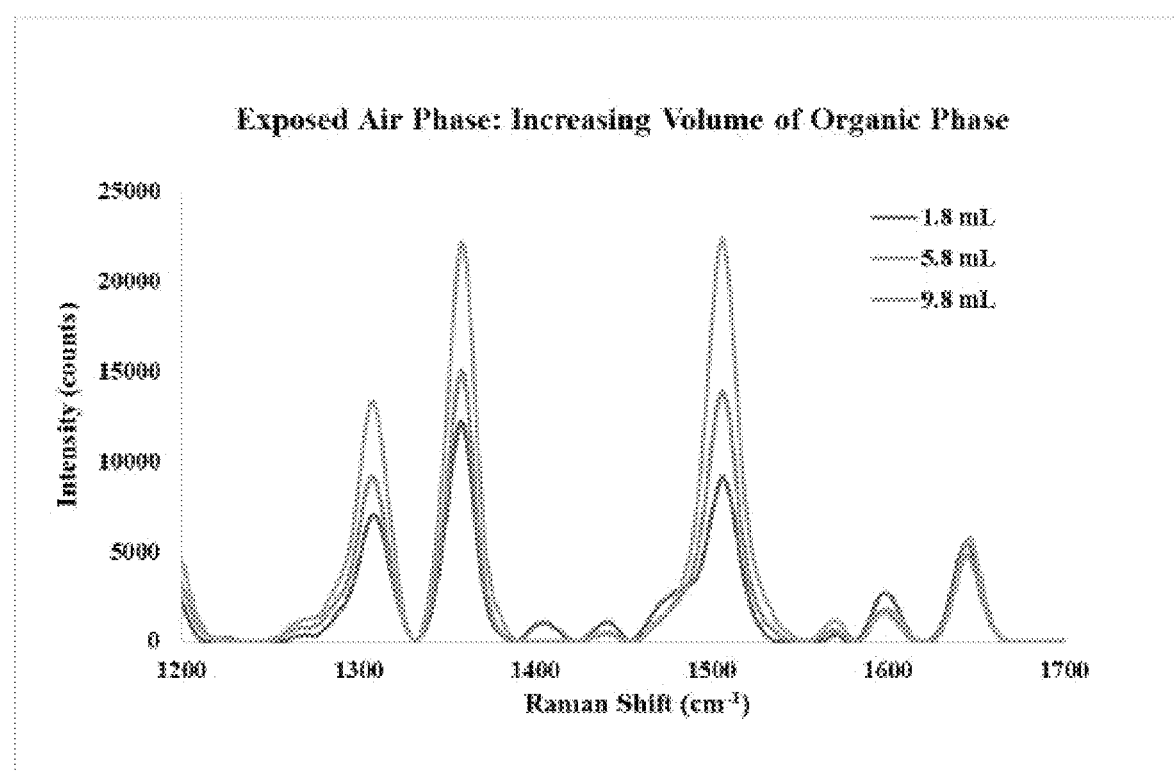
FIG. 18 shows exposed air phase.

As previously discussed, the area of air-exposed aqueous NP layer depends primarily on the volume of the assembly container and the volume of the organic solution. After depositing nanoparticle concentrate on the NAAO, the volume of the added organic solution determined the extent (height) to which the nanoparticle droplet is exposed to the air. Rising level of organic solution covered more of the nanoparticle droplet, therefore leaving a reduced area of air exposed NP surface. Experiments were carried out to adjust the size of the exposed droplet and measure the SERS signal for R6G on the resulting SERS-NAAO, as shown in FIG. 18. This area of development continues to be explored further to determine the optimum organic volume for the 115 mL petri dish and the 4 mL glass vial.

According to FIG. 18, substrates with the same dimensions were gold layered using an increasing amount of organic solution. An increasing organic volume on the same NP droplet volume reduced the amount of NP surface area which was exposed to air. The size of the exposed area directly affected the SERS signal for R6G, where a greater organic volume (smaller exposed area) provided the greatest enhancement.

During fabrication steps, the exposed air phase maintained a temperature around room temperature (23° C. in lab). Formation and drying in a colder environment like the fridge or freezer reduced the formation speed, increased the drying time, and ultimately resulted in an unimproved gold layer compared to room temperature conditions. Once removed from the cold environment, the nanoparticle concentrate droplet showed signs of still being wet and the dryer areas showed layer stacking.

Drying at room temperature overnight also required that the petri dish or vial be capped. Assembly containers which were left open during the drying process resulted in pronounced uneven drying of the gold layer. The gold layer could have been greatly influenced by environmental changes in the air (mechanical, thermal etc.) and further disturbed when drying.

The key points for Air Phase include (1) air phase should be close to room temperature for overnight drying; (2) important to control the volume of exposed liquid phase; (3) No drying in fridge to avoid multilayer stacking; (4) SERS signal strongly affected by the volume of droplet exposed to air; (5) Assembly containers must be closed during evaporation.

Chemical Inducer: Ethanol

The as-synthesized gold nanoparticles are stabilized in solution with the reducing agent citrate acting as the capping ligand. The citrate molecule creates a negatively charged nanoparticle surface which limits assembly due to interparticle electrostatic repulsion. The electrostatic interactions prevent the nanoparticles from aggregating, therefore keeping them suspended in solution. On the other hand, this electrostatic repulsion prevents the nanoparticles from forming closely packed arrays at the water/oil interface. For SERS sensing, the gold nanoparticles need to be tightly packed to form nanometer scaled interparticle gaps for EM field enhancement. For this fabrication process, it's essential that the electrostatic repulsion between nanoparticles be overcome to form a SERS-active 2D array. Here, interfacial self-assembly is induced with the careful addition of ethanol as a charge reduction method. The addition of ethanol destabilizes the nanoparticles which drives them to the water/hexane interface, where they undergo an in-situ ligand passivation with dodecylamine. The new ligand helps reduce the electrostatic repulsion, by controlling the interparticle separation between the nanoparticles, therefore causing the formation of gold layer.

Microliter volumes of ethanol were administered to the water/hexane interface using a sterile syringe at a rate of 1 drop per minute. Compared to a disposable glass pipette, the smaller syringe tip allowed for more precise drops that caused less movement when added. It was very important that the addition of ethanol did not disturb the nanoparticle droplet on the NAAO. The location of addition within the assembly container also had a great effect on the overall film. Ethanol addition was tested at several distances away for the substrate. These tests confirm an approximate optimum distance from the substrate for adding ethanol. When the syringe was placed almost touching the nanoparticle droplet, the gold layer was readily formed but the addition clearly caused a disturbance to the film. Spots on the film were darker than others due to the close-range disturbance caused by the ethanol. Ethanol drops were also administered closer to the edge of the container wall. This type of addition slowed down film formation, mainly because the ethanol in the ddHex fluid had to gradual flow to the substrate. Ultimately, an approximate distance of 0.2 inches from the edge of the square substrate was implemented. Ethanol addition at this distance away, but dropped near the square corner, was also used to reduce disturbance during layer formation. In the future for scaled-up fabrication, ethanol addition can be tested using a non-circular shaped nozzle.

The key points for the chemical inducer include (1) ethanol drives assembly acting as a charge reduction method; (2) the rate of addition has to be controlled, here 1 drop/minute; (3) a sterile syringe tip allowed addition of ethanol without disturbing droplet; (4) ethanol is administered 0.2 inches away for substrate edge.

SERS-NAAO Surface Optical Characterization: Reflectance Spectroscopy

Figure 19:
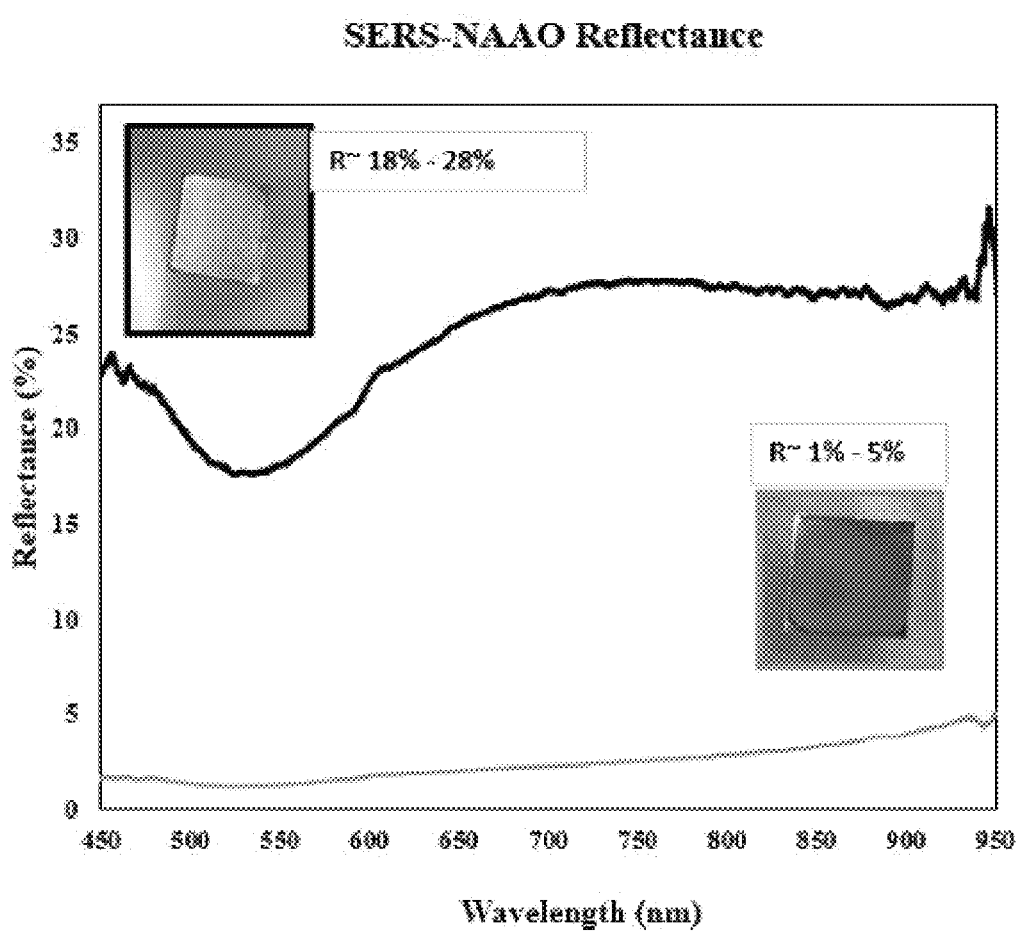
FIG. 19 shows Class 1 and Class 2 SERS-NAAO display characteristic reflectance features in the spectra.

Following fabrication, the dried SERS-NAAO sensors are optically characterized with UV-Vis reflectance spectroscopy, as shown in FIG. 19. The spectrum gives insight into the plasmonic coupling in the gold nanoparticle array and the optical response to the incident light when moving forward to laser induced excitation. The "dip" feature at ~530 nm is due to the surface plasmon absorption of the deposited gold nanoparticles. Another broad dip present in the NIR region results from the coupling of individual nanoparticles when forming the gold array in the layer. The alkylamine brings the nanoparticles within nanometers of each other, causing the surface plasmons of nearby particles to hybridize creating a low energy mode for NIR excitation.

Two classes of SERS-NAAO (10×10 mm) substrates were reproduced using the discussed protocol. Class 1 includes the SERS-NAAOs which remained in the shallow organic pool after the gold film formed and class 2 refers to substrates that once the gold film was formed an additional draining/siphoning step was implemented to remove the organic solution. After processing, the gold film is allowed to dry in the petri dish and covered with the lid. A closed drying environment was implemented to attempt to control the conditions of the air phase (e.g., mechanical, thermal). When the organic solution remains in the closed dish with the gold film during evaporation, this results in a Class 1 SERS-NAAO which is shinier and uniform after drying and has a reflectance percentage in the range 18%-28%. Gold films dried after removing the organic solution, Class 2, were darker in color and presented more regions of discoloration. The reflectance percentage for Class 2 SERS-NAAOs had reflectance percentages in the range of 1%-5%. The spectrum for each class showed the same features although the feature at ~530 nm was more pronounced for Class 1. Class 2 substrates are likely more absorptive for a range of reasons including the presence of larger aggregate structures that did not assemble into the ordered array. The greater extinction (absorption+scattering) properties observed for Class 2 substrates is negatively counteracted by a non-uniformity brought on most likely by the larger gold nanoparticle aggregates.

FIG. 19 shows Class 1 and Class 2 SERS-NAAO. Two classes of SERS-NAAOs were observed following fabrication and drying. Class 1 and class 2 display characteristic reflectance features in the spectra. The main differences being the increase in reflectance from 18% to 28% and pronounced LSPR dip at 530 nm for the class 1 SERS-NAAO.

Reflectance spectroscopy as a characterization method is a quick and simple method for checking the optical properties of the NAAO that result for the gold layering. The reflectance probe can be translated to measure the reflectance spectrum across a larger SERS-NAAO surface area. An error in the average reflectance percentage for the plasmonic spectral features can be determined and monitored for quality insight. For the current substrates, the error in reflectance percentage and error is 17±2% at 530 nm and 27±3% at 800 nm.

The key points of SERS-NAAO optical properties includes (1) LSPR modes in the visible and NIR; (2) coupled NIR band for 785 nm excitation; (3) two classes: Class 1 (no drain) Class 2 (organic drain); (4) reflectance percentage 18%-28%; and (5) reflectance spectrum good for quality determination.

SERS-NAAO Surface SERS Sensing of Phenylalanine in Water

Figure 20:
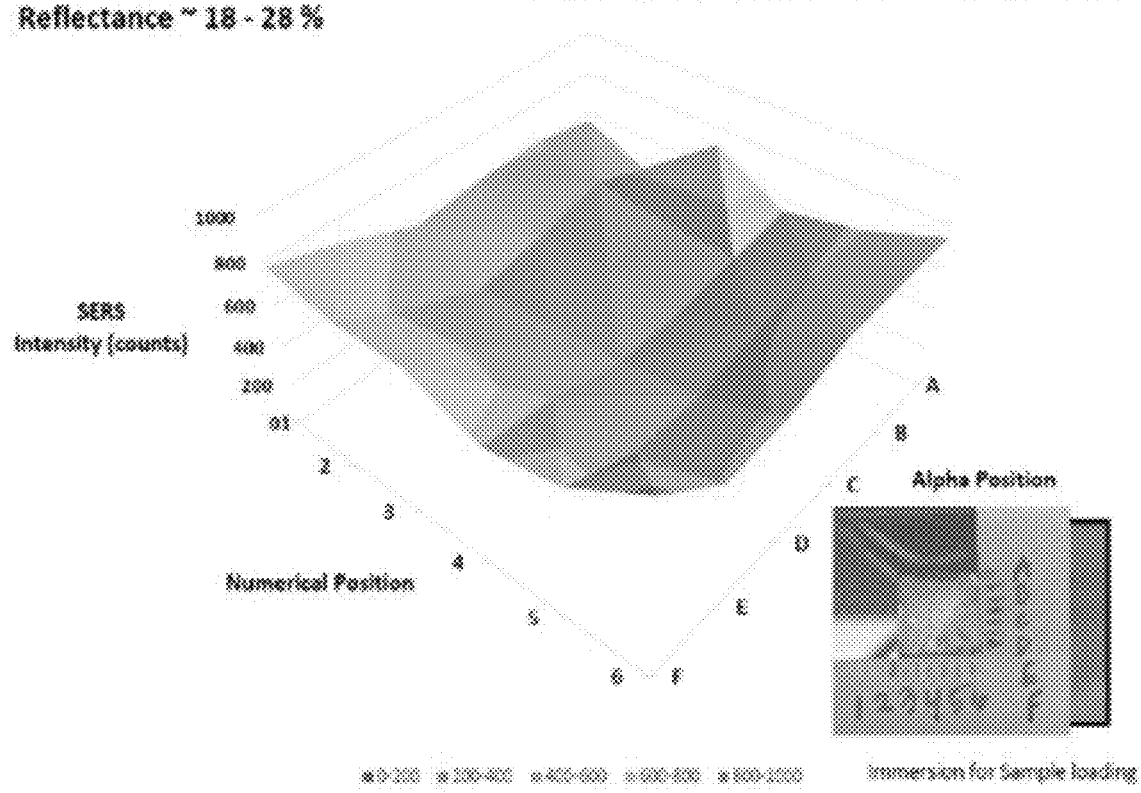
FIG. 20 shows uniformity of SERS Signal, Class 1 SERS signal collected at 36 points across the class 1 substrate.
Figure 21:
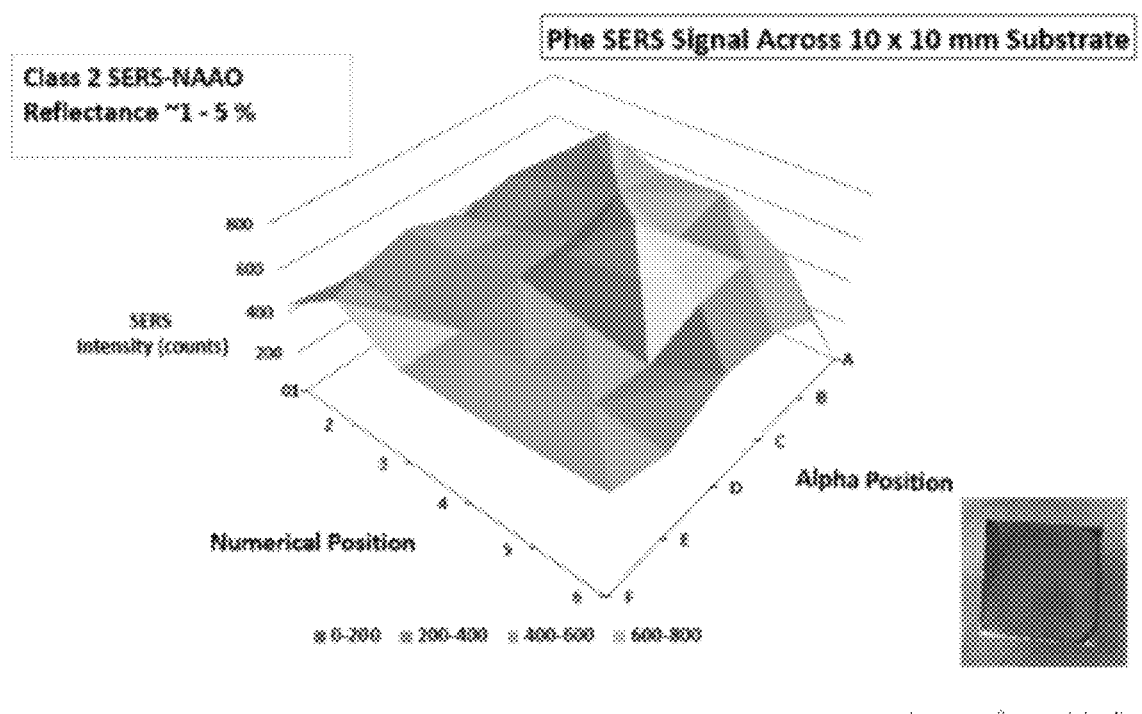
FIG. 21 shows uniformity of SERS Signal, Class 2 SERS signal collected at 36 points across the class 2 substrate.

The SERS spectra for phenylalanine in water loaded (by immersion) onto class 1 and class 2 SERS-NAAO substrates were collected following 785 nm excitation of the NIR plasmonic band. To gain insight into the uniformity of the three-phase gold layer, the 10×10 mm substrates were used for the SERS measurements to collect the phenylalanine signal at points across a large active area of the substrate. FIGS. 20-21 show the surface plot for the SERS signal at the Phe band (994 $cm^{-1}$) for 36 points across the class 1 and 2 substrates, respectively. The average intensity on the class 1 and class 2 substrates were 589 counts and 486 counts, respectively (grey regions). For the class 1 substrate, higher signal was detected at the outer perimeter of the substrate (yellow regions) which is likely due to non-uniform drying where nanoparticles flow to the edges upon evaporation. This has been described in the literature as the "coffee ring" effect (CRE) at the air/liquid interface that can be mitigated by controlling the particle-substrate, particle-flow, and particle-interface interactions. The class 2 substrate, as shown in FIG. 21, has a localized region with a greater than average intensity. This is due to the non-uniformity of the layer (darker spots) and potentially the sample immersion step.

The error of the SERS signal across the substrate also provides insight into the uniformity of the gold layer across the 10×10 mm substrate. For the class 1 and class 2 SERS-NAAO substrate the error is 18% and 22%, respectively, upon immersion in the sample solution. The errors are promising keeping in mind the wet-chemistry carried out to fabricate the surface and the uneven distribution of phenylalanine following immersion. Ultimately, the application will have a blood sample deposited on the substrate active area (both classes 10×10 mm active area) and localized in a µL droplet volume in the center. The size of the drop of blood for glucose measuring can range from 0.3 to 1 µL. In the blood studies to be discussed, 6 µL drop took up substantially less space in just the center of the substrate (grey region). Smaller substrate dimensions which are more proportional to the area taken up by the blood droplet should be considered.

FIG. 20 shows that Class 1 SERS signal collected at 36 points across the class 1 substrate. The laser excitation spot was translated across the substrate at these locations identified with alpha-numerical names. The substrate image is showing the SERS-NAAO following immersion. The substrate obtained some scratches during experimentation which will influence the signal counts and error. For signal collection the power was 6.3 mW, integration time 2 s, 3 averaged spectra, and 1 box smoothing correction.

FIG. 21 shows that Class 2 SERS signal collected at 36 points across the class 2 substrate. The substrate has dark regions that are caused by multilayers stacking. This stacking results in non-uniform layers that contribute to lowered reproducibility signal within a reasonable error. Even with contributions for the stacked regions, the error here is 22% which is also promising when compared to the shiny, uniform class 1 substrate which has an error of 18%. For signal collection, the power was 6.3 mW, integration time 2 s, 3 spectra average, and 1 box smoothing correction.

Figure 22:
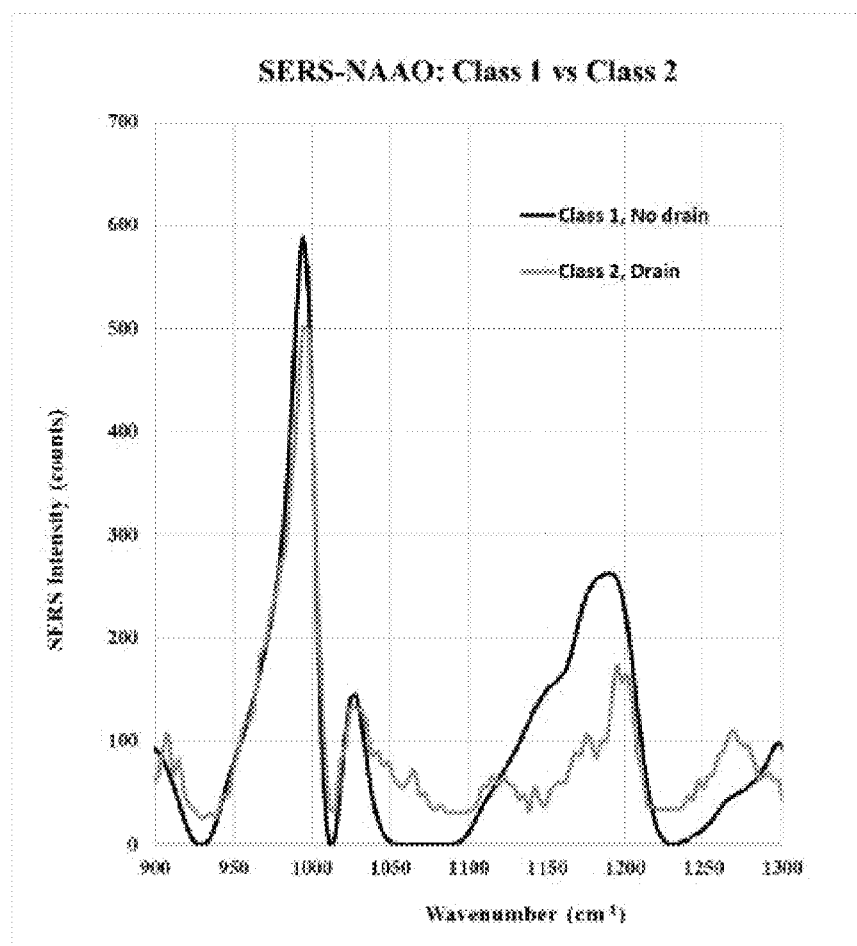
FIG. 22 shows averaged Phe (water) sensing behavior the SERS spectra for phenylalanine (water) adsorbed onto the class 1 and class 2 gold layers have a similar signal intensity but the class 2 substrate provides a non-uniformity surface resulting in a noisy spectrum for some bands.

FIG. 22 displays the truncated SERS spectrum for phenylalanine (water), isolating two vibrational modes at 994 $cm^{-1}$ and 1194 $cm^{-1}$. The spectrum for each class is an average of the spectrum obtained at all 36 points to gain insight into overall SERS signal across the entire landscape of the gold layers. The spectra represent the signal achievable for the phenylalanine molecule loaded onto SERS-NAAOs with an approximate 20% error. The spectral differences in FIG. 22 between class 1 and class 2 are related to the optical properties of each substrate obtained in the reflectance, the uniformity of the self-assembled gold nanoparticles, and the successful adsorption of phenylalanine at the surface and interparticle gaps of the nanoporous gold film. The reflectance spectra indicated the self-assembly and coupling of adjacent nanoparticles in both films forming a LSPR mode in the visible and NIR. For SERS detection, this LSPR "dip" in the reflectance spectrum was pumped using 785 nm excitation resulting in an amplified Phe signal. The uniformity for the class 2 substrate is represented by a 22% error which could be the main contribution to the noisy signal in FIG. 22 (orange trace). The non-uniformity is apparent in the images of the class 2 substrate where uncontrolled nanoparticle assembly resulted in larger aggregate structures making Phe adsorption at some bonds problematic. Although, the error isn't substantially different between the two classes which is apparent in the similar band intensities. Moving forward with development of the SERS-NAAOs, the signal intensity and error determined here using our collection parameters will be used as a benchmark for further improvements to the gold layering protocol.

The key points of SERS Sensing Phenylalanine in water includes (1) Class 1 substrates had the highest signal intensity and lower signal error; (2) small substrate should be considered for application, smaller than 10×10 mm; (3) CFE has to mitigated to provide uniformity from the center to the edges of the substrate; and (4) a signal error of 22% for class 1 substrates will serve as benchmark.

SERS-NAAO Surface SERS Sensing of Phenylalanine in Whole Blood

Figure 23:
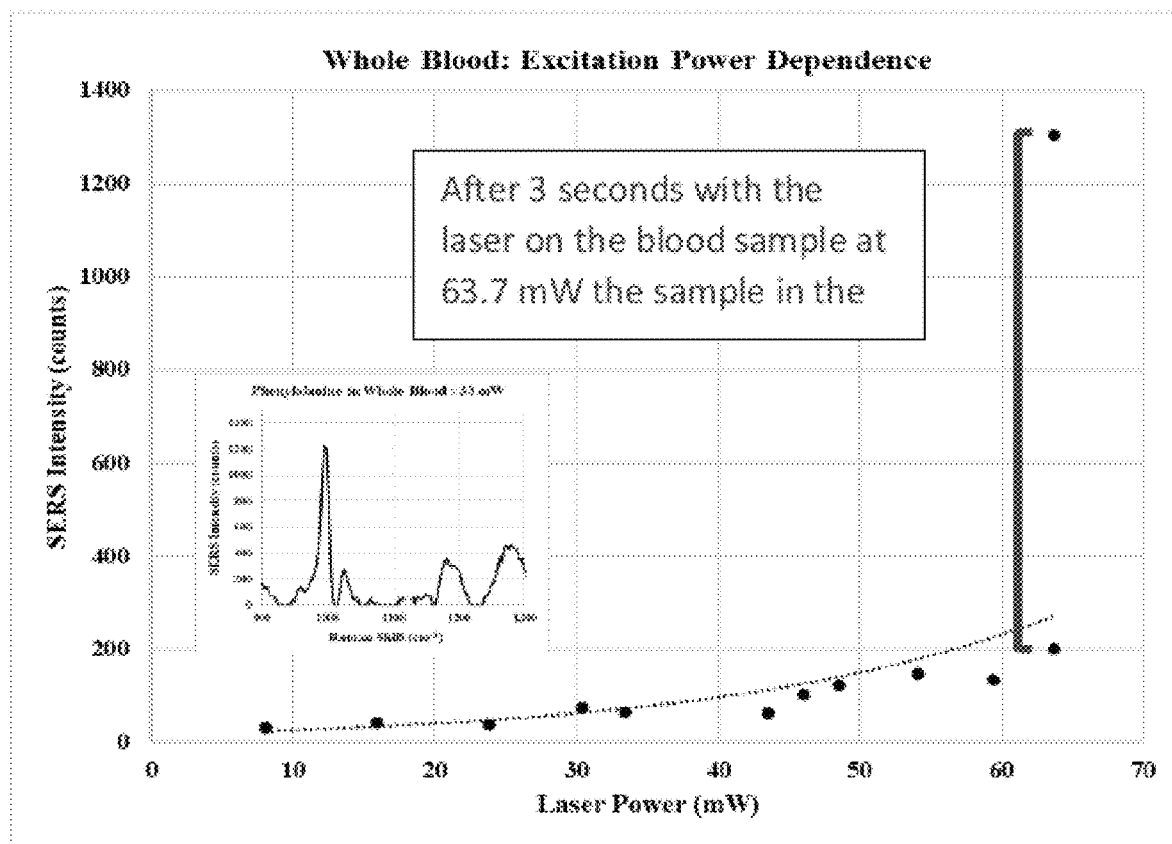
FIG. 23 shows the intensity of a blood component band at 752 $cm^{-1}$ as a function of power.

Prior to collecting the SERS spectrum for phenylalanine in whole blood, a power study of whole blood alone was conducted. Biological samples are broken down at moderate laser powers, therefore it's important to determine the power threshold when sensing in blood on the SERS-NAAOs. Fortunately, the aluminum-based substrate of the present invention is a mechanically and thermally robust surface, and not the limiting component to signal collection at higher laser powers, capable of tolerating powers above 100 mW. FIG. 23 shows the intensity of a blood component band at 752 $cm^{-1}$ as a function of power. When conducting the power study, leaving the laser impingent on the sample in between power changes resulted in breakdown in the blood at 45 mW. Removing the laser in between changing the powers and collecting fewer average spectra increased the breakdown threshold to 63.7 mW. At this high power, the spectra quickly evolves into a series of unresolved peaks that are likely not directly related to a specific vibration of phenylalanine, and the peak intensity nonlinearly increases from around 200 counts to 1300 counts. The SERS spectrum for phenylalanine in whole blood was collected at several incident laser powers. A power of 33 mW was the maximum power allowable before the phenylalanine doped sample began to degrade. In one embodiment, the SERS spectra in blood will be collected using a 1 s integration time or lower and a power below 20 mW to be conservative and avoid damaging the sample during interrogation.

As shown in FIG. 23 with respect to power threshold of whole blood, SERS signal was collected for blood at a range of powers 8.1-63.7 mW. Using the current Raman system and a 3 s integration time, a power of 45 mW begins to destroy the sample, but lowering the integration time to Is allows for laser excitation to extend out to 60 mW. Also, reducing the number of averaged spectra during collection can also reduce the likelihood of damaging the components in the blood sample.

The key pointes of SERS sensing phenylalanine in whole blood includes (1) lower excitation powers are necessary for excitation in whole blood; (2) a resting laser on the substrate damages the sample at 45 mW; (3) removing the laser between collection increased sample damage threshold to 63.7 mW; (4) for phenylalanine in whole blood the highest power allowed for our system is 33 mW; and (5) future SERS measurements will be conducted at a power lower than 20 mW.

Figure 24:
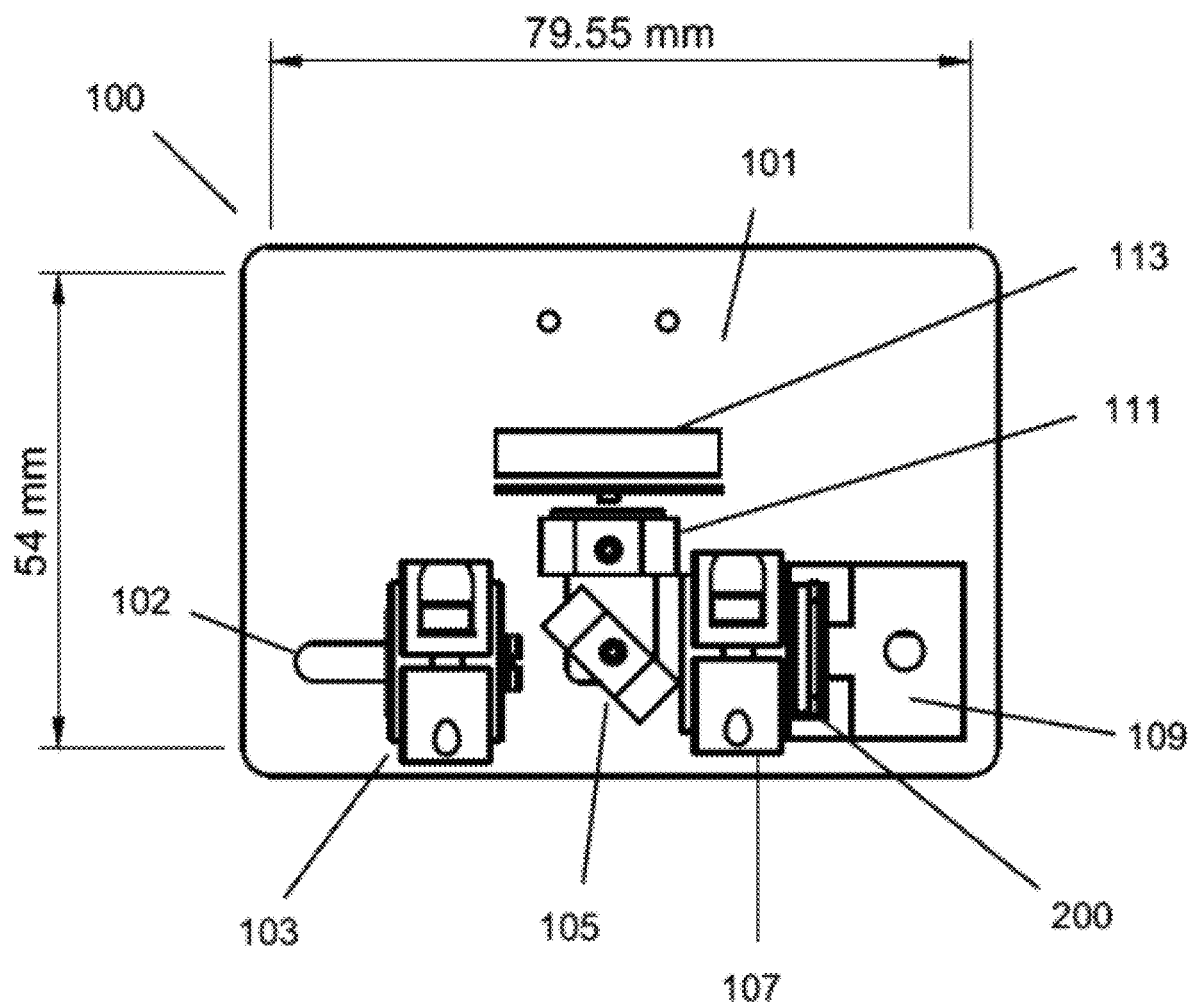
FIG. 24 shows a top schematic view of a handheld SERS device for detection of Phe in a PKU patient's blood.
Figure 25:
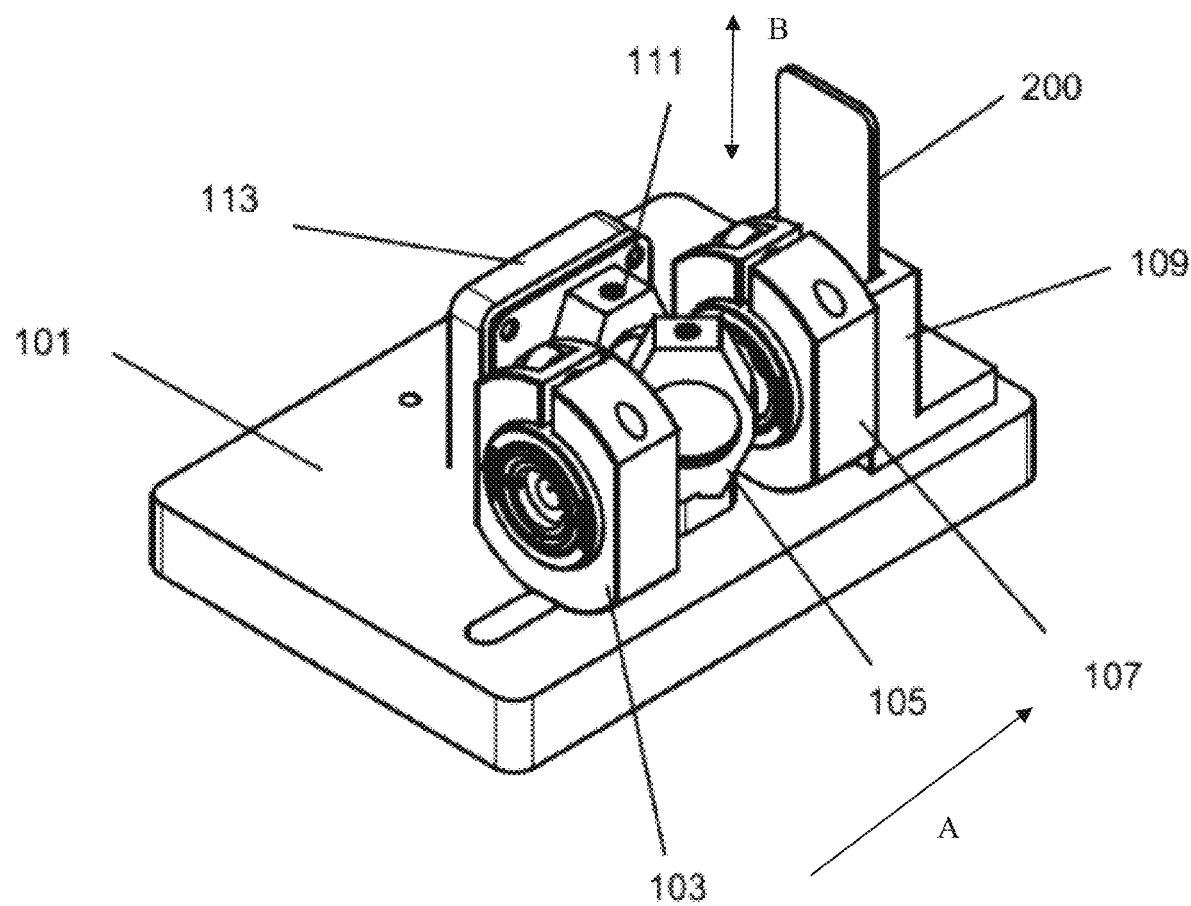
FIG. 25 shows a diagonal schematic view of the handheld SERS device for detection of Phe in a PKU patient's blood.
Figure 26:
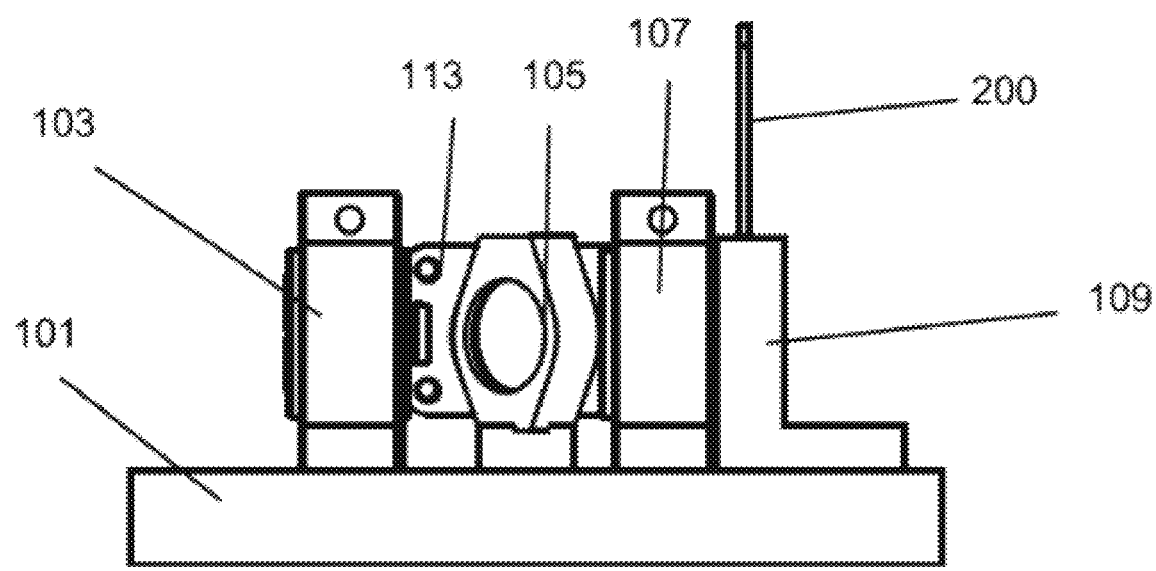
FIG. 26 shows a lateral schematic view of the handheld SERS device for detection of Phe in a PKU patient's blood.
Figure 27:
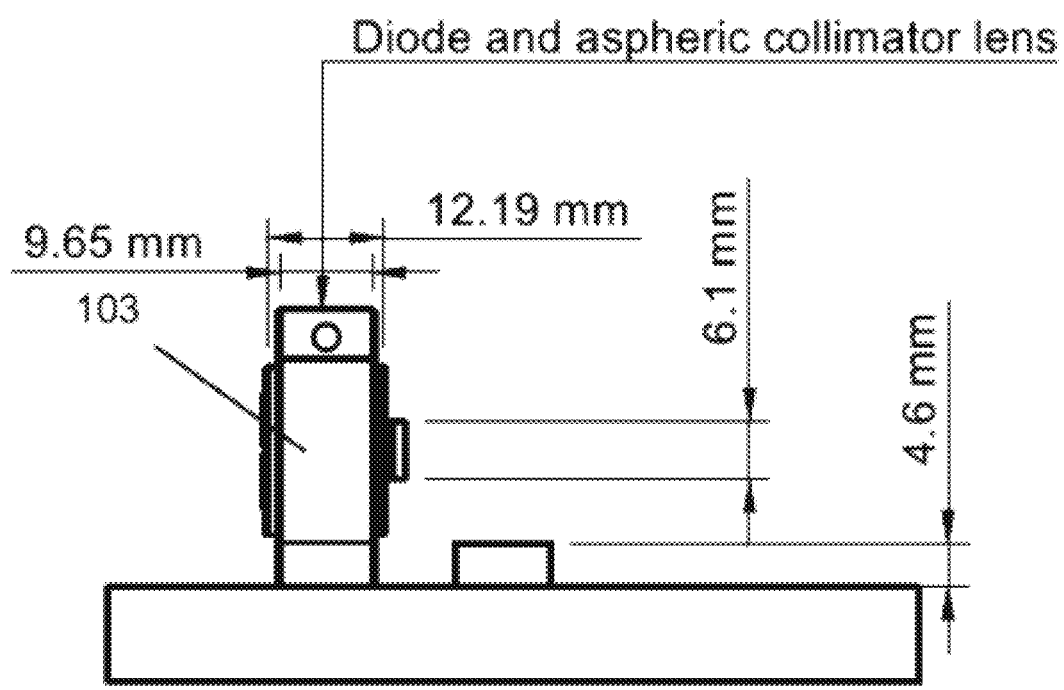
FIG. 27 shows a lateral schematic view of the diode and aspheric collimator lens mounted on the base of the handheld SERS device.
Figure 28:
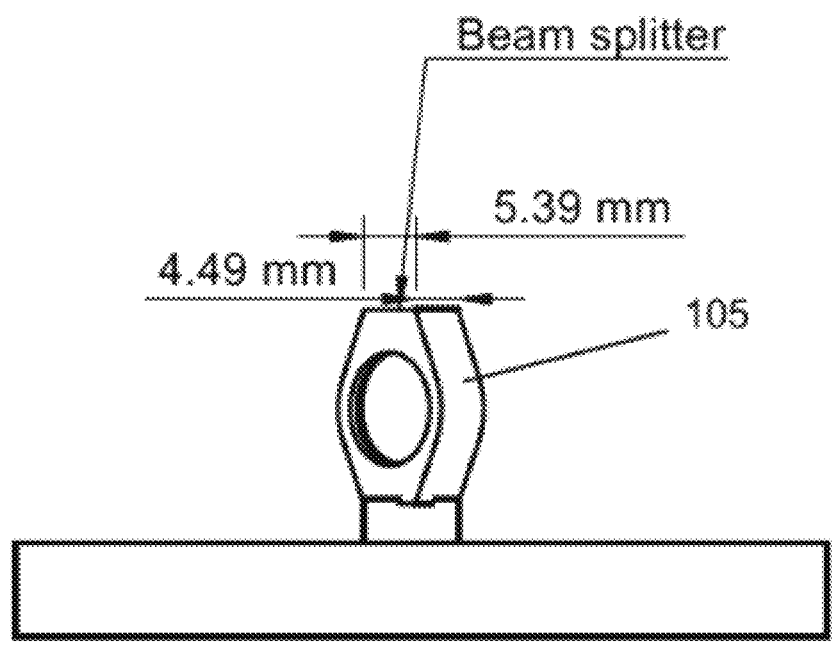
FIG. 28 shows a lateral schematic view of the beam splitter mounted on the base of the handheld SERS device.
Figure 29:
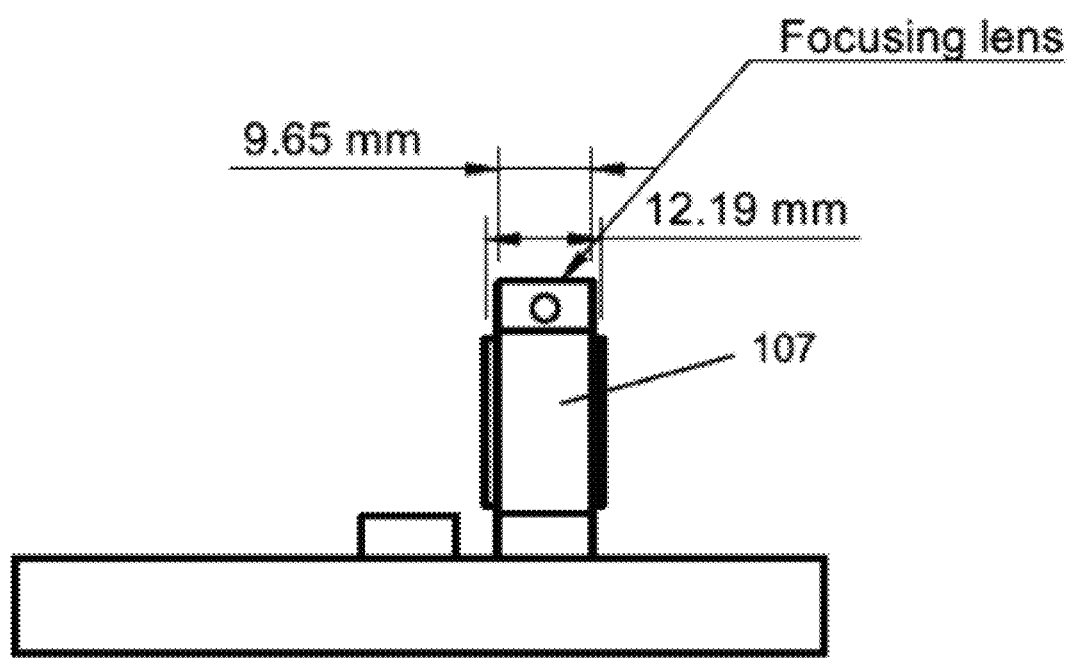
FIG. 29 shows a lateral schematic view of the focusing lens mounted on the base of the handheld SERS device.
Figure 30:
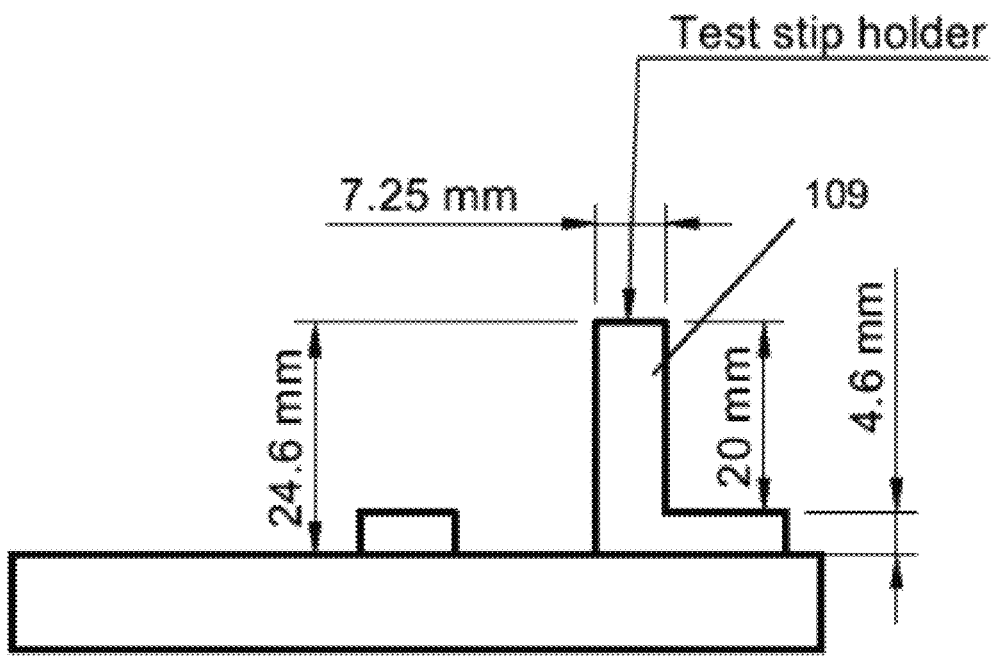
FIG. 30 shows a lateral schematic view of the test strip holder mounted on the base of the handheld SERS device.
Figure 31:
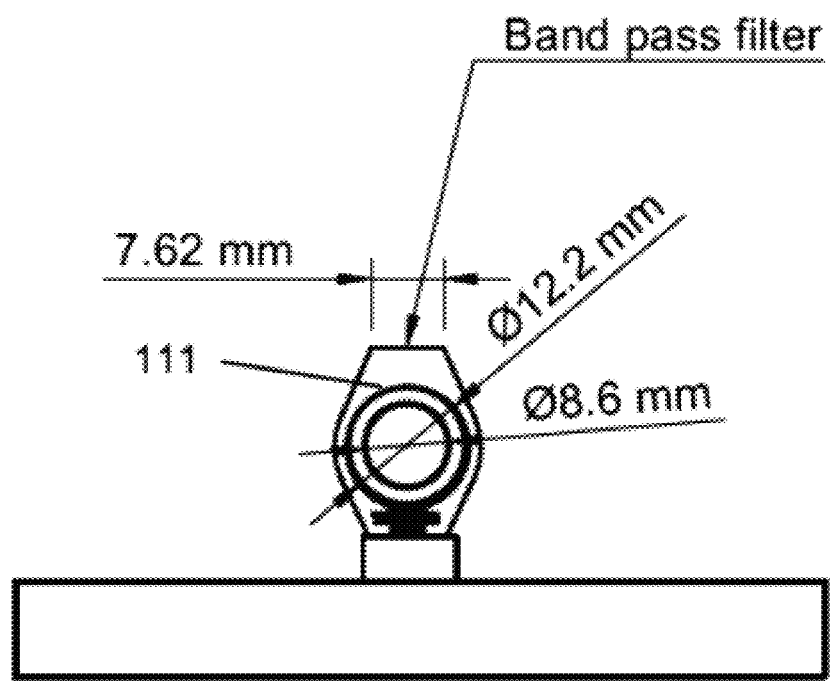
FIG. 31 shows a lateral schematic view of the band pass filter mounted on the base of the handheld SERS device.

SERS Handheld Device for Detection of Phe in PKU Patient's Blood and NAAO Test Strip Used in Association with the SERS Handheld Device FIGS. 24-26 show the schematic views of the SERS handheld device 100. In particular, the SERS handheld device 100 comprises a base 101 which has an approximately handheld size. In one embodiment, the base 101 has a length of about 50 mm, 60 mm, 70 mm, 80 mm, 90 mm, 100 mm, 150 mm, 200 mm, and 250 mm. In one embodiment, the base has a width of about 20 mm, 30 mm, 40 mm, 50 mm, 60 mm, 70 mm, 80 mm, 90 mm, 100 mm, 150 mm, 200 mm, and 250 mm. A diode mount and aspheric collimator lens 103 are mounted on a top surface of the base 101 through proper fastening means, e.g. screw, nail, glue, welding, and etc. The diode mount may receive a laser generator 102, e.g. a diode, such that the laser generator provides a laser beam.

A beam splitter 105 is mounted to the top surface of the base 101 via proper fastening means. The beam splitter 105 is positioned to receive the laser beam on one of its side, permitting the received laser beam from the laser generator 102 passing through it to reach a focusing lens 107 and a test trip 200 received in a test strip holder 109. The focusing lens 107 and test strip holder 109 are mounted to the top surface of the base 101 via proper fastening means. In one embodiment, the diode mount and aspheric collimator lens 103, the beam splitter 105, the focusing lens 107 and the test strip holder 109 are arranged in one straight line.

The laser beam reaches the test strip 200 and being reflected and/or deflected, passing through the focusing lenses 107 and reaches the other side of the beam splitter 105. The beam splitter 105 receives the reflected/deflected light and reflects the light to reach a band pass filter 111, which is mounted to the top surface of the base 101. In one embodiment, the band pass filter 111 selectively permits light of certain wavelength to pass through it so as to reach a light sensor 113 mounted on the base 101. In one embodiment, the beam splitter 105, the band pass filter 111 and the light sensor 113 are arranged in one straight line.

In one embodiment, the beam splitter 105 is arranged approximately 45 degree diagonally, relative to the straight line formed by the diode mount and aspheric collimator lens 103, the beam splitter 105, the focusing lens 107 and the test strip holder 109. In one embodiment, the beam splitter 105 is arranged approximately 45 degree diagonally, relative to the straight line formed by the band pass filter 111 and the light sensor 113. In another embodiment, this degree may be adjusted according to the size of the base, so as to provide optimal size of the handheld SERS device.

In one embodiment, the bandpass filter 111 will only allow photons at one vibrational energy (potentially a group of wavelengths) to reach the light sensor 113.

In one embodiment, the laser generator is a laser diode which is highly divergent, so the aspheric lens is necessary to collimate the laser light without introducing spherical aberrations. The collimated laser beam passes through the dichroic beam splitter 105 before becoming incident on the SERS-NAAO substrate on the test strip 200.

FIG. 25 shows the laser beam direction by arrow A, and directions for installing and removing of the test strop holder 109 is shown by double heads arrow B. In one embodiment, the test strip holder 109 is 3D printed piece which allows the dimensions to be matched to test strip. A port size in the housing can be adapted for test strip slot. In one embodiment, the test strip holder 109 is designed for the test strip 200. Once inserted, the test strip 200 remains fixed for excitation and signal collection.

In one embodiment, the bandpass filter 111 is tailored to exclusively transmit the phenylalanine signal to the detector. The center wavelength of the filter is controlled by tuning the angle of incidence. For collimated input light, independently rotating the bandpass filters serves to smoothly tune the combined transmission spectrum to the energy of the phenylalanine signal. Two filters define the short- and long-wavelength edges of the overall transmission curve.

FIGS. 27-31 show the individual elements, including the diode mount and aspheric collimator lens 103, the beam splitter 105, the focusing lens 107, the test strip holder 109, the band pass filter 111 and the light sensor 113, each being mounted to the base 101, and relative size of each element.

Figure 32A:
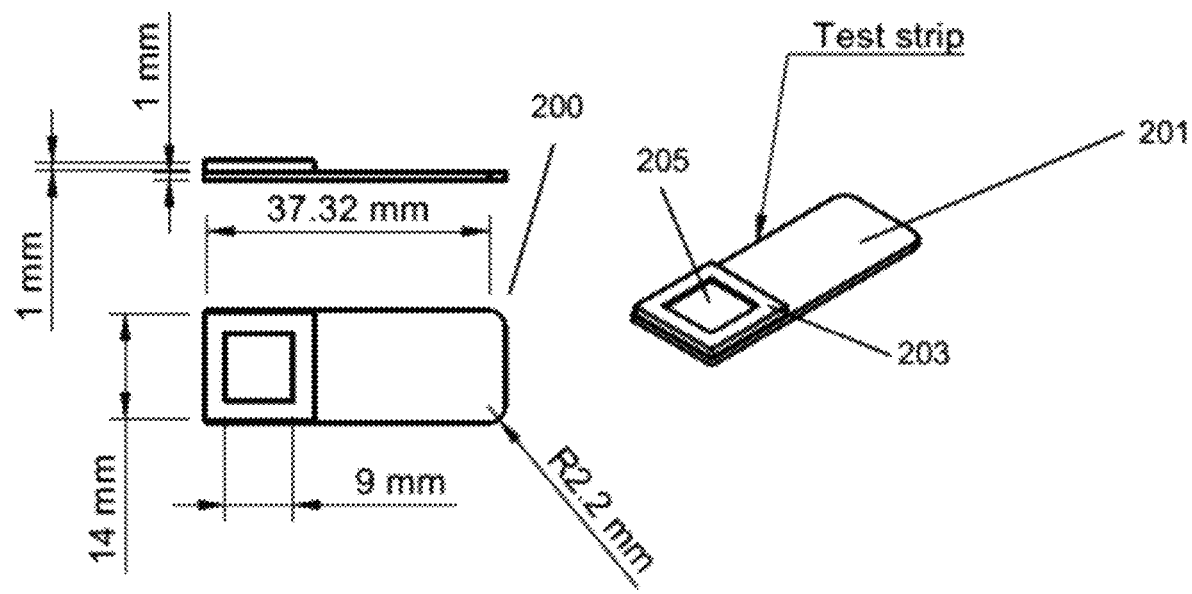
FIG. 32A shows schematic views of one embodiment of the test strip used in association with the handheld SERS device.
Figure 32B:
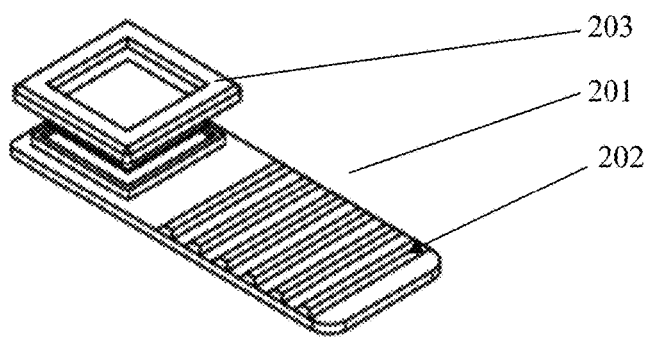
FIG. 32B shows schematic views of another embodiment of the test strip used in association with the handheld SERS device.
Figure 32B:
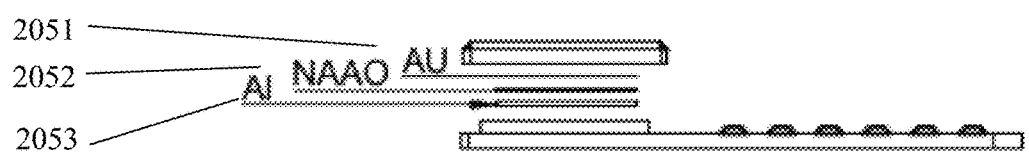

FIG. 32A shows one embodiment of the test strip 200. The test strip 200 includes a strip holder 201, a sample receiving substrate 205, and a sample rim 203 surrounding the sample receiving substrate 205. In one embodiment, the sample receiving substrate 205 includes the NAAO substrate fabricated according to at least one method disclosed above. In one embodiment, the test strip 200 has a thickness of less than 5 mm, 2 mm, 1 mm. In one embodiment, the sample receiving surface 205 and the rim 203 has a thickness of less than 1.5 mm, 1 mm, and 0.5 mm. FIG. 32B shows another embodiment of the test strip 200. In this embodiment, the strip holder 201 has rigged grooves 202 formed on top surface of the strip holder 201, so as to provide friction for a user of the device to hold the test strip 200 tight. The sample receiving substrate 205 has a gold layer 2051, a NAAO substrate 2052, and an aluminum layer 2053. In one embodiment, the gold layer 2051 is on top of the NAAO substrate 2052, which is on top of the aluminum layer 2053.

The test strip 200 receives a patient's test sample on its sample receiving surface. In one embodiment, the test sample contains a patient's blood. The test strip 200 is configured to be mechanically received by the test strip holder 109 of the SERS handheld device.

Figure 33:
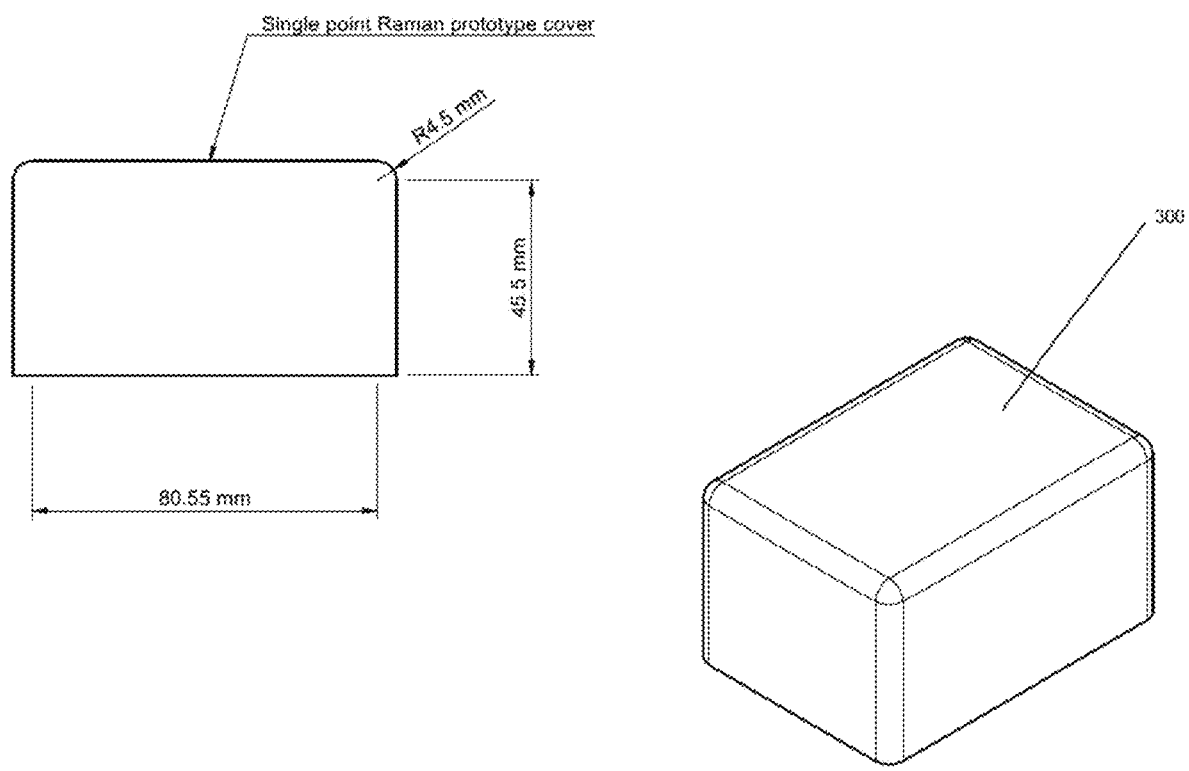
FIG. 33 shows a schematic view of a cover for the handheld SERS device.

FIG. 33 shows one embodiment of a cover 300 covering the SERS handheld device. The cover 300 and the base 101 form a housing enclosing the diode mount and aspheric collimator lens 103, the beam splitter 105, the focusing lens 107, the test strip holder 109, the band pass filter 111 and the light sensor 113. In one embodiment, the cover 300 is light-tight such that no laser beams would escape from, and no light would enter into the housing formed by the cover 300 and the base 101. The cover is built by additive manufacturing method. Cover is manufactured with durable material to protect laser, optics and detector. In one embodiment, a 3D printer is used to create the cover 300.

Figure 34:
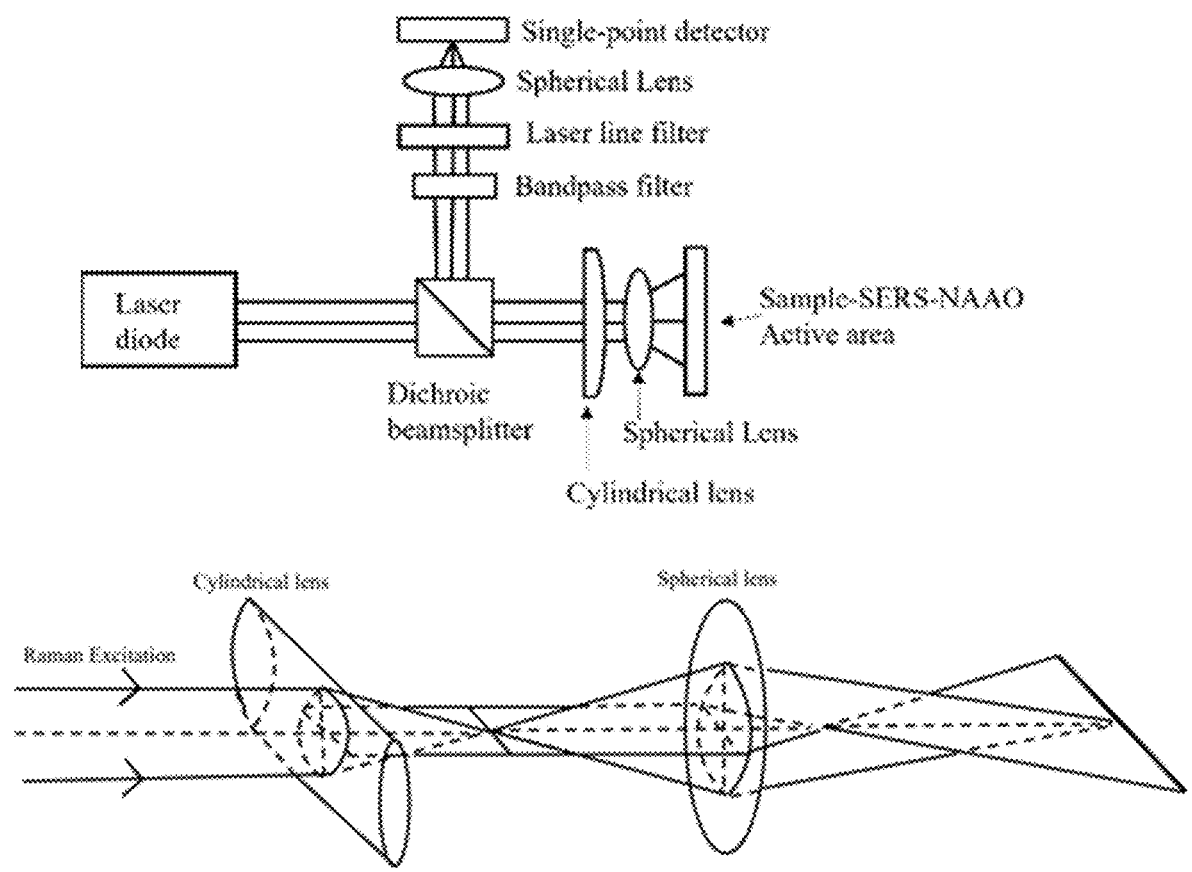
FIG. 34 shows another embodiment of spectrometer optical schematic in the upper panel and cylindrical lens for line focusing in the lower panel.

FIG. 34 shows another embodiment of spectrometer optical schematic in the upper panel and cylindrical lens for line focusing on the lower panel. Absorption of the focused laser light at the blood sample-SERS-NAAO can lead to local heating and photo induced processes at the blood sample-SERS-NAAO. To avoid this problem without enlisting a raster scanning system, a cylindrical lens can be introduced to the optical pathway. Use of the cylindrical lens changes the illuminated area of the sample so that a line-focus is met, such that a maximum amount of scattered light using reduced laser irradiation.

Example 3—Detection of Rhodamine 6G Using the Handheld SERS Device

In one embodiment, the device of the present invention is used for detection of Rhodamine 6G.

Figure 36:
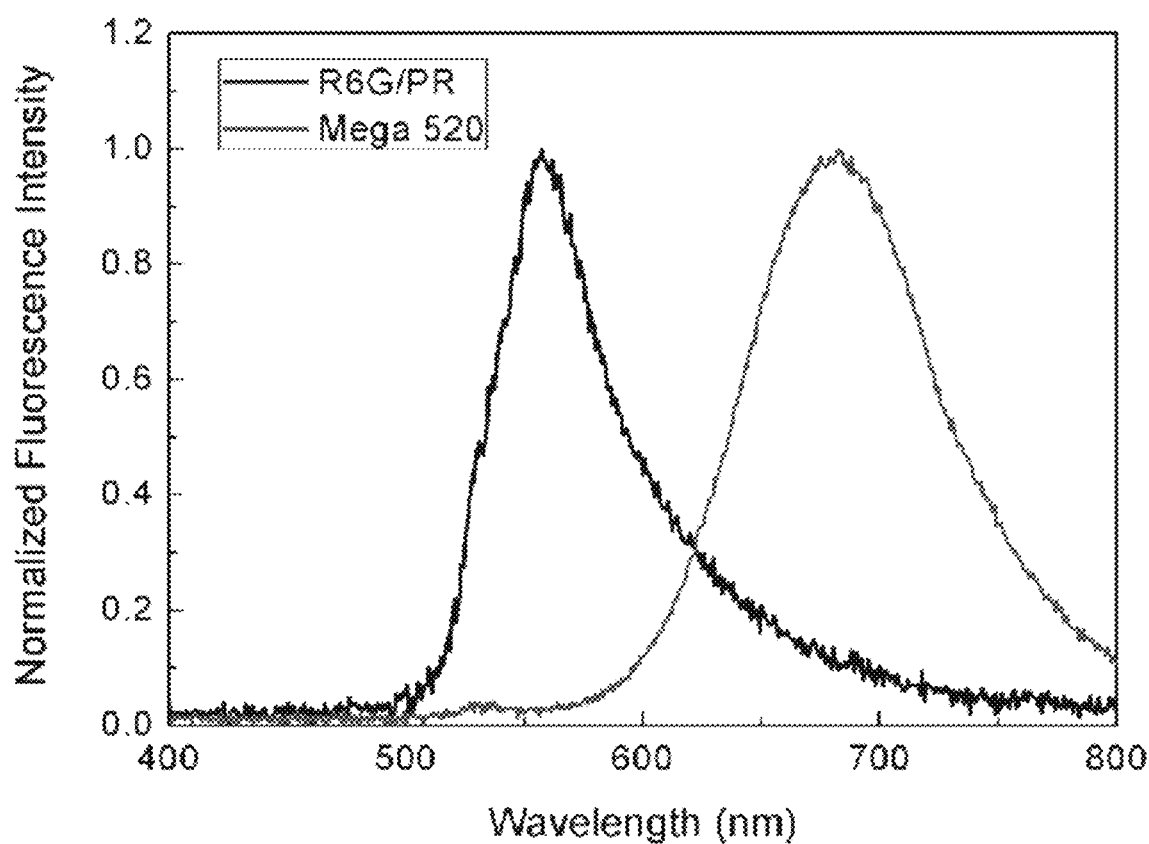
FIG. 36 shows the emission spectra of Rhodamine 6G for a 532 nm laser of the device.

FIG. 36 shows the emission spectra of Rhodamine 6G for a 532 nm laser of the device. In one embodiment, the device was built by using two variable band pass filters, which block all light outside of a certain allowable range. These filters are individually controlled by two stepper motors with 200 steps per revolution. It was determined that light can be passed through these filters when both filters are at 0 steps through 70 steps. Using Ocean Insight's 3689K1 White LED and a spectrometer, the allowable range of light was determined to be from 540 to 628 nm. Keeping the number of steps the same, 8 data points were determined from 0 steps to 70 steps in increments of 10. The input laser was 533 nm and the concentration of Rhodamine 6G was 3.75e-5 mol/L.

Figure 37:
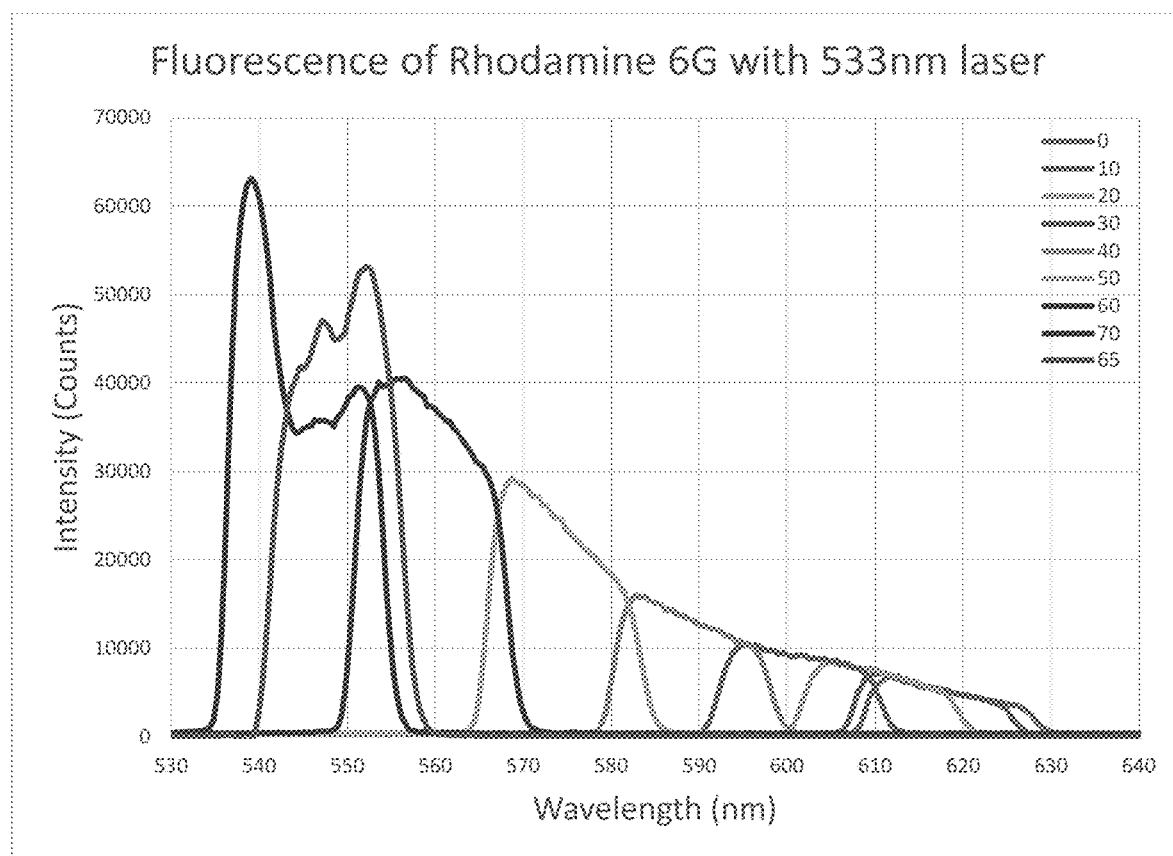
FIG. 37 shows the result of detection of Rhodamine 6G using the laser.

FIG. 37 shows the result of detection of Rhodamine 6G using the laser. In particular, the cumulative data from motor steps 0 to 65 matches with the literature, but there is an unexpected peak at motor step 70. This is suspected to be reflectance of the laser itself or from the glass vial that held the Rhodamine 6G sample.

In one embodiment, the device includes a 533 nm laser which hits a mirror, hits the sample in a sample holder, passes through two filters, before being collected by the light sensor. In another embodiment, the device may include only one filter which is determined from the peaks of a selected biomarker.

Example 4—Software and Hardware of the Handheld SERS Device

Figure 38:
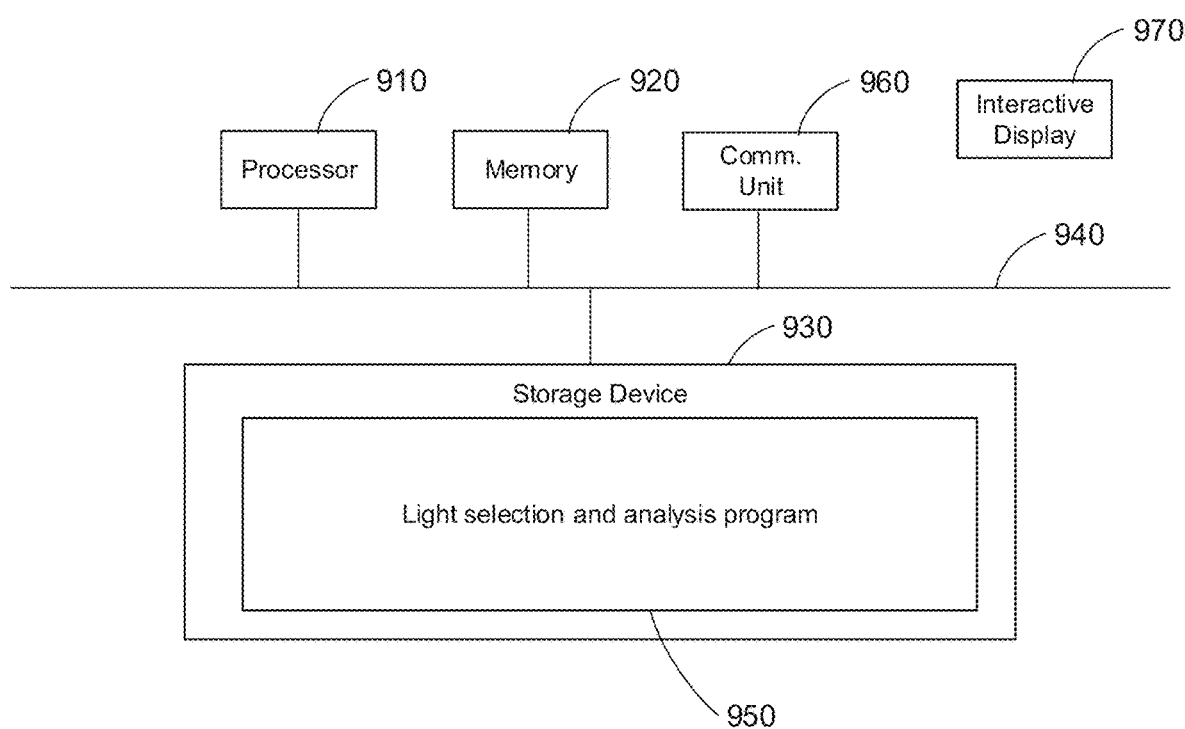
FIG. 38 shows a control and storage system of the biomarker/chemical measuring device of the present invention.

As shown in FIG. 38, in one embodiment, the device of the present invention includes a control unit 910, a memory 920, and a storage device 930, and a bus 940 interconnecting the processor 910, the memory 920 and the storage device 930. In certain embodiments, the device of the present invention may include necessary hardware and/or software components (not shown) to perform its corresponding tasks. Examples of these hardware and/or software components may include, but not limited to, communication unit, light sensor reading unit, other required memory modules, interfaces, buses, Input/Output (I/O) modules and peripheral devices, and details thereof are not elaborated herein.

The control unit 910 controls operation of the device, which may be used to execute any computer executable code or instructions. In certain embodiments, the control unit 910 may be a central processing unit (CPU), and the computer executable code or instructions being executed by the control unit 910 may include an operating system (OS) and other applications, codes or instructions stored in the device.

The memory 920 may be a volatile memory module, such as the random-access memory (RAM), for storing the data and information during the operation of the device. In certain embodiments, the memory 920 may be in the form of a volatile memory array.

The storage device 930 is a non-volatile storage media or device for storing the computer executable code or instructions, such as the OS and the software applications for the device. Examples of the storage device 930 may include flash memory, memory cards, USB drives, or other types of non-volatile storage devices such as hard drives, floppy disks, optical drives, or any other types of data storage devices. In certain embodiments, the device may have more than one storage device 930, and the software applications of the device may be stored in more than one storage device 930 separately.

In one embodiment, the device of the present invention includes a control unit 910 in communication with the light sensor 113 to receive readings and/or signals from the light sensor 113, via wire or wireless connection. The control unit 910 may be a microcontroller unit (MCU) including one or more processors and being configured to receive signals from the light sensor 113.

In one embodiment, the readings and/or signals from the light sensor 113 include wavelengths of the light received by the light sensor and intensity of the light received at each wavelength.

As shown in FIG. 38, the computer executable code stored in the storage device 930 may include a light selection and analysis program 950. Specifically, the light selection and analysis program 950 is a software module which, when executed, analyzes the readings and/or signals received by the light sensor 113, based on the biomarkers/chemicals being tested, and produce one or more analysis results. For example, in one embodiment, the light selection and analysis program 950 analyzes the readings and/or signals received by the light sensor 113 to determine the Phe value in the blood of the user, and if the Phe value is in a normal range or an abnormal range.

In one embodiment, the control unit 910 is in electronic communication with an interactive display 970 coupled to the control unit 910 for displaying the readings and/or signals of the light sensor 113, and its analysis results of the readings and/or signals, e.g. whether the Phe level in the blood of the user is normal or not.

In one embodiment, the interactive display 970 receives inputs regarding the biomarkers/chemicals to be tested. In one embodiment, the biomarkers/chemicals to be tested is communicated to the light selection and analysis program 950. The light selection and analysis program 950 determines the parameter settings for the device of the present invention based on the input biomarkers/chemicals to be tested. The parameter settings include wavelengths of light that the band pass filter 111 selectively permits to pass through it so as to reach a light sensor 113 mounted on the base 101. For example, when the user inputs a biomarker/chemical to be tested through the interactive display 970, the light selection and analysis program 950 would determine the wavelengths and other parameter settings corresponding to the biomarker/chemical. The wavelengths and other parameter settings would then be communicated to the control unit 910, and being used for adjusting the band pass filter 111 and other component of the device to test the biomarker/chemical input.

In one embodiment, the interactive display 970 receives biometrics and other data of the user including age, gender, weight, diagnosed diseases, prescribed medications, and etc., which are then communicated to the light selection and analysis program 950. In one embodiment, the analyze results produced by the light selection and analysis program 950 are based on the biometrics and other data of the user. In one embodiment, the interactive display 970 receives data of the non-biological samples being collected, e.g., location of the non-biological samples being collected, temperature, humidity, pH of the supporting environment of the non-biological samples. In one embodiment, the analyze results produced by the light selection and analysis program 950 are based on the data of the non-biological samples.

The interactive display 970 may include an APP with a graphical user interface (GUI). The interactive display 970 may include a display and/or a mobile device such as a smart phone, a smart watch, a tablet, etc. In one embodiment, the light selection and analysis program 950 is embedded in the APP instead of the storage device 930. The term "APP", used herein the specification, refers to an application, especially as downloaded by a user to and installed in a mobile device, which a software program that is designed to perform specific functions directly for the user or, in some cases, for another application program or for operations of the device.

In one embodiment, the control unit 910 is in communication with the interactive display 970 via wired or wireless communication unit 960. In one embodiment, the communication unit 960 provides communication using Bluetooth, WiFi, or other wireless communication methods.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

TABLE 1

Commonly studied cancer biomarkers measured from different sample types.

| Biomarker | Cancer | Application | Tumor Tissue/ Bone Marrow | Blood | Urine | Stool | Cereb. Fluid | Saliva Buccal Swab |
|---|---|---|---|---|---|---|---|---|
| ALK protein overexpression | NSCLC, anaplastic large cell lymphoma, and histiocytosis | To help determine treatment and prognosis | X | | | | | |

TABLE 1-continued

Commonly studied cancer biomarkers measured from different sample types.

| Biomarker | Cancer | Application | Tumor Tissue/ Bone Marrow | Blood | Urine | Stool | Cereb. Fluid | Saliva Buccal Swab |
|---|---|---|---|---|---|---|---|---|
| Alpha-fetoprotein (AFP) | Liver cancer and germ cell tumors | To help diagnose liver cancer and follow response to treatment; to assess stage, prognosis, and response to treatment of germ cell tumors | | X | | | | |
| BCL2 protein | Lymphomas and leukemias | For diagnosis and planning therapy | X | X | | | | |
| BCR-ABL fusion protein | Chronic myeloid leukemia, acute lymphoblastic leukemia, and acute myelogenous leukemia | To confirm diagnosis, predict response to targeted therapy, help determine treatment, and monitor disease status | X | X | | | | |
| Beta-2-microglobulin (B2M) | Multiple myeloma, chronic lymphocytic leukemia, and some lymphomas | To determine prognosis and follow response to treatment | | X | X | | X | |
| Beta-human chorionic gonadotropin (Beta-hCG) | Choriocarcinoma and germ cell tumors | To assess stage, prognosis, and response to treatment | | X | X | | | |
| Bladder Tumor Antigen (BTA) | Bladder cancer and cancer of the kidney or ureter | As surveillance with cytology and cystoscopy of patients already known to have bladder cancer | | | X | | | |
| BRAF protein | Cutaneous melanoma, Erdheim-Chester disease, Langerhans cell histiocytosis, CRC, and NSCLC | To help determine treatment | X | | | | | |
| BRCA1 and BRCA 2 protein | Ovarian and breast cancers | To help determine treatment | X | X | | | | |
| CA15-3/CA27.29 | Breast cancer | To assess whether treatment is working or if cancer has recurred | | X | | | | |
| CA19-9 | Pancreatic, gallbladder, bile duct, and gastric cancers | To assess whether treatment is working | | X | | | | |
| CA-125 | Ovarian cancer | To help in diagnosis, assessment of response to treatment, and evaluation of recurrence | | X | | | | |
| CA27.29 | Breast cancer | To detect metastasis or recurrence | | X | | | | |
| Calcitonin | Medullary thyroid cancer | To help in diagnosis, check whether treatment is working, and assess recurrence | | X | | | | |
| Carcinoembryonic antigen (CEA) | CRC and some other cancers | To monitor the effectiveness of treatment and to detect recurrence or spread | | X | | | | |
| CD19 | B-cell lymphomas and leukemias | To help in diagnosis and to help determine treatment | X | X | | | | |
| CD20 | Non-Hodgkin lymphoma | To help determine treatment | | X | | | | |
| CD22 | B-cell lymphomas and leukemias | To help in diagnosis and to help determine treatment | X | X | | | | |
| CD25 | Non-Hodgkin (T-cell) lymphoma | To help determine treatment | | X | | | | |

TABLE 1-continued

Commonly studied cancer biomarkers measured from different sample types.

| Biomarker | Cancer | Application | Tumor Tissue/ Bone Marrow | Blood | Urine | Stool | Cereb. Fluid | Saliva Buccal Swab |
|---|---|---|---|---|---|---|---|---|
| CD30 | Classic Hodgkin lymphoma, and B-cell and T-cell lymphomas | To help determine treatment | X | | | | | |
| CD33 | Acute myeloid leukemia | To help determine treatment | X | | | | | |
| Chromogranin A (CgA) | Neuroendocrine tumors | To help in diagnosis, assessment of treatment response, and evaluation of recurrence | X | | | | | |
| Circulating tumor cells of epithelial origin (CELLSEARCH) | Metastatic breast, prostate, and CRC | To inform clinical decision-making, and to assess prognosis | X | | | | | |
| C-kit/CD117 | Gastrointestinal stromal tumor, mucosal melanoma, acute myeloid leukemia, and mast cell disease | To help in diagnosis and to help determine treatment | X | X | | | | |
| Cyclin D1 (CCND1) protein | Lymphoma and myeloma | To help in diagnosis | X | | | | | |
| Cytokeratin fragment 21-1 | Lung cancer | To help in monitoring for recurrence | X | | | | | |
| Des-gamma-carboxy prothrombin (DCP) | Hepatocellular carcinoma | To monitor the effectiveness of treatment and to detect recurrence | X | | | | | |
| DPD protein | Breast, CRC, gastric, and pancreatic cancers | To predict the risk of a toxic reaction to 5-fluorouracil therapy | X | | | | | |
| EGFR protein | NSCLC | To help determine treatment and prognosis | X | | | | | |
| Estrogen receptor (ER)/progesterone receptor (PR) | Breast cancer | To help determine treatment | X | | | | | |
| FGFR2 and FGFR 3 protein | Bladder cancer | To help determine treatment | X | | | | | |
| Fibrin/fibrinogen | Bladder cancer | To monitor progression and response to treatment | | | X | | | |
| FLT3 protein | Acute myeloid leukemia | To help determine treatment | | X | | | | |
| Gastrin | Gastrin-producing tumor (gastrinoma) | To help in diagnosis, monitor the effectiveness of treatment, and detect recurrence | | X | | | | |
| HE4 | Ovarian cancer | To plan cancer treatment, assess disease progression, and monitor for recurrence | | X | | | | |
| HER2/neu protein | Breast, ovarian, bladder, pancreatic, and stomach cancers | To help determine treatment | X | | | | | |
| 5-HIAA | Carcinoid tumors | To help in diagnosis and to monitor disease | | | X | | | |
| IDH1 and IDH2 protein | Acute myeloid leukemia | To help determine treatment | X | X | | | | |
| Immunoglobulins | Multiple myeloma and Waldenstrom macroglobulinemia | To help diagnose disease, assess response to treatment, and look for recurrence | | XX | | | | |
| IRF4 protein | Lymphoma | To help in diagnosis | X | | | | | |
| JAK2 protein | Certain types of leukemia | To help in diagnosis | X | X | | | | |
| KRAS protein | CRC and NSCLC | To help determine treatment | X | | | | | |

TABLE 1-continued

Commonly studied cancer biomarkers measured from different sample types.

| Biomarker | Cancer | Application | Tumor Tissue/ Bone Marrow | Blood | Urine | Stool | Cereb. Fluid | Saliva Buccal Swab |
|---|---|---|---|---|---|---|---|---|
| Lactate dehydrogenase | Germ cell tumors, lymphoma, leukemia, melanoma, and neuroblastoma | To assess stage, prognosis, and response to treatment | | X | | | | |
| MYC protein | Lymphomas and leukemias | To help in diagnosis and to help determine treatment | X | | | | | |
| MYD88 protein | Lymphoma and Waldenstrom macroglobulinemia | To help in diagnosis and to help determine treatment | X | | | | | |
| Myeloperoxidase (MPO) | Leukemia | To help in diagnosis | | X | | | | |
| Neuron-specific enolase (NSE) | Small cell lung cancer and neuroblastoma | To help in diagnosis and to assess response to treatment | | X | | | | |
| NTRK protein | Any solid tumor | To help determine treatment | X | | | | | |
| Nuclear matrix protein 22 | Bladder cancer | To monitor response to treatment | | | X | | | |
| PML/RARa protein | Acute promyelocytic leukemia | To diagnose, to predict response to all-trans-retinoic acid or arsenic trioxide therapy, to assess effectiveness of therapy, monitor minimal residual disease, and predict early relapse | X | X | | | | |
| Programmed death ligand 1 (PD-L1) | NSCLC, liver cancer, stomach cancer, gastroesophageal junction cancer, classical Hodgkin lymphoma, and other aggressive lymphoma subtypes | To help determine treatment | X | | | | | |
| Prostate-specific antigen (PSA) | Prostate cancer | To help in diagnosis, to assess response to treatment, and to look for recurrence | | X | | | | |
| Prostatic Acid Phosphatase (PAP) | Metastatic prostate cancer | To help in diagnosing poorly differentiated carcinomas | | X | | | | |
| ROSI protein | NSCLC | To help determine treatment | X | | | | | |
| Soluble mesothelin-related peptides (SMRP) | Mesothelioma | To monitor progression or recurrence | | X | | | | |
| Somatostatin receptor | Neuroendocrine tumors affecting the pancreas or gastrointestinal tract | To help determine treatment | X | | | | | |
| T-cell receptor | T-cell lymphoma | To help in diagnosis; sometimes to detect and evaluate residual disease | X | X | | | | |
| Terminal transferase (TdT) | Leukemia and lymphoma | To help in diagnosis | X | X | | | | |
| Thiopurine S-methyltransferase (TPMT) enzyme | Acute lymphoblastic leukemia | To predict the risk of severe bone marrow toxicity (myelosuppression) with thiopurine treatment | | X | | | X | |
| Thyroglobulin | Thyroid cancer | To evaluate response to treatment and to look for recurrence | | x | | | | |
| UGT1A1*28 variant homozygosity | CRC | To predict toxicity from irinotecan therapy | | X | | | | X |
| Urine catecholamines: VMA and HVA | Neuroblastoma | To help in diagnosis | | | X | | | |

TABLE 1-continued

Commonly studied cancer biomarkers measured from different sample types.

| Biomarker | Cancer | Application | Tumor Tissue/ Bone Marrow | Blood | Urine | Stool | Cereb. Fluid | Saliva Buccal Swab |
|---|---|---|---|---|---|---|---|---|
| Urokinase plasminogen activator (uPA) and plasminogen activator inhibitor (PAI-1) | Breast cancer | To determine the aggressiveness of cancer and guide treatment | X | | | | | |
| Methylation of MGMT promoter | Glioblastoma | Drug response to chemotherapy | X | | | | | |

NSCLC, non-small cell lung cancer; CRC, colorectal cancer; UGT1A1*28, variant with seven (TA) repeats; X, detected in sample.

TABLE 2

Biomarkers in the most common neuromuscular disorders classified by clinical application.

|  |  |  |  | Therapeutic Biomarkers |
|---|---|---|---|---|
| NMD | Diagnostic Biomarkers | Prognostic Biomarkers | Predictive Biomarkers | Surrogate Endpoint |
| DMD | CK<br>TTNI-2 | | | TTNI-2 |
| LGMDs | CK | | | |
| IIMs | CK<br>MSA (anti-cN1A)<br>MAA | MSA (anti-cN1A)<br>MAA | | CK |
| MG | AChR Abs<br>MuSK Abs<br>LRP4 Abs | MuSK Abs<br>Titin and RyR Abs<br>LRP4 Abs<br>Kv1.4 Abs | MuSK Abs | AChR Abs titer<br>MuSK Abs titer |
| LEMS | P/Q-type VGCC Abs | SOX1 Abs<br>N-type VGCC Abs<br>Onconeural Abs<br>GABAB receptor Abs | | |
| CMT | NfL<br>TMPRSS5<br>PMP22 | | | TMPRSS5<br>PMP22 |
| Dysimmune Neuropathies | Gangliosides Abs<br>MAG Abs<br>IL-8 | MAG Abs<br>Gangliosides Abs<br>NfL | MAG Abs | MAG Abs |
| SMA | SMN<br>pNfH | SMN<br>Creatinine | | SMN<br>pNfH<br>HSP70B<br>Aβ40-42 |
| ALS | NfL, pNfH<br>C9ORF72 (DPR)<br>TDP-43<br>TAU | CK<br>Creatinine<br>NfL, pNfH | | Creatinine<br>Aβ-42<br>SOD1<br>C9ORF72 (DPR) |

Abbreviations: Abs, antibodies; Aβ40, amyloid-β40; AchR, acetylcholine receptor; ALS, amyotrophic lateral sclerosis; CK, creatine kinase; cN1A, cytosolic 5'-nucleotidase 1A; DM1, myotonic dystrophy type 1; DMD, Duchenne muscular dystrophy; DPR, dipeptide repeat; HSP70B, heat shock 70 kDa protein 7; IIMs, inflammatory myopathies; IL-8, interleukine-8; LEMS, Lambert-Eaton myasthenic syndrome; LGMDs, limb-girdle muscular dystrophies; LRP4, lipoprotein-related protein 4; MG, myasthenia gravis; MAA, myositis-associated Abs; miRNA, microRNA; MSA, myositis-specific Abs; MuSK, muscle-specific kinase; NMD, neuromuscular disease; PMP-22, peripheral myelin protein 22; RYR, ryanodine receptor; SMA, spinal muscular atrophy; Nf, neurofilament; SMN, survival motor neuron; SOD1, superoxide dismutase 1; TAR DNA-binding protein 43 (TDP-43); TMPRSS, transmembrane protease serine 5; TTNI, serum troponin; VGCC, voltage-gated calcium channel.

TABLE 3

Environmental pollutants for measurement, their sources, and impact on human health.

| POLLUTANTS | | SOURCE | IMPACTS ON HUMAN HEALTH |
|---|---|---|---|
| Heavy metals | Lead | Paints, Lead-acid batteries | Encephalopathy, Peripheral Neuropathy, Anemia. Damage to the Liver, kidney, and brain, neurobehavioral changes, and abnormalities in fertility and pregnancy |

TABLE 3-continued

Environmental pollutants for measurement, their sources, and impact on human health.

| | POLLUTANTS | SOURCE | IMPACTS ON HUMAN HEALTH |
|---|---|---|---|
| | Mercury | Thermal power plants, hospital waste | Hypertension, Myocardial infarction, Proteinuria, cardiovascular diseases. |
| | Arsenic | Wood preservatives, pesticide | Respiratory Cancer, Dermatomes, Genetic toxicity |
| | Nickel | Smelting operations, battery industries | Cancer, Dramatis |
| | Cadmium | Tobacco smoke, batteries | Proteinuria, Glucosuria, Osteomalacia, Aminoaciduria, Emphysemia |
| | Sulfur dioxide ($SO_2$) | Fossil fuels combustion | Irritated airways and lungs. Prolonged exposure may lead to chronic bronchitis |
| | Carbon monoxide (CO) | Vehicular emission, Open fire | Cardiovascular and pulmonary diseases, asphyxiation. |
| | Nitrogen oxides ($NO_x$) | Fuel combustion | $NO_x$ gases can exacerbate respiratory illnesses and cardiovascular disease |
| Particulate matters | $PM_{2.5}$, $PM_{10}$ | Vehicular emission, Agricultural waste, Fuel, and wood burning | Chronic Pulmonary disease, bronchitis, asthma, respiratory and cardiovascular illness and mortality stroke, change in blood pressure. |
| Pesticides | Organochlorine compound | Dichloro-diphenyl-trichloroethane, DT, Dichlorodiphenyldichloroethane, Dicofol, Eldrin, Dieldrin | Damage human liver, kidney, neural and immune systems, and induces birth defects cancer, causes neurotoxicity, reproductive toxicity Inflammation of the upper respiratory tract and bronchitis, blood effects such as aplastic anemia |
| | Organophosphorus Compound | Malathion, parathion, diazinon, fenthion, dichlorvos, chlorpyrifos, ethion. | Reproductive Effects Immunotoxicity Cancer and Immunosuppression Hypertension tachycardia, and paralysis |
| | Carbamates | Sprays | Impair child development and IQ Decrease lung function Central nervous system tumor |
| | Pyrethrin &Pyrethroids | Sprays, dust, and pet shampoos | Paranesthesia, respiratory tract, eyes, and skin irritations cardiovascular disease |
| Plastics | High-density polyethylene | Plastic containers, pipes | Mild dermatitis, Respiratory damage, Hormone disruption |
| | Low-density polyethylene | Shrink wraps, squeeze bottles | Mild dermatitis, Burning sensation in eyes, Asthma |
| | Polyvinyl chloride | Cosmetic containers wrap | Respiratory damage, immune system damage |
| Plastic-Additives | Bisphenol A | Food storage containers, | Ovarian disorder |
| | Phthalates | Personal care products, Vinyl flooring, Polyvinyl chloride plastics | Endocrine disruptor Interference with testosterone, sperm motility, testicular cancer |
| | Dioxins | Tobacco smoke, Combustion of wood, coal, oil, Pesticides | Carcinogen interferes with testosterone |
| | Polycyclic aromatic hydrocarbons (PAHs) | Tobacco smoke, burning coal, oil, gas, wood, garbage | Developmental and reproductive toxicity |
| | Polychlorinated biphenyls (PCBs) | Contaminated fish, meat, and dairy products | Interferes with thyroid hormone |

TABLE 4

Amino acids for being measured by the device and its Raman band.

| Amino Acid Solution | Raman band (cm−1) |
|---|---|
| Alanine | 848m |
| Arginine | 1317m, 1365m, 1408m, 1446m |
| Aspartic acid | 939m, 1338m |
| Cystine | 499m |
| Glutamic acid | 871vw, 915vw, 1079vw, 1419vw |
| Glycine | 508m, 1332m, 1414m |
| Histidine | 1321w, 1355w, 1572w |
| Isoleucine | 765w, 820w, 877w, 1413w |
| Leucine | 1252w-br |
| Lysine | 1414m, 1447m |
| Methionine | 653m, 700m, 723m |
| Phenylalanine | 1005m |

TABLE 4-continued

Amino acids for being measured by the device and its Raman band.

| Amino Acid Solution | Raman band (cm−1) |
|---|---|
| Proline | 856m, 911m, 1041m |
| Serine | 857m, 1348m, 1413m, 1469m |
| Threonine | 776m, 1410m |
| Tryptophan | 759m, 1013m |
| Tyrosine | 831w |
| Valine | 757m, 829m, 948m, 1328m, 1336m, 1362m |
| Collagen | 1248m-br | s:strong, vs:very strong, m:medium, w:weak, vw:very weak, sh:shoulder, br:broad

TABLE 5

Hormones measured by the handheld device of present invention.

| Name | Effect |
|---|---|
| Adrenaline (or epinephrine) | increase systolic blood pressure, glycogenolysis, lipolysis, increase cardiac output, influence goosebumps, etc. |
| Melatonin | sleep-wake cycle |
| Noradrenaline (or norepinephrine) | increases both systolic and diastolic blood pressure, glycogenolysis, lipolysis increases metabolism, etc. |
| Triiodothyronine | increased metabolism |
| Thyroxine | Control carbohydrate, protein and fat metabolism and control physical, mental growth of body |
| Dopamine | regulation of cellular cAMP levels, prolactin antagonist |
| Prostaglandins | vasodilation |
| Leukotrienes | increase vascular permeability |
| Prostacyclin | vasodilation, platelet activation inhibitor |
| Thromboxane | vasoconstriction, Platelet Aggregation |
| Amylin (or Islet Amyloid Polypeptide) | slowing down gastric emptying, inhibition of digestive secretion, in order to reduce food intake |
| Anti-Mullerian hormone (or Mullerian-inhibiting factor/hormone) | Inhibit release of prolactin and TRH from anterior pituitary |
| Adiponectin | regulating glucose levels |
| Adrenocorticotropic hormone (or corticotropin) | synthesis of corticosteroids (glucocorticoids and androgens) in adrenocortical cells |
| Angiotensinogen and Angiotensin | vasoconstriction release of aldosterone from adrenal cortex dipsogen. |
| Antidiuretic hormone (or vasopressin, arginine vasopressin) | reabsorption of water in kidneys moderate vasoconstriction increase permeability of diastal tubule of nephrons (in Kidneys) to water Release ACTH in anterior pituitary |
| Atrial natriuretic peptide (or atriopeptin) | increase sodium and GFR excretion, antagonize venal constriction, inhibit renin secretion |
| Brain natriuretic peptide | (To a minor degree than ANP) reduce blood pressure by: reducing systemic vascular resistance, reducing blood water, sodium and fats |
| Calcitonin | Construct bone, reduce blood Ca2+ |
| Cholecystokinin | Release of digestive enzymes from pancreas Release of bile from gallbladder Hunger suppressant |
| Corticotropin-releasing hormone | Release ACTH from anterior pituitary |
| Cortistatin | depression of neuronal activity; induction of slow-wave sleep; reduction of locomotor activity; activation of cation selective currents not responsive to somatostatin |
| Enkephalin | Regulate pain |
| Endothelin | Smooth muscle contraction of medium-sized vessels |
| Erythropoietin | Stimulate erythrocyte production |
| Follicle-stimulating hormone | In female: stimulates maturation of Graafian follicles in ovary. In male: spermatogenesis, enhances production of androgen-binding protein by the Sertoli cells of the testes |
| Galanin | modulation and inhibition of action potentials in neurons |
| Gastric inhibitory polypeptide | Induces insulin secretion |
| Gastrin | Secretion of gastric acid by parietal cells |
| Ghrelin | Stimulate appetite, secretion of growth hormone from anterior pituitary gland |
| Glucagon | glycogenolysis and gluconeogenesis in liver, activates lipase enzyme in adipose tissue cells, increases blood glucose level, inhibits storage of triglyceride in liver |
| Glucagon-like peptide-1 | Stimulates the adenylyl cyclase pathway, resulting in increased synthesis and release of insulin |

TABLE 5-continued

Hormones measured by the handheld device of present invention.

| Name. | Effect |
|---|---|
| Gonadotropin-Releasing Hormone | Release of FSH and LH from anterior pituitary. |
| Growth Hormone-Releasing Hormone | Release GH from anterior pituitary |
| Hepcidin | inhibits iron export from cells |
| Human Chorionic Gonadotropin | promote maintenance of corpus luteum during beginning of pregnancy, Inhibit immune response, towards the human embryo, serves as the basis of early pregnancy test |
| Human placental lactogen | increase production of insulin and IGF-1 increase insulin resistance and carbohydrate intolerance |
| Growth hormone | stimulates growth and cell reproduction Release Insulin-like growth factor 1 from liver |
| Inhibin | Inhibit production of FSH |
| Insulin also called hypoglycemic hormone and anti ketogenic hormone ∥ | Intake of glucose, promotes glycogenesis, prevents glycogenolysis and neoglucogenesis, intake of lipids, synthesis of triglycerides in adipocytes, helps in oxidation of sugar through Krebs cycle, inhibits prodiction of ketone bodies, inactivates phosphorylase enzyme, Other anabolic effects |
| Insulin-like growth factor (or somatomedin) | insulin-like effects regulate cell growth and development |
| Leptin | decrease of appetite and increase of metabolism. |
| Lipotropin | lipolysis and steroidogenesis, stimulates melanocytes to produce melanin |
| Luteinizing hormone | In female: ovulation In male: stimulates Leydig cell production of testosterone |
| Melanocyte stimulating hormone | melanogenesis by melanocytes in skin and hair |
| Motilin | stimulates gastric activity |
| Orexin | wakefulness and increased energy expenditure, increased appetite |
| Osteocalcin | Favors muscle function, memory formation, testosterone synthesis and energy expenditure |
| Oxytocin (or pitocin) | release breast milk Stimulates contraction of cervix and vagina. Involved in orgasm, trust between people, and circadian homeostasis (body temperature, activity level, wakefulness). |
| Pancreatic polypeptide | Self-regulation of pancreatic secretions (endocrine and exocrine). It also affects hepatic glycogen levels and gastrointestinal secretions. |
| Parathyroid hormone | increase blood $Ca^{2+}$: indirectly stimulate osteoclasts $Ca^{2+}$ reabsorption in kidney activate vitamin D (Slightly) decrease blood phosphate: (decreased reuptake in kidney but increased uptake from bones activate vitamin D) |
| Pituitary adenylate cyclase-activating peptide | Stimulates enterochromaffin-like cells |
| Prolactin (or leuteotropic hormone) | milk production in mammary glands sexual gratification after sexual acts |
| Prolactin-releasing hormone | Release prolactin from anterior pituitary |
| Relaxin | Unclear in humans |
| Renin | Activates the renin-angiotensin system by producing angiotensin I of angiotensinogen |
| Secretin | Secretion of bicarbonate from liver, pancreas and duodenal Brunner's glands Enhances effects of cholecystokinin Stops production of gastric juice |
| Somatostatin (or growth hormone-inhibiting hormone or growth hormone release-inhibiting hormone or somatotropin release-inhibiting factor or somatotropin release-inhibiting hormone) | Inhibit release of GH and TRH from anterior pituitary Suppress release of gastrin, cholecystokinin (CCK), secretin, motilin, vasoactive intestinal peptide (VIP), gastric inhibitory polypeptide (GIP), enteroglucagon in gastrointestinal system Lowers rate of gastric emptying Reduces smooth muscle contractions and blood flow within the intestine Inhibit release of insulin from beta cells Inhibit release of glucagon from alpha cells Suppress the exocrine secretory action of pancreas. |
| Thrombopoietin | produce platelets |
| Thyroid-stimulating hormone (or thyrotropin) | secrete thyroxine ($T_4$) and triiodothyronine ($T_3$) |
| Thyrotropin-releasing hormone | Release thyroid-stimulating hormone (primarily) Stimulate prolactin release |
| Vasoactive intestinal peptide | stimulates contractility in the heart, causes vasodilation, increases glycogenolysis, lowers arterial blood pressure and relaxes the smooth muscle of trachea, stomach and gall bladder |
| Guanylin | regulates electrolyte and water transport in intestinal epithelia. |
| Uroguanylin | regulates electrolyte and water transport in renal epithelia. |

TABLE 6

Steroids measured by the handheld device of present invention.

| Name | Effect |
| --- | --- |
| Testosterone | libido, Anabolic: growth of muscle mass and strength, increased bone density, growth and strength, Virilizing: maturation of sex organs, formation of scrotum, deepening of voice, growth of beard and axillary hair. |
| Dehydroepiandrosterone | Virilization, anabolic |
| Androstenedione | Substrate for estrogen |
| Dihydrotestosterone | 5-DHT or DHT is a male reproductive hormone that targets the prostate gland, bulbourethral gland, seminal vesicles, penis and scrotum and promotes growth/mitosis/cell maturation and differentiation. Testosterone is converted to 5-DHT by 5alpha-reductase, usually with in the target tissues of 5-DHT because of the need for high concentrations of 5-dht to produce the physiological effects. |
| Aldosterone | Increase blood volume by reabsorption of sodium in kidneys (primarily) Potassium and $H^+$ secretion in kidney. |
| Estradiol | Females: Structural: promote formation of female secondary sex characteristics stimulate endometrial growth increase uterine growth maintenance of blood vessels and skin reduce bone resorption increase hepatic production of binding proteins Coagulation: increase circulating level of factors 2, 7, 9, 10, antithrombin III, plasminogen increase platelet adhesiveness Fluid balance: salt (sodium) and water retention increase growth hormone increase cortisol, SHBG Gastrointestinal tract: reduce bowel motility increase cholesterol in bile Lung function: promote lung function by supporting alveoli. Males: Prevent apoptosis of germ cells |
| Estrone | |
| Estriol | |
| Cortisol | Stimulation of gluconeogenesis Inhibition of glucose uptake in muscle and adipose tissue Mobilization of amino acids from extrahepatic tissues Stimulation of fat breakdown in adipose tissue anti-inflammatory and immunosuppressive |
| Progesterone | Support pregnancy: Convert endometrium to secretory stage Make cervical mucus permeable to sperm Inhibit immune response, e.g. towards the human embryo. Decrease uterine smooth muscle contractility Inhibit lactation Inhibit onset of labor Support fetal production of adrenal mineralo- and glucosteroids Other: Raise epidermal growth factor-1 levels Increase core temperature during ovulation Reduce spasm and relax smooth muscle (widen bronchi and regulate mucus) Antiinflammatory. Regulate immune response Reduce gall-bladder activity Normalize blood clotting and vascular tone, zinc and copper levels, cell oxygen levels, and use of fat stores for energy Assist in thyroid function and bone growth by osteoblasts Resilience in bone, teeth, gums, joint, tendon, ligament and skin healing by regulating collagen Nerve function and healing by regulating myelin Prevent endometrial cancer by regulating effects of estrogen |
| Calcitriol | Active form of vitamin D3 Increase absorption of calcium and phosphate from gastrointestinal tract and kidneys inhibit release of PTH |
| Calcidiol | Inactive form of vitamin $D_3$ |

What is claimed is:

1. A handheld Surface-Enhanced Raman Spectroscopy (SERS) device for detecting a biomarker in a sample collected from a subject, the device comprising:
- a laser generator configured to produce a laser beam;
- a nanoporous anodic aluminum oxide (NAAO) substrate configured to receive the sample collected from the subject; wherein the laser beam reaches the sample on the NAAO substrate and is scattered to produce a light signal; and
- a light sensor configured to receive the light signal scattered from the sample;
- wherein the laser generator, the NAAO substrate, and the light sensor are arranged on a base having a length less than 100 mm and a width less than 80 mm, such that the device is handheld and detects the biomarker in the sample;
- wherein the NAAO substrate comprises a multilayered nanoporous aluminum layer;

wherein the multilayered nanoporous aluminum layer comprises a base aluminum layer, and a nanoporous aluminum layer on top of the base aluminum layer;
- wherein the NAAO substrate is a gold layered NAAO substrate having a gold layer;
- wherein the gold layer comprises gold nanoparticles which are disposed on top of the NAAO substrate via a method of air-water-oil interfacial self-assembly;
- wherein the nanoporous aluminum layer comprises a plurality of nanocavities.

2. The handheld SERS device according to claim 1 further comprising a beam splitter located between the laser generator and the NAAO substrate.

3. The handheld SERS device according to claim 2 further comprising a bandpass filter located between the beam splitter and the light sensor;
- wherein the bandpass filter selectively permits the light signal having certain wavelengths to pass through; and
- wherein the certain wavelengths are adjustable.

4. The handheld SERS device according to claim 3, wherein the beam splitter permits the passing of the laser beam produced by the laser generator on one of its two sides, and is configured to reflect at least a portion of the light signal scattered by the sample on the NAAO substrate on the other of its two sides.

5. The handheld SERS device according to claim 3, wherein the certain wavelengths are selected for determining the biomarker in the sample.

6. The handheld SERS device according to claim 5, wherein the light sensor is configured to receive the light signal that passes through the bandpass filter.

7. The handheld SERS device according to claim 2 further comprising a test strip holder; wherein the test strip holder is configured to receive a test strip comprising the NAAO substrate.

8. The handheld SERS device according to claim 7 further comprising a focusing lens; wherein the focusing lens is disposed between the test strip holder and the beam splitter.

9. The handheld SERS device according to claim 1, wherein the gold nanoparticles are nanorods.

10. The handheld SERS device according to claim 1, wherein the NAAO substrate has a high surface area to volume ratio.

11. The handheld SERS device according to claim 3, wherein the device comprises a communication unit communicating with an interactive display for receiving an input and displaying an output; wherein the communication unit comprises a Wi-Fi unit.

12. The handheld SERS device according to claim 11, wherein the input comprises the biomarker.

13. The handheld SERS device according to claim 12, wherein the certain wavelengths are configured to be adjusted according to the biomarker.

14. The handheld SERS device according to claim 1, wherein the biomarker comprises a biomarker of a dementia disease.

15. The handheld SERS device according to claim 1, wherein the biomarker comprises a biomarker of a cancer.

16. The handheld SERS device according to claim 1, wherein the biomarker comprises a biomarker of a heart disease.

17. The handheld SERS device according to claim 1, wherein the biomarker comprises a biomarker of a neuromuscular disorder.

18. The handheld SERS device according to claim 1, wherein the biomarker comprises a hormone or a steroid.

19. The handheld SERS device according to claim 1, wherein the biomarker comprises a nutrient.

20. A handheld Surface-Enhanced Raman Spectroscopy (SERS) device for detecting a biomarker in a sample collected from a subject, the device comprising:
- a laser generator configured to produce a laser beam;
- a nanoporous anodic aluminum oxide (NAAO) substrate configured to receive the sample collected from the subject; wherein the laser beam reaches the sample on the NAAO substrate and is scattered to produce a light signal; and
- a light sensor configured to receive the light signal scattered from the sample;
- wherein the laser generator, the NAAO substrate, and the light sensor are arranged on a base having a length less than 100 mm and a width less than 80 mm, such that the device is handheld and detects the biomarker in the sample.

21. The handheld SERS device according to claim 20, wherein the NAAO substrate comprises a multilayered nanoporous aluminum layer; wherein the multilayered nanoporous aluminum layer comprises a base aluminum layer, and a nanoporous aluminum layer on top of the base aluminum layer.

22. The handheld SERS device according to claim 21, wherein the NAAO substrate is a gold layered NAAO substrate having a gold layer.

23. The handheld SERS device according to claim 22, wherein the gold layer comprises gold nanoparticles which are disposed on top of the NAAO substrate via a method of air-water-oil interfacial self-assembly.

24. The handheld SERS device according to claim 21, wherein the nanoporous aluminum layer comprises a plurality of nanocavities.

* * * * *